United States Patent
Yamamoto et al.

(10) Patent No.: US 8,053,592 B2
(45) Date of Patent: Nov. 8, 2011

(54) METHOD FOR PRODUCING OPTICALLY ACTIVE α-IONONE

(75) Inventors: Tetsuya Yamamoto, Iwata (JP); Kenji Yagi, Hiratsuka (JP); Kenya Ishida, Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 13/012,199

(22) Filed: Jan. 24, 2011

(65) Prior Publication Data

US 2011/0118500 A1 May 19, 2011

Related U.S. Application Data

(62) Division of application No. 11/991,966, filed as application No. PCT/JP2006/318133 on Sep. 13, 2006, now Pat. No. 7,902,404.

(30) Foreign Application Priority Data

Sep. 13, 2005 (JP) ................. 2005-265643

(51) Int. Cl.
*C07C 69/78* (2006.01)
*C07C 69/533* (2006.01)
*C07C 69/63* (2006.01)

(52) U.S. Cl. ........ 560/106; 560/128; 560/225; 560/227; 560/228; 560/231

(58) Field of Classification Search .................. 560/128, 560/106, 225, 227, 228, 231
See application file for complete search history.

(56) References Cited

U.S. PATENT DOCUMENTS 3,940,499 A   2/1976  Pittet et al.
5,705,372 A   1/1998  Belin et al.

FOREIGN PATENT DOCUMENTS

DE  25 40 624 A1  4/1976
JP  10-084988 A   4/1998
JP  10-084989 A   4/1998

OTHER PUBLICATIONS

Oritani, T. et al., "Synthesis and absolute stereochemistry of chiral-ionone and dihydro-ionone" (1987), Agric. Biol. Chem,. vol. 51, No. 5, p. 1271-1275.
Sugai, Takeshi et al, "A Synthetic Study of (−)-Dihydroedulan II and Related Compounds", Tetrahedron vol. 47, No. 35, pp. 7227-7236, 1991.
Bovolenta et al. "A Simple and Efficient Highly Enantioselective Synthesis of Alpha-Ionone and Alpha-Damascone," Journal of Organic Chemistry, vol. 69, pp. 8959-8962 (2004).
Fuganti et al., "Synthesis and Olfactory Evaluation of (+)- and (−)-γ-Ionone," Helvetica Chimica Acta, vol. 83, pp. 2761-2768, 2000.

*Primary Examiner* — Sikarl Witherspoon
(74) *Attorney, Agent, or Firm* — Venable LLP; Keith G. Haddaway; Michael E. Nelson

(57) ABSTRACT

Provided that a method for inexpensively producing optically active α-ionone with a high yield and a high asymmetric yield and with good workability in a short process, and a perfume composition comprising the optically active α-ionone obtained by the aforementioned method. A method for producing optically active α-ionone, comprising allowing α-ionone as a mixture of optical isomers to react with an esterification agent, and hydrolyzing the obtained α-ionone enol ester; a method for producing optically active α-ionone comprising subjecting α-ionone as a mixture of optical isomers to an asymmetric reduction, allowing the obtained optically active α-ionol to react with an esterification agent to give an optically active α-ionol ester, hydrolyzing the obtained optically active α-ionol ester after purification as necessary, and then oxidizing the obtained optically active α-ionol; and a perfume composition comprising thus obtained optically active α-ionone.

13 Claims, No Drawings

US 8,053,592 B2

METHOD FOR PRODUCING OPTICALLY ACTIVE α-IONONE

This application is a Divisional of U.S. patent application Ser. No. 11/991,966 filed Apr. 20, 2009, now U.S. Pat. No. 7,902,404, which is a National Stage of International Application No. PCT/JP2006/318133, filed Sep. 13, 2006, which claims the benefit of Japanese Patent Application No. 2005-265643, filed Sep. 13, 2005, all of which are incorporated herein by reference in their entirety.

TECHNICAL FIELD

The present invention relates to a method for producing optically active α-ionone that is useful as a perfume, an intermediate for a pharmaceutical, a pesticide and the like.

BACKGROUND ART

α-ionone is a compound found from various essential oils. It has a floral that is stronger than that of β- or γ-ionone. Racemic α-ionone has a violet-like flavor (aroma), and it is used as a perfume. On the other hand, optically active α-ionone, (R)-α-ionone and (S)-α-ionone have been found in the nature. The former (R) form has a unique and strong floral flavor (aroma), such as a violet-like, fruit-like, raspberry-like flavor. The latter (S) form has a unique and strong flavor (aroma), such as a fresh juicy greenish flavor, including a wood-like, cedarwood-like, raspberry-like, and β-ionone-like flavor (aroma).

As a method for producing such optically active α-ionone, Patent Document 1 describes a method for producing optically active α-ionone in 5 steps using 2,4,4-trimethyl-2-cyclohexen-1-ol as a raw material. However, the method described in Patent Document 1 contains a step of allowing optically active 2,6,6-trimethyl-2-cyclohexen-1-ylacetaldehyde obtained as an intermediate to react with potassium cyanide. Thus, this method has been problematic in that it has poor workability and in that it is unfit for an industrial production.

In addition, Non-Patent Document 1 describes a method for producing (R)-(+)-α-ionone and (S)-(−)-α-ionone, that is optically resolving α-cyclogeranic acid to give (R)-(+)-α-cyclogeranic acid and (S)-(−)-α-cyclogeranic acid, and then using these compounds as raw materials. The method, however, described in Non-Patent Document 1 requires 4 steps. Thus, this method is poor in terms of yield and efficiency, and it is unfit for an industrial production. Moreover, Non-Patent Document 1 describes a method for purifying (R)-α-ionone in total 5 steps, that is epoxidation of the double bond of the cyclohexene ring of (R)-α-ionone. This method, however, includes 5 steps, and thus it has been problematic not only in that it is expensive, but also in that it is unfit for an industrial production.

Patent Document 1: Japanese Patent Laid-Open No. 10-84989

Non-Patent Document 1: Agric. Biol. Chem., vol. 51, No. 5, 1271-1275 (1987).

DISCLOSURE OF THE INVENTION

The present invention has been made under the aforementioned circumstances. It is an object of the present invention to provide a method for inexpensively producing optically active α-ionone with a high yield and a high asymmetric yield and with good workability in a short process, and a perfume composition comprising the optically active α-ionone obtained by the aforementioned method.

As a result of intensive studies directed towards achieving the aforementioned object, the present inventors have found that desired optically active α-ionone can be inexpensively obtained with a high yield and a high asymmetric yield and with good workability in a short process by a production method, which comprises allowing α-ionone as a mixture of optical isomers used as a raw material to react with an esterification agent, hydrolyzing, and in particular, enantioselectively hydrolyzing, or asymmetrically reducing the obtained α-ionone enol ester, then allowing the reaction product to react with an esterification agent, then isolating the obtained ester body, for example, at least one diastereomer of an ester body as a mixture of diastereomers, and then hydrolyzing the diastereomer, thereby completing the present invention.

That is to say, the present invention is as follows:

1) A method for producing an α-ionone enol ester, comprising allowing α-ionone as a mixture of optical isomers to react with an esterification agent.

2) A method for producing optically active α-ionone, comprising hydrolyzing an α-ionone enol ester.

3) A method for producing optically active α-ionone, comprising allowing α-ionone as a mixture of optical isomers to react with an esterification agent and hydrolyzing the obtained α-ionone enol ester.

3-1) The method according to 2) or 3) above, wherein the hydrolysis is enantioselective hydrolysis.

3-2) A method for producing optically active α-ionone, comprising allowing α-ionone as a mixture of optical isomers to react with an esterification agent, and enantioselectively hydrolyzing the obtained α-ionone enol ester.

3-3) A method for purifying optically active α-ionone, comprising allowing α-ionone as a mixture of optical isomers to react with an esterification agent, and hydrolyzing the obtained α-ionone enol ester.

4) The method for producing optically active α-ionone according to 2) or 3) above, characterized in that the hydrolysis is carried out in the presence of enzyme.

5) The method for producing optically active α-ionone according to any one of 1) to 3) above, characterized in that the α-ionone enol ester is a racemic form or an optically active substance.

6) A method for producing an α-ionone enol ester, comprising allowing α-ionone as a mixture of optical isomers to react with an esterification agent, enantioselectively hydrolyzing the obtained α-ionone enol ester in the presence of enzyme, and obtaining an unhydrolyzed α-ionone enol ester.

6-2) A method for producing optically active α-ionone, comprising enantioselectively hydrolyzing the α-ionone enol ester obtained in 6) above.

7) The method for producing optically active α-ionone according to 6-2) above, characterized in that the optically active α-ionone obtained in 6-2) above is an enantiomer of the optically active α-ionone obtained by enantioselective hydrolysis with enzyme.

8) A method for producing an α-ionone enol ester, characterized in that subjecting α-ionone as a mixture of optical isomers to an asymmetric reduction, and allowing the obtained optically active α-ionol to react with an esterification agent.

9) The method according to 8) above, comprising purifying at least one diastereomer of the obtained optically active α-ionol ester.

10) A method for producing optically active α-ionol, comprising hydrolyzing the optically active α-ionol ester obtained in 8) or 9) above.

11) A method for producing optically active α-ionone, comprising oxidizing the optically active α-ionol obtained in 10) above.

11-2) A method for producing optically active α-ionone, comprising subjecting α-ionone as a mixture of optical isomers to an asymmetric reduction, allowing the obtained optically active α-ionol to react with an esterification agent to give an optically active α-ionol ester, hydrolyzing the obtained optically active α-ionol ester, and then oxidizing the obtained optically active α-ionol.

11-3) A method for producing the optically active α-ionone according to 11-2) above, comprising subjecting α-ionone as a mixture of optical isomers to an asymmetric reduction, allowing the obtained optically active α-ionol to react with an esterification agent to give an optically active α-ionol ester as a mixture of diastereomers, isolating at least one diastereomer, hydrolyzing the obtained optically active α-ionol ester, and then oxidizing the obtained optically active α-ionol.

12) An α-ionone enol ester.

12-2) The α-ionone enol ester according to 12) above, characterized in that it has the following structure:

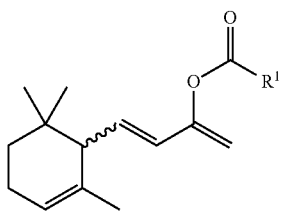

(3)

wherein $R^1$ represents a hydrogen atom or an optionally substituted hydrocarbon group.

13) A perfume, comprising optically active α-ionone obtained by the production method according to any one of 2) to 7) and 11) above.

14) A perfume composition, comprising the perfume according to 13) above.

15) The perfume composition according to 14) above, characterized in that it is a flavor composition or a fragrance composition.

16) A flavor composition, characterized in that the optically active α-ionone obtained by the production method according to any one of 2) to 7) and 11) above is included in a perfume composition at 0.0000001% to 1% by mass based on the total amount of the perfume composition.

17) A fragrance composition, characterized in that the optically active α-ionone obtained by the production method according to any one of 2) to 7) and 11) above is included in a perfume composition at 0.001% to 5% by mass based on the total amount of the perfume composition.

18) A food and beverage, an oral care product, or a pharmaceutical, comprising the perfume composition according to 15) above.

19) A fragrance product, comprising the perfume composition according to 15) above.

20) Daily goods, comprising the perfume composition according to 15) above.

21) A method for producing optically active α-ionone, comprising: a first step of allowing α-ionone as a mixture of optical isomers to react with an esterification agent; a second step of hydrolyzing the obtained α-ionone enol ester to give optically active α-ionone; a third step of subjecting the obtained optically active α-ionone to an asymmetric reduction to give optically active α-ionol; a fourth step of allowing the obtained optically active α-ionol to react with an esterification agent to give an optically active α-ionol ester; a fifth step of hydrolyzing the obtained optically active α-ionol ester; and a sixth step of oxidizing the obtained optically active α-ionol.

When compared with the conventional methods, the present invention can more inexpensively produce desired optically active α-ionone with a higher yield and a higher asymmetric yield, with better workability, and further in a shorter process. In addition, the present invention also can provide a perfume composition having good flavor (aroma) persistence, stability and higher preference, using the optically active α-ionone obtained by the production method of the present invention.

BEST MODE FOR CARRYING OUT THE INVENTION

The α-ionone used in the present invention is 4-(2,6,6-trimethyl-2-cyclohexen-1-yl)-3-buten-2-one. It is α-ionone represented by formula (1):

[Formula 1]

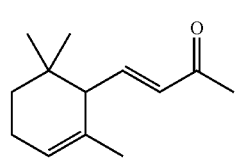

(1)

As described later, said α-ionone is a compound having an optically active site at the 1-position of a cyclohexene ring in the structural formula thereof (hereinafter simply referred to as "1-position" at times).

The optically active substance of the aforementioned α-ionone is optically active α-ionone represented by the formula (2):

[Formula 2]

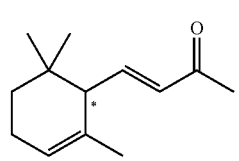

(2)

wherein * represents an asymmetric carbon atom.

Said optically active substance of the aforementioned α-ionone is (S)-α-ionone represented by formula (2A):

[Formula 3]

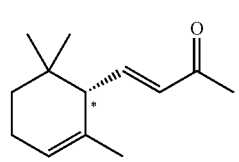

(2A)

wherein * has the same meaning as described above, or (R)-α-ionone represented by formula (2B):

[Formula 4]

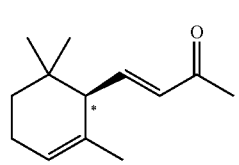

(2B)

wherein * has the same meaning as described above.

A method for producing the optically active α-ionone of the present invention, first, allows to react α-ionone as a mixture of optical isomers with an esterification agent to give an α-ionone enol ester. Either one of optical active substances of the obtained α-ionone enol ester is hydrolyzed to give optically active α-ionone and/or an α-ionone enol ester. Subsequently, the obtained optically active α-ionone and α-ionone enol ester are separately collected, namely, each of them is fractionated. Further, the fractionated α-ionone enol ester is subjected to enantioselective hydrolysis to give the second α-ionone.

In the present invention, α-ionone as a mixture of optical isomers used as a raw material may be either a racemic form (that is, its optical purity is 0%; the same is applied below) or an optically active substance.

When such α-ionone as a mixture of optical isomers is a racemic form, it is a mixture of the optical isomers of the α-ionone represented by the above formula (1), that is to say, a mixture of the (S)-α-ionone represented by the above formula (2A) and the (R)-α-ionone represented by the above formula (2B).

On the other hand, when such α-ionone as a mixture of optical isomers is an optically active substance, it has such an optical purity that the amount of either one of optical isomers is larger than that of the other optical isomer, that is to say, the amount of either the (S)-α-ionone represented by the above formula (2A) or the (R)-α-ionone represented by the above formula (2B) is larger than that of the other one. With regard to the optical purity of α-ionone as a mixture of optical isomers in a case where the α-ionone is an optically active substance, the optical purity is the one in a case that the amount of either one of optical isomers is larger than that of the other optical isomer. Specifically, such an optical purity is appropriately selected from the range, for example, of 1% e.e. or more, preferably from 1% to 99% e.e., and more preferably from 5% to 95% e.e.

The cis-trans-isomerism of the double bond at the 2-position of the aforementioned α-ionone as a mixture of optical isomers is not particularly limited, and it may be a cis form, a trans form, or a mixture thereof. In the present invention, the same holds for the optically active α-ionone, optically active α-ionone enol ester, optically active α-ionol, etc. as described below.

Such α-ionone as a mixture of optical isomers to be used may be either a commercially available product, or an appropriately produced one. In addition, when an optically active substance is used as α-ionone as a mixture of optical isomers, optically active α-ionone that has been appropriately produced may be used. Otherwise, optically active α-ionone obtained by the production method of the present invention may also be used.

An α-ionone enol ester obtained by allowing α-ionone as a mixture of optical isomers to react with an esterification agent is, for example, represented by formula (3):

[Formula 5]

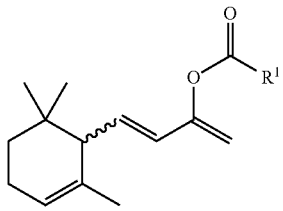

(3)

wherein R¹ represents a hydrogen atom or an optionally substituted hydrocarbon group.

Specific examples of the α-ionone enol ester represented by the formula (3) include compounds as shown below, and such α-ionone enol esters include racemic forms and optically active substances:

[Formula 6]

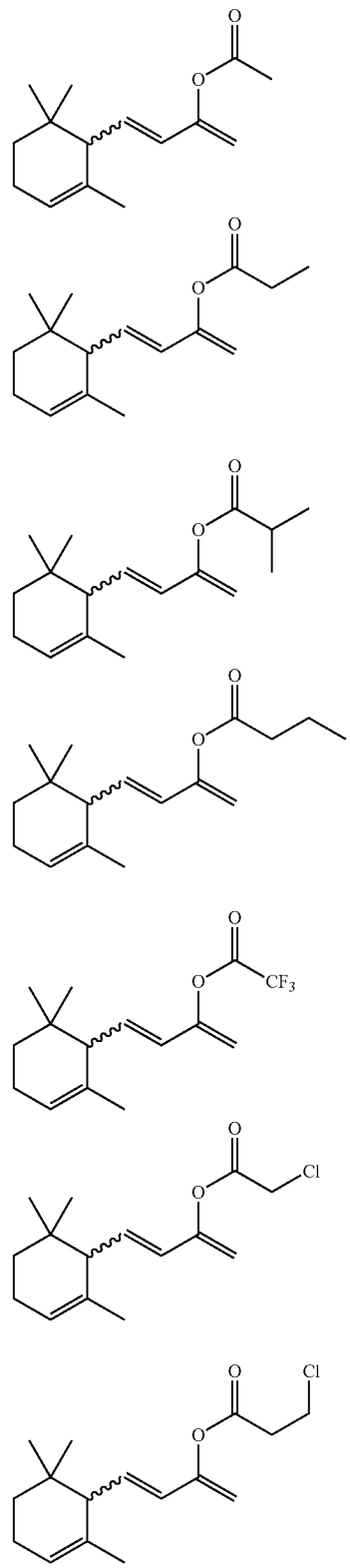

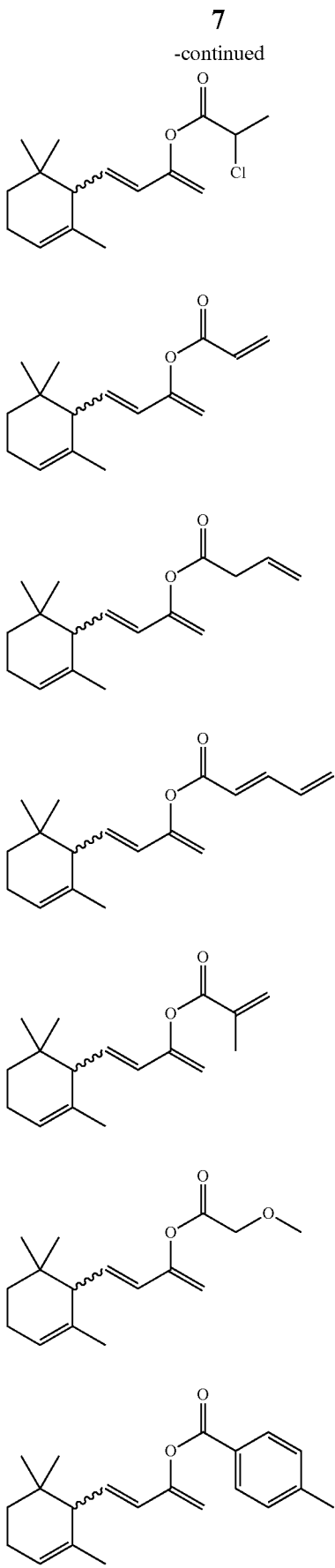

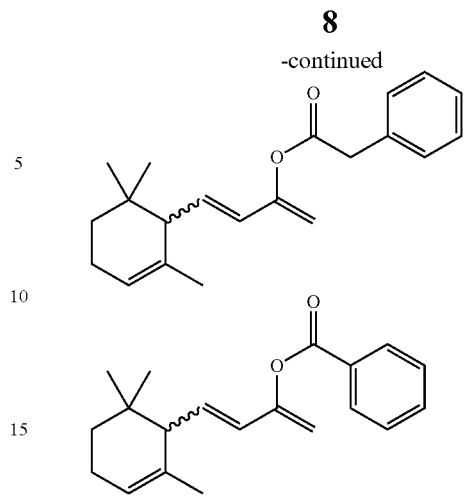

The α-ionone enol ester represented by the above formula (3) may be obtained in a racemic form or in an optically active form depending on α-ionone as a mixture of optical isomers used as a raw material in the aforementioned esterification. For example, when such α-ionone as a mixture of optical isomers used as a raw material is a racemic form, the obtained α-ionone enol ester is the form of a racemic form. When such α-ionone is an optically active substance, the obtained α-ionone enol ester is an optically active α-ionone enol ester. Moreover, the optically active α-ionone enol ester may be obtained in the form of a racemic form or an optically active substance, depending on the type of an esterification agent used, reaction conditions, etc.

The optical purity of the optically active α-ionone enol ester is appropriately selected from the range, for example, of 1% e.e or more, preferably from 1% to 99% e.e., and more preferably from 5% to 95% e.e. What is more, the obtained optically active α-ionone enol ester can be subjected to a post-treatment as described later or the like, as necessary, to give an optically active substance having an optical purity of substantially 100% e.e. The expression "substantially 100% e.e." is used herein in the present invention to mean that the optical purity is appropriately selected from the range of 80% e.e. or more, preferably 85% e.e. or more, more preferably 90% e.e. or more, and further more preferably 95% e.e. or more (the same is applied below).

The optically active substance of the α-ionone enol ester represented by the above formula (3) includes, for example, an optically active α-ionone enol ester represented by formula (3C):

[Formula 7]

(3C)

wherein $R^1$ and * have the same meanings as described above.

Specific examples of such an optically active α-ionone enol ester include an (S)-α-ionone enol ester represented by formula (3A):

[Formula 8]

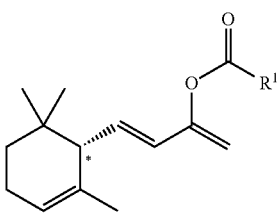

(3A)

wherein R¹ and * have the same meanings as described above, and an (R)-α-ionone enol ester represented by formula (3B):

[Formula 9]

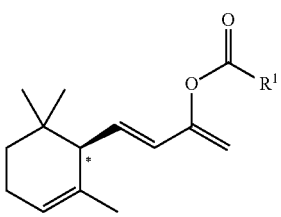

(3B)

wherein R¹ and * have the same meanings as described above.

Moreover, when the α-ionone enol ester represented by the above formula (3) is a racemic form, it is a mixture of the (S)-α-ionone enol ester represented by the above formula (3A) and the (R)-α-ionone enol ester represented by the above formula (3B).

An esterification agent allowed to react with α-ionone as a mixture of optical isomers include, for example, an acid anhydride and an acid halide. Specific examples of such an esterification agent include a compound represented by formula (11):

[Formula 10]

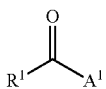

(11)

wherein R¹ represents a hydrogen atom or an optionally substituted hydrocarbon group, and A¹ represents a leaving group.

In the formula (11), the optionally substituted hydrocarbon group represented by R¹ include a hydrocarbon group and a substituted hydrocarbon group.

Examples of a hydrocarbon group include an alkyl group, an alkenyl group, an alkynyl group, an alkadienyl group, an aryl group, and an aralkyl group.

Such an alkyl group includes a linear, branched, or cyclic alkyl group having, for example, 1 to 20, preferably 1 to 15, and more preferably 1 to 10 carbon atom(s). Specific examples of such an alkyl group include methyl, ethyl, n-propyl, 2-propyl, n-butyl, 1-methylpropyl, isobutyl, tert-butyl, n-pentyl, 1-methylbutyl, tert-pentyl, 2-methylbutyl, 3-methylbutyl, 2,2-dimethylpropyl, n-hexyl, 1-methylpentyl, 1-ethylbutyl, tert-hexyl[$CH_3CH_2CH_2C(CH_3)_2$—], 2-methylpentyl, 3-methylpentyl, 4-methylpentyl, 2-methylpentan-3-yl, heptyl, octyl, nonyl, decyl, lauryl, stearyl, cyclopropyl, cyclobutyl, cyclopentyl, and cyclohexyl.

Such an alkenyl group includes a linear or branched alkenyl group having, for example, 2 to 20, preferably 2 to 15, and more preferably 2 to 10 carbon atoms. Specific examples of such an alkenyl group include vinyl, propenyl, butenyl, pentenyl, hexenyl, heptenyl, octenyl, nonenyl, and decenyl.

Such an alkynyl group includes a linear or branched alkynyl group having, for example, 2 to 20, preferably 2 to 15, and more preferably 2 to 10 carbon atoms. Specific examples of such an alkynyl group include ethynyl, propynyl, butynyl, pentynyl, and hexynyl.

Such an alkadienyl group includes a linear, branched, or cyclic alkadienyl group having two double bonds in the chain of the aforementioned alkyl group and having, for example, 4 or more, preferably 4 to 20, more preferably 4 to 15 carbon atoms, and further more preferably 4 to 10 carbon atoms. Specific examples of such an alkadienyl group include 1,3-butadienyl and 2,3-dimethyl-1,3-butadienyl.

Such an aryl group includes an aryl group having, for example, 6 to 20, and preferably 6 to 15 carbon atoms. Specific examples of such an aryl group include phenyl, naphthyl, anthryl, and biphenyl.

Such an aralkyl group includes an aralkyl group having, for example, 7 to 20, and preferably 7 to 15 carbon atoms, wherein at least one hydrogen atom of the aforementioned alkyl group is substituted with the aforementioned aryl group. Specific examples of such an aralkyl group include benzyl, 1-phenylethyl, 2-phenylethyl, 1-phenylpropyl, and 3-naphthylpropyl.

A substituted hydrocarbon group [a hydrocarbon group having a substituent(s)] includes a hydrocarbon group wherein at least one hydrogen atom of the aforementioned hydrocarbon group is substituted with a substituent(s). Specific examples of such a substituted hydrocarbon group include a substituted alkyl group, a substituted alkenyl group, a substituted alkynyl group, a substituted alkadienyl group, a substituted aryl group, and a substituted aralkyl group.

It is preferable to use an optionally substituted hydrocarbon group having 1 to 6 carbon atom(s) among such optionally substituted hydrocarbon groups.

A substituent include, for example, an optionally substituted hydrocarbon group, an optionally substituted heterocyclic group, a halogen atom, a halogenated hydrocarbon group, an optionally substituted alkoxy group, an optionally substituted aryloxy group, an optionally substituted aralkyloxy group, an optionally substituted heteroaryloxy group, an optionally substituted alkylthio group, an optionally substituted arylthio group, an optionally substituted aralkylthio group, an optionally substituted heteroarylthio group, an optionally substituted acyl group, an optionally substituted acyloxy group, an optionally substituted alkoxycarbonyl group, an optionally substituted aryloxycarbonyl group, an optionally substituted aralkyloxycarbonyl group, an optionally substituted alkylenedioxy group, a nitro group, an amino group, a substituted amino group, a cyano group, a sulfo group, a substituted silyl group, a hydroxy group, a carboxy group, an optionally substituted alkoxythiocarbonyl group, an optionally substituted aryloxythiocarbonyl group, an optionally substituted aralkyloxythiocarbonyl group, an optionally substituted alkylthiocarbonyl group, an optionally substituted arylthiocarbonyl group, an optionally substituted aralkylthiocarbonyl group, an optionally substituted carbamoyl group, a substituted phosphino group, an aminosulfonyl group, an alkoxysulfonyl group, and an oxo group. Such an optionally substituted hydrocarbon group, an optionally substituted heterocyclic group, a halogen atom, an optionally substituted acyloxy group, an optionally substituted alkoxy group, an optionally substituted aryloxy group, or the like may be the same as those described in the present specification. Such substituents may be appropriately selected from groups that do not directly influence the production method of the present invention.

With regard to such a substituted hydrocarbon group, specific examples of a substituted alkyl group include trifluoromethyl, methoxymethyl, and ethoxyethyl. Specific examples of a substituted aryl group include tolyl (e.g. 4-methylphenyl), xylyl (e.g. 3,5-dimethylphenyl), 4-methoxy-3,5-dimethylphenyl, and 4-methoxy-3,5-di-tert-butylphenyl.

A leaving group represented by $A^1$ may be either a group having a function that is eliminated from an esterification agent as a result of the reaction of the agent with α-ionone as a mixture of optical isomers to generate an α-ionone enol ester, or a group having a function that is eliminated from an esterification agent as a result of the reaction of the agent with optically active α-ionol as described, later to generate an optically active α-ionol ester. The aforementioned leaving group include, for example, an optionally substituted acyloxy group and a halogen atom.

Such an optionally substituted acyloxy group as a leaving group includes an acyloxy group and a substituted acyloxy group.

Such an acyloxy group includes an acyloxy group having 1 to 20 carbon atom(s) derived from carboxylic acid such as aliphatic carboxylic acid and aromatic carboxylic acid, and includes, for example, a group represented by —OCOR² (wherein R² represents a hydrogen atom or a optionally substituted hydrocarbon group). In the above —OCOR², the optionally substituted hydrocarbon group represented by $R^2$ is the same optionally substituted hydrocarbon group as described in $R^1$ above.

Specific examples of an acyloxy group include acetoxy, propionyloxy, butyryloxy, pivaloyloxy, pentanoyloxy, hexanoyloxy, lauroyloxy, stearoyloxy, and benzoyloxy. It is preferable to use an acyloxy group having 2 to 18 carbon atoms among the aforementioned acyloxy group.

A substituted acyloxy group [an acyloxy group having a substituent(s)] includes an acyloxy group wherein at least one hydrogen atom of the aforementioned acyloxy group is substituted with the aforementioned substituent(s).

A halogen atom as a leaving group includes a fluorine atom, a chlorine atom, a bromine atom, and an iodine atom.

When the esterification agent is an acid anhydride, such an acid anhydride includes, for example, an acid anhydride represented by formula (11-1), which corresponds to an acid anhydride represented by the above formula (11) wherein the leaving group represented by $A^1$ in the above formula (11) is —OCOR² (wherein $R^2$ has the same meaning as described above):

[Formula 11]

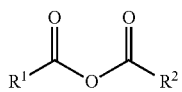

(11-1)

wherein $R^1$ and $R^2$ have the same meanings as described above.

Specific examples of such an acid anhydride include acetic anhydride, propionic anhydride, maleic anhydride, phthalic anhydride, succinic anhydride, pyromellitic anhydride, itaconic anhydride, chloroacetic anhydride, benzoic anhydride, oxalic anhydride, succinic anhydride, glycolic anhydride, acrylic anhydride, methacrylic anhydride, citraconic anhydride, mesaconic anhydride, trimellitic anhydride, and adipic anhydride. Such an acid anhydride may be either a symmetric acid anhydride, wherein, in the above formula (11-1), $R^1$ and $R^2$ are the same groups ($R^1$=$R^2$), or an asymmetric acid anhydride, wherein $R^1$ and $R^2$ are different groups ($R^1$≠$R^2$). A symmetric acid anhydride, wherein $R^1$ and $R^2$ are the same groups, is preferable.

On the other hand, when the esterification agent is an acid halide, such an acid halide includes, for example, an acid halide represented by following formula (11-2), which corresponds to an acid halide represented by the above formula (11) wherein the leaving group represented by $A^1$ in the above formula (11) is a halogen atom:

[Formula 12]

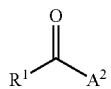

(11-2)

wherein $A^2$ represents a halogen atom and $R^1$ has the same meaning as described above.

In the formula (11-2), the halogen atom represented by $A^2$ is identical to the halogen atom described in the above leaving group represented by $A^1$.

Specific examples of an acid halide include acetyl chloride, acetyl bromide, acetyl iodide, propionyl chloride, butyryl chloride, pivaloyl chloride, pentanoyl chloride, hexanoyl chloride, lauroyl chloride, stearoyl chloride, benzoyl chloride, 1-naphthoyl chloride, phthaloyl chloride, 2,4-dichlorobenzoyl chloride, and methacryloyl chloride. Such esterification agents may be used appropriately singly or in combination of two or more thereof.

When the aforementioned esterification agent is allowed to react with α-ionone as a mixture of optical isomers, it is preferable to use an acid anhydride among such an esterification agent.

The amount of α-ionone as a mixture of optical isomers used and the amount of an esterification agent used are not particularly limited because they are different depending on the type of the esterification agent used, etc. The amount of such an esterification agent used is appropriately selected from the range of generally 0.5 to 5 equivalents, and preferably 0.8 to 2.0 equivalents, based on the α-ionone as a mixture of optical isomers used as a raw material.

Esterification of allowing α-ionone as a mixture of optical isomers to react with an esterification agent is preferably carried out in the presence of a basic substance. Such a basic substance includes an inorganic base and an organic base. Examples of an inorganic base include alkali metal hydroxides such as lithium hydroxide, sodium hydroxide, and potassium hydroxide; metal carbonates such as sodium carbonate, potassium carbonate, magnesium carbonate, and calcium carbonate; metal hydrogencarbonates such as sodium hydrogencarbonate, and potassium hydrogencarbonate; metal hydrides such as lithium hydride, sodium hydride, and potassium hydride; and ammonia. Examples of an organic base include alkali or alkaline-earth metal salts such as lithium methoxide, lithium ethoxide, lithium-tert-butoxide, sodium methoxide, sodium ethoxide, sodium-tert-butoxide, potassium methoxide, potassium ethoxide, potassium-tert-butoxide, potassium naphthalenide, sodium acetate, potassium acetate, magnesium acetate, calcium acetate, lithium diethylamide, lithium diisopropylamide, lithium bis(trimethylsilyl)amide, sodium bis(trimethylsilyl)amide, potassium bis(trimethylsilyl) amide, lithium diphenylphosphide, sodium diphenylphosphide, and potassium diphenylphosphide; organic amines such as triethylamine, diisopropylethylamine, N,N-dimethylaniline, piperidine, pyridine, 4-dimethylaminopyridine, 1,5-diazabicyclo[4.3.0]non-5-ene, 1,8-diazabicyclo[5.4.0]undec-7-ene, tri-n-butylamine, and N-methylmorpholine; organic metal compounds such as methyllithium, ethyllithium, n-propyllithium, isopropyllithium, n-butyllithium, sec-butyllithium, tert-butyllithium, phenyllithium, methylmagnesium chloride, ethylmagnesium chloride, n-propylmagnesium chloride, isopropylmagnesium chloride, n-butylmagnesium chloride, sec-butylmagnesium chloride, tert-butylmagnesium chloride, phenylmagnesium chloride, methylmagnesium bromide, ethylmagnesium bromide, n-propylmagnesium bromide, isopropylmagnesium bromide, n-butylmagnesium bromide, sec-butylmagnesium bromide, tert-butylmagnesium bromide, and phenylmagnesium bromide; and quaternary ammonium salts.

The amount of such a basic substance used is appropriately selected from the range of generally 0.5 to 10.0 molar equivalents, and preferably 1.1 to 3 molar equivalents, based on the α-ionone as a mixture of optical isomers used as a raw material.

Esterification may be carried out in the presence of a solvent, as necessary. Examples of such a solvent include aliphatic hydrocarbons such as pentane, hexane, heptane, octane, decane, and cyclohexane; aromatic hydrocarbons such as benzene, toluene, and xylene; halogenated hydrocarbons such as dichloromethane, 1,2-dichloroethane, chloroform, carbon tetrachloride, and o-dichlorobenzene; ethers such as diethyl ether, diisopropyl ether, tert-butyl methyl ether, dimethoxyethane, ethylene glycol diethyl ether, tetrahydrofuran, 1,4-dioxane, 1,3-dioxolane, 2-methyltetrahydrofuran, and cyclopentyl methyl ether; ketones such as acetone, methyl ethyl ketone, methyl isobutyl ketone, and cyclohexanone; alcohols such as methanol, ethanol, 2-propanol, n-butanol, 2-ethoxyethanol, or benzyl alcohol; polyalcohols such as ethylene glycol, 1,2-propanediol, 1,3-propanediol, and glycerin; esters such as methyl acetate, ethyl acetate, n-butyl acetate, and methyl propionate; amides such as formamide, N,N-dimethylformamide, and N,N-dimethylacetamide; sulfoxides such as dimethyl sulfoxide; cyano-containing organic compounds such as acetonitrile; N-methylpyrrolidone; and water. Such solvents may be used appropriately singly or in combination of two or more thereof.

The amount of such a solvent used is different depending on the type of an esterification agent used, the type of the solvent used, etc. The amount of such a solvent used is appropriately selected from the range of generally 1 to 100 times the volume, and preferably 10 to 50 times the volume, based on the α-ionone as a mixture of optically isomers used as a raw material.

The reaction temperature is different depending on the type of an esterification agent used, the type of a solvent used, etc. Such reaction temperature is appropriately selected from the range generally from −75° C. to 50° C., and preferably from −40° C. to 0° C.

The reaction time is appropriately selected from the range generally from 0.5 to 20 hours, and preferably from 1 to 10 hours.

The α-ionone enol ester represented by the above formula (3) may be appropriately subjected to a post-treatment or the like, as necessary. The resultant may be purified or isolated, and it may be then subjected to hydrolysis.

Such a post-treatment may be carried out by any conventional means. Specific methods include, for example, solvent extraction, salting-out, crystallization, recrystallization, various types of chromatography, and the like.

Thus obtained α-ionone enol ester is hydrolyzed to give optically active α-ionone and/or an α-ionone enol ester.

Examples of a mixture of α-ionone and an α-ionone enol ester obtained by the enantioselective hydrolysis of the α-ionone enol ester include a mixture wherein only the α-ionone is an optically active substance; a mixture wherein only the α-ionone enol ester is an optically active substance; and a mixture wherein both the α-ionone and the α-ionone enol ester are optically active substances. There are the aforementioned cases, in the present invention, depending on the optical purity or chemical purity of the α-ionone enol ester used, and the optical purity or chemical purity of the α-ionone as a mixture of optical isomers used as a raw material.

Only optically active α-ionone can be substantially obtained by carrying out enantioselective hydrolysis. The term "substantially" is used to mean a case where one optical isomer is hardly contained in the other optical isomer. In the present invention, however, depending on the intended use of optically active α-ionone or the like, the term "substantially" also includes cases where one optical isomer is contained in the other optical isomer within a range that does not impair the properties thereof. Moreover, when only an α-ionone enol ester is optically active as well, the term "substantially" also includes cases where one optical isomer is contained in the other optical isomer within a range that does not impair the properties thereof, depending on the intended use of optically active α-ionone obtained by hydrolysis as described later.

When both the α-ionone and the α-ionone enol ester are optically active substances, if the α-ionone as a mixture of optical isomers used as a raw material is a racemic form, optically active α-ionone and an optically active α-ionone enol ester are theoretically obtained in equivalent amounts. However, there are also cases where such optically active α-ionone and such an optically active α-ionone enol ester are not necessarily obtained in equivalent amounts, depending on the reaction conditions for hydrolysis, the type of enzyme used, etc.

The obtained optically active α-ionone and/or optically active α-ionone enol ester are obtained in the form of a mixture. Thus, each of the optically active α-ionone and the optically active α-ionone enol ester is fractionated from the mixture, so that desired optically active α-ionone and/or a desired optically active α-ionone enol ester can be obtained.

The obtained optically active α-ionone has a higher optical purity than that of the α-ionone as a mixture of optical isomers used as a raw material. The term "higher optical purity" used in the present invention means that the optical purity of the obtained product is higher than that of a raw material (the same is applied below). In this case, it means that the obtained product has such an optical purity that a larger amount of (S) form or (R) form α-ionone is contained than that of the α-ionone as a mixture of optical isomers used as a raw material.

The optical purity of the obtained optically active α-ionone is appropriately selected from the range, for example, from 1% to 99% e.e., preferably from 5% to 99% e.e., and more preferably from 10% to 99% e.e. Otherwise, such an optical purity may also be substantially 100% e.e.

On the other hand, a remaining α-ionone enol ester, which has not been hydrolyzed, is obtained as a racemic form or an optically active substance, and preferably obtained as an optically active substance. When such an optically active α-ionone enol ester is obtained, it can be an enantiomer of the aforementioned hydrolyzed α-ionone enol ester. However, such an optically active substance may not be necessarily obtained in some cases, depending on the optical purity of α-ionone as a mixture of optical isomers used as a raw material.

The optical purity of the optically active α-ionone enol ester is higher than that of the α-ionone as a mixture of optical isomers used as a raw material. The optical purity of the obtained optically active α-ionone enol ester is appropriately selected from the range, for example, from 1% to 99% e.e., preferably from 5% to 99% e.e., and more preferably from 10% to 99% e.e. Otherwise, such an optical purity may also be substantially 100% e.e.

The enantioselective hydrolysis of an α-ionone enol ester includes a method of selectively hydrolyzing either one of optical isomers. For example, such a method is preferably carried out in the presence of enzyme. Such enzyme is preferably hydrolase. Examples of such hydrolase include carboxylesterase, allylesterase, cholinesterase, and lipase. Specific examples thereof include lipase derived from *Aspergillus niger*, lipase derived from *Mucor javanicus*, lipase derived from porcine pancreas, lipase derived from *Pseudomonas aeruginosa*, lipase derived from *Pseudomonas cepasia*, lipase derived from *Pseudomonas fluorescence*, lipase derived from *Rhizopus* sp., lipase derived from *Rhizomucor miehei*, lipase derived from *Caidida rugosa*, lipase derived from *Candida antarctica*, and esterase derived from porcine liver. Such hydrolases is more preferably lipase, and particularly further more preferably lipase derived from bacteria such as genus *Pseudomonas* and genus *Alcaligenes*, and lipase derived from *Candida antarctica*, etc. Moreover, a commercially available hydrolase can also be used as hydrolase used in the present invention. Examples of such a commercially available hydrolase that is preferably used herein include PS, PS-D, and PS-C (derived from genus *Pseudomonas*) manufactured by Amano Enzyme Inc.; AK-20 (derived from genus *Pseudomonas*) manufactured by Amano Enzyme Inc.; AH (derived from genus *Pseudomonas*) manufactured by Amano Enzyme Inc.; Lipase QL, QLC, and QLG (derived from genus *Alcaligenes*) manufactured by Meito Sangyo Co., Ltd.; and Novozym435 and NovozymCALB L manufactured by Novozymes. Such commercially available hydrolases can be directly used as it stands. In addition, enzymes used in the present invention may be used appropriately singly or in combination of two or more thereof.

Such enzymes may be directly added to a reaction solution at a time, or may also be dividedly and intermittently added to the reaction solution.

The amount of such enzyme used is appropriately selected from the range of generally 0.01% to 100% by mass (w/w), and preferably 0.1% to 50% by mass (w/w), based on the α-ionone enol ester.

The enantioselective hydrolysis carried out in the presence of enzyme may be carried out in the presence of a solvent, as necessary. Examples of such a solvent include hydrocarbons including aliphatic hydrocarbons such as pentane, hexane, heptane, octane, decane and cyclohexane, and aromatic hydrocarbons such as benzene, toluene and xylene; halogenated hydrocarbons such as dichloromethane, 1,2-dichloroethane, chloroform, carbon tetrachloride, and o-dichlorobenzene; ethers such as diethyl ether, diisopropyl ether, tert-butyl methyl ether, dimethoxyethane, ethylene glycol diethyl ether, tetrahydrofuran, 1,4-dioxane, and 1,3-dioxolane; ketones such as acetone, methyl ethyl ketone, methyl isobutyl ketone, and cyclohexanone; esters such as methyl acetate, ethyl acetate, n-butyl acetate, and methyl propionate; amides such as formamide, N,N-dimethylformamide, and N,N-dimethylacetamide; sulfoxides such as dimethyl sulfoxide; cyano-containing organic compounds such as acetonitrile; N-methylpyrrolidone; and water. Such solvents may be used appropriately singly or in combination of two or more thereof.

The amount of a solvent used is not particularly limited because it is different depending on the type of enzyme used, the used amount, etc. Such amount is appropriately selected from the range of generally 0.5 to 100 times the volume, and preferably 1 to 50 times the volume, based on the α-ionone enol ester used as a raw material.

The reaction temperature is not particularly limited because it is different depending on the type of enzyme used, the used amount, etc. Such reaction temperature is appropriately selected from the range generally between 0° C. and 70° C., and preferably between 10° C. and 50° C.

The reaction time is not particularly limited because it is different depending on the type of enzyme used, the used amount, etc. Such reaction time is appropriately selected from the range generally between 1 and 48 hours, and preferably between 3 and 24 hours.

On the other hand, as described above, a remaining α-ionone enol ester, which has not been hydrolyzed, is obtained as a racemic form or an optically active substance, and preferably obtained as an optically active α-ionone enol ester of an optically active substance. In this case, such an optically active α-ionone enol ester can be obtained as an enantiomer of the hydrolyzed optically active α-ionone enol ester. However, such an optically active substance may not be necessarily obtained in some cases, depending on the optical purity of α-ionone as a mixture of optical isomers used as a raw material.

More specifically, suitable enzyme is selected from among the aforementioned types of enzymes, and hydrolysis is carried out using the selected enzyme, so as to give the optically active α-ionone represented by the aforementioned formula (2), thereby obtaining the (S)-α-ionone represented by the aforementioned formula (2A) or the (R)-α-ionone represented by the aforementioned formula (2B), as described above. In the present invention, preferably, the (S)-α-ionone enol ester represented by the aforementioned formula (3A) as an (S) form is substantially hydrolyzed, so as to give the (S)-α-ionone represented by the aforementioned formula (2A), although it depends on the type of enzyme used, etc. In contrast, the (R)-α-ionone enol ester represented by the aforementioned formula (3B) as an (R) form does not substantially react with such enzyme. Thus, the obtained (R)-α-ionone enol ester represented by the aforementioned formula (3B) can be an enantiomer of the (S)-α-ionone enol ester represented by the aforementioned formula (3A) which has been hydrolyzed with enzyme.

Fractionation may be carried out by a conventional method. After completion of such fractionation, the resultant may be directly used, or may be appropriately subjected to the aforementioned post-treatment, as necessary.

After enantioselective hydrolysis conducted in the presence of enzyme, a mixture of optically active α-ionone and an α-ionone enol ester is obtained. Thereafter, the optically active α-ionone and the α-ionone enol ester are separately obtained, namely, they are fractionated from this mixture. The fractionated α-ionone enol ester is then hydrolyzed to give α-ionone, and preferably, a second optically active α-ionone that can be an enantiomer of the optically active α-ionone obtained by hydrolysis with enzyme.

In the present invention, more preferably, a mixture of the (S)-α-ionone represented by the aforementioned formula (2A) obtained by the aforementioned hydrolysis with enzyme and the enol ester of an (R)-α-ionone that is an enantiomer of the aforementioned (S)-α-ionone is subjected to fractionation. Thus fractionated (R)-α-ionone enol ester is then hydrolyzed, so as to give an (R)-α-ionone that is an enantiomer of the (S)-α-ionone represented by the aforementioned formula (2A).

When the second α-ionone is obtained in the form of an optically active substance, the obtained optically active α-ionone has a higher optical purity than that of the α-ionone as a mixture of optical isomers used as a raw material. The term "higher optical purity" is used herein to mean that the obtained product has such an optical purity that a larger amount of (S) form or (R) form α-ionone is contained than that of the α-ionone as a mixture of optical isomers used as a raw material.

The optical purity of the second optically active α-ionone is appropriately selected from the range, for example, from 1% to 99% e.e., preferably from 5% to 99% e.e., and more preferably from 10% to 99% e.e. Otherwise, such an optical purity may also be substantially 100% e.e. As described above, the obtained optically active α-ionone may be obtained in the form of a racemic form in some cases, depending on the type of an α-ionone as a mixture of optical isomers used as a raw material.

In order to obtain the second optically active α-ionone having a desired optical purity, the production method of the present invention may also be carried out repeatedly. By carrying out the present production method repeatedly, an optically active α-ionone having an optical purity of substantially 100% e.e. can be obtained.

In the present invention, such an optically active α-ionone may not be needed to have an optical purity of substantially 100% e.e., depending on the intended use or the like. In such a case, optically active α-ionone having an optical purity, for example, from 10% e.e. to 90% e.e., and preferably from 15% e.e. to 85% e.e. may be directly used. In addition, the optical purity of the obtained optically active α-ionone may also be adjusted, as appropriate, by altering reaction conditions and the like. Moreover, in order to obtain optically active α-ionone having a desired optical purity, the production method of the present invention may be carried out repeatedly. Otherwise, the obtained optically active α-ionone may be mixed with another type of α-ionone (for example, the optically active α-ionone obtained by the production method of the present invention, the α-ionone as a mixture of optical isomers, etc.).

The hydrolysis of fractionated α-ionone enol ester is preferably carried out under acidic or basic conditions.

Examples of an additive used under acidic or basic conditions include an acidic substance, a basic substance, salts with an acid used in the aforementioned acidic substance and a base used in the aforementioned basic substance, and a buffer agent.

Examples of an acidic substance include inorganic acid, organic acid, and Lewis acid.

Examples of inorganic acid include hydrochloric acid, hydrobromic acid, sulfuric acid, phosphoric acid, tetrafluoroboric acid, perchloric acid, and periodic acid.

Examples of organic acid include carboxylic acids such as formic acid, acetic acid, valeric acid, hexanoic acid, citric acid, chloroacetic acid, dichloroacetic acid, trichloroacetic acid, trifluoroacetic acid, benzoic acid, salicylic acid, oxalic acid, succinic acid, malonic acid, phthalic acid, tartaric acid, malic acid, and glycolic acid; and sulfonic acids such as methanesulfonic acid, benzenesulfonic acid, p-toluenesulfonic acid, and trifluoromethanesulfonic acid.

Examples of Lewis acid include aluminum halides such as aluminum chloride, and aluminum bromide; dialkyl aluminum halides such as diethyl aluminum chloride, diethyl aluminum bromide, and diisopropyl aluminum chloride; trialkoxy aluminums such as triethoxy aluminum, triisopropoxy aluminum, and tri-tert-butoxy aluminum; titanium halides such as titanium tetrachloride; tetraalkoxy titaniums such as tetraisopropoxy titanium; boron halides such as boron trifluoride, boron trichloride, boron tribromide, and a boron trifluoride-diethyl etherate; and zinc halides such as zinc chloride, and zinc bromide.

Examples of a basic substance are the same basic substance as described above.

Examples of a buffer agent include acetate buffer, Tris buffer, phosphate buffer, veronal buffer, borate buffer, and Good's buffer.

Such additives may be appropriately selected and used, depending on acidic conditions or basic conditions, which are conditions applied to hydrolysis.

The amount of such an additive used is appropriately selected from the range generally from 0.1 to 100 times the volume, and preferably from 1 to 50 times the volume, based on the α-ionone enol ester.

The fractionated α-ionone enol ester may be hydrolyzed in the presence of a solvent, as necessary. Examples of such a solvent used as necessary include aliphatic hydrocarbons such as pentane, hexane, heptane, octane, decane, and cyclohexane; aromatic hydrocarbons such as benzene, toluene, and xylene; halogenated hydrocarbons such as dichloromethane, 1,2-dichloroethane, chloroform, carbon tetrachloride, and o-dichlorobenzene; ethers such as diethyl ether, diisopropyl ether, tert-butyl methyl ether, dimethoxyethane, ethylene glycol diethyl ether, tetrahydrofuran, 1,4-dioxane, 1,3-dioxolane, 2-methyltetrahydrofuran, and cyclopentyl methyl ether; ketones such as acetone, methyl ethyl ketone, methyl isobutyl ketone, and cyclohexanone; alcohols such as methanol, ethanol, 2-propanol, n-butanol, 2-ethoxyethanol, and benzyl alcohol; polyalcohols such as ethylene glycol, 1,3-propanediol, 1,2-propanediol, and glycerin; esters such as methyl acetate, ethyl acetate, n-butyl acetate, and methyl propionate; amides such as formamide, N,N-dimethylformamide, and N,N-dimethylacetamide; sulfoxides such as dimethyl sulfoxide; cyano-containing organic compounds such as acetonitrile; N-methylpyrrolidone; and water. Such solvents may be used appropriately singly or in combination of two or more thereof.

The amount of such a solvent used is different depending on the type of an additive, the type of the solvent, etc. Such amount is appropriately selected from the range generally from 0.5 to 1000 times the volume, and preferably from 1 to 50 times the volume, based on the α-ionone enol ester.

The reaction temperature is different depending on the type of an additive used, the type of a solvent used, etc. Such reaction temperature is appropriately selected from the range generally from 0° C. and 100° C., and preferably from 10° C. and 50° C.

The reaction time is appropriately selected from the range generally from 0.5 and 10 hours, and preferably from 1 and 5 hours.

The obtained optically active α-ionone may be subjected to the aforementioned post-treatment or the like, as necessary.

Herein, with respect to said obtained α-ionone, when the aforementioned α-ionone as a mixture of optically active substances used as a raw material is an optically active substance, the aforementioned α-ionone enol ester has almost the same level of optical purity as that of said obtained α-ionone. In this case, if ordinary hydrolysis is carried out, the purity of the optically active α-ionone obtained by such hydrolysis improves. That is to say, the obtained optically active α-ionone is obtained a purified product from the optically active α-ionone used as a raw material.

The process for producing the optically active α-ionone of the present invention can also be carried out as follows:

First, α-ionone as a mixture of optical isomers is subjected to an asymmetric reduction to give optically active α-ionol. Subsequently, the obtained optically active α-ionol is allowed to react with an esterification agent to give an optically active α-ionol ester. Herein, the obtained optically active α-ionol ester may be a mixture of diastereomers in some cases. For example, if the α-ionone as a mixture of optical isomers used as a raw material is a racemic form, an asymmetric carbon atom at 1-position of a cyclohexene ring in the α-ionone skeleton is substantially a racemic form. In addition, if the aforementioned α-ionone is an optically active substance and the optical purity thereof is not 100% e.e., an asymmetric carbon atom at 1-position is optically active, and the optical purity thereof is at almost the same level as that of the α-ionone as a mixture of optical isomers used as a raw material. Moreover, the optical purity of a carton atom at 2-position in an optically active α-ionol ester, namely, the optical purity of a carbon atom at 2-position in the α-ionol skeleton (a carbon atom to which a hydroxy group binds; the same is applied below) is at almost the same level as the optical purity of an optically active α-ionol obtained by an asymmetric reduction of the α-ionone used as a raw material.

Subsequently at least one diastereomer of the obtained optically active α-ionol ester is purified, as necessary, so as to improve the optical purity of asymmetric carbon atoms at 2-position thereof and at 1-position of a cyclohexene ring. By such purification, at least one diastereomer of an ester body from a mixture of diastereomers is isolated and obtained. Thereafter, the optically active α-ionol ester obtained by such isolation is hydrolyzed to give optically active α-ionol. The obtained optically active α-ionol is then oxidized, so as to give desired optically active α-ionone. Herein, with regard to isolation of at least one diastereomer, the optical purity of the optically active α-ionol ester is not necessarily 100% e.e. The obtained optically active α-ionol ester may contain the other diastereomer or a compound other than the optically active α-ionol ester.

As α-ionone as a mixture of optical isomers that is to be subjected to an asymmetric reduction, the same α-ionone described above may be used. Such α-ionone may be either a racemic form or an optically active substance. In addition, the cis-trans ratio of the double bond at 2-position of the aforementioned α-ionone is also the same as described above. Moreover, when an optically active substance is used as α-ionone as a mixture of optical isomers, the optically active α-ionone obtained as described above may be used.

The α-ionol in the aforementioned optically active α-ionol is 4-(2,6,6-trimethyl-2-cyclohexen-1-yl)-3-buten-2-ol.

The optically active α-ionol obtained by an asymmetric reduction is represented by formula (6):

[Formula 13]

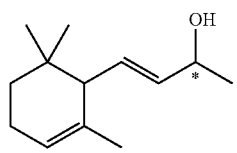

(6)

wherein * has the same meaning as described above.

Said optically active α-ionol represented by above formula (6) is (S)-α-ionol represented by formula (6A):

[Formula 14]

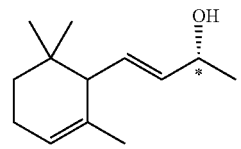

(6A)

wherein * has the same meaning as described above, or (R)-α-ionol represented by formula (6B):

[Formula 15]

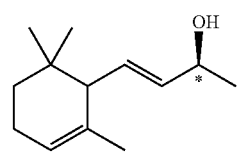

(6B)

wherein * has the same meaning as described above.

The optical purity of the asymmetric carbon atom at 2-position of the optically active α-ionol is appropriately selected from the range, for example, from 1% to 99% e.e., preferably from 5% to 99% e.e., and more preferably from 10% to 99% e.e. The aforementioned optical purity is used to mean the optical purity of the asymmetric carbon atom at 2-position of the optically active α-ionol. However, there may also be cases where the asymmetric carbon atom at 1-position of the cyclohexene ring is also included.

In addition, when the α-ionone as a mixture of optical isomers used as a raw material is an optically active substance, the aforementioned optically active α-ionol is obtained as an optically active α-ionol represented by formula (6C), wherein the carbon atom at 1-position of the cyclohexene ring thereof is an asymmetric carbon atom:

[Formula 16]

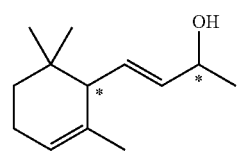

(6C)

wherein * has the same meaning as described above.

The aforementioned asymmetric reduction is carried out in the presence of a chiral catalyst. Moreover, in the present invention, the aforementioned asymmetric reduction is preferably an asymmetric hydrogenation.

Such an asymmetric hydrogenation is carried out in the presence of a hydrogen source. Examples of such a hydrogen source include hydrogen gas and a hydrogen donor.

That is to say, examples of the asymmetric hydrogenation used in the present invention include an asymmetric hydrogenation conducted in the presence of hydrogen gas and an asymmetric transfer hydrogenation conducted in the presence of a hydrogen donor.

A chiral catalyst is preferably a transition metal complex, more preferably a chiral transition metal complex. A transition metal complex that contains a transition metal and a chiral ligand is preferably used as the aforementioned chiral transition metal complex. Moreover, the chiral transition metal complex may be used to asymmetric hydrogenation in situ.

A transition metal used for a chiral transition metal complex is preferably a transition metal of the eighth group to the tenth group of a periodic table of the elements.

An example of such a chiral transition metal complex is a transition metal complex represented by the following formula (12) or (13):

$$M_mL_nX_pY_q \quad (12)$$

$$[M_mL_nX_pY_q]Z_s \quad (13)$$

In the above formulae, M represents a transition metal from the eight group to the tenth group of a periodic table of the elements; L represents a chiral ligand; X represents a halogen atom, a carboxylate group, an allyl group, 1,5-cyclooctadiene, or norbornadiene; Y represents a ligand; Z represents anion or cation; each of m and n independently represents an integer of 1 to 5; and each of p, q, and s independently represents an integer of 0 to 5.

Transition metals from the eight group to the tenth group of the periodic table of the elements, represented by M in the formulae (12) and (13), are same or different, and include ruthenium (Ru), rhodium (Rh), iridium (Ir), palladium (Rd), nickel (Ni), and the like.

Chiral ligands represented by L are same or different, and include a monodentate ligand, a bidentate ligand, and the like. A chiral ligand is preferably an optically active phosphorus ligand, and more preferably an optically active bidentate phosphorus ligand.

Such an optically active bidentate phosphorus ligand may have an optically active site in a molecule thereof. An example of such an optically active bidentate phosphorus ligand is a phosphorus compound represented by the following formula (14), wherein the compound has an optically active site in the following formula:

$$R^{11}R^{12}P-Q^1-PR^{13}R^{14} \quad (14)$$

wherein each of $R^{11}$ to $R^{14}$ independently represents an optionally substituted hydrocarbon group, an optionally substituted heterocyclic group, an optionally substituted alkoxy group, or an optionally substituted aryloxy group; $Q^1$ represents a spacer; and further, $R^{11}$ and $R^{12}$ and/or $R^{13}$ and $R^{14}$ may bond with each other to form a ring.

In the formula (14), optionally substituted hydrocarbon groups represented by $R^{11}$ to $R^{14}$ are the same as the aforementioned optionally substituted hydrocarbon group.

Examples of an optionally substituted heterocyclic group includes a heterocyclic group and a substituted heterocyclic group. Such a heterocyclic group includes an aliphatic heterocyclic group and an aromatic heterocyclic group.

An aliphatic heterocyclic group includes, for example, a 3- to 8-membered, and preferably 5- or 6-membered monocyclic, polycyclic or fused ring aliphatic heterocyclic group having 2 to 14 carbon atoms and containing at least one, and preferably 1 to 3 heteroatom(s) such as a nitrogen atom, an oxygen atom, and/or a sulfur atom. Specific examples of such an aliphatic heterocyclic group include pyrrolidyl-2-one, piperidyl, piperidino, piperazinyl, morpholino, morpholinyl, tetrahydrofuryl, tetrahydropyranyl, and thioranyl.

An aromatic heterocyclic group includes, for example, a 3- to 8-membered, and preferably 5- or 6-membered monocyclic, polycyclic, or fused ring aromatic heterocyclic group having 2 to 15 carbon atoms and containing at least one, and preferably 1 to 3 heteroatom(s) such as a nitrogen atom, an oxygen atom, and/or a sulfur atom. Specific examples of such an aromatic heterocyclic group include furyl, thienyl, pyridyl, pyrimidyl, pyrazyl, pyridazinyl, pyrazolyl, imidazolyl, oxazolyl, thiazolyl, benzofuryl, benzothienyl, quinolyl, isoquinolyl, quinoxalinyl, phthalazinyl, quinazolinyl, naphthylidinyl, cinnolinyl, benzoimidazolyl, benzoxazolyl, benzothiazolyl, and acrydinyl.

A substituted heterocyclic group [a heterocyclic group having a substituent(s)] includes a heterocyclic group wherein at least one hydrogen atom of the aforementioned heterocyclic groups is substituted with the aforementioned substituent, namely, a substituted aliphatic heterocyclic group and a substituted aromatic heterocyclic group.

An optionally substituted alkoxy group includes an alkoxy group and a substituted alkoxy group.

Such an alkoxy group includes, for example, a linear, branched, or cyclic alkoxy group having 1 to 20 carbon atom(s). Specific examples thereof include methoxy, ethoxy, n-propoxy, 2-propoxy, n-butoxy, 2-butoxy, isobutoxy, tert-butoxy, n-pentyloxy, 2-methylbutoxy, 3-methylbutoxy, 2,2-dimethylpropyloxy, n-hexyloxy, 2-methylpentyloxy, 3-methylpentyloxy, 4-methylpentyloxy, heptyloxy, octyloxy, nonyloxy, decyloxy, and cyclohexyloxy. The aforementioned alkoxy group is preferably an alkoxy group having 1 to 10 carbon atom(s).

A substituted alkoxy group [an alkoxy group having a substituent(s)] includes an alkoxy group wherein at least one hydrogen atom of the aforementioned alkoxy group is substituted with the aforementioned substituent.

An optionally substituted aryloxy group includes an aryloxy group and a substituted aryloxy group.

Such an aryloxy group includes, for example, an aryloxy group having 6 to 20 carbon atoms. Specific examples thereof include phenyloxy, naphthyloxy, and anthryloxy. The aforementioned aryloxy group is preferably an aryloxy group having 6 to 14 carbon atoms.

A substituted aryloxy group [an aryloxy group having a substituent(s)] includes an aryloxy group wherein at least one hydrogen atom of the aforementioned aryloxy group is substituted with the aforementioned substituent.

A spacer represented by $Q^1$ includes an optionally substituted divalent organic group such as an alkylene group, an arylene group, and a heteroarylene group and the like. In addition, the aforementioned divalent organic group may have at least one heteroatom or an atomic group, such as an oxygen atom, a carbonyl group, a sulfur atom, an imino group, and a substituted imino group, at an arbitrary position of the terminal position or in the chain of the aforementioned organic group. A substituent in a substituted imino group includes the aforementioned optionally substituted hydrocarbon group, and the aforementioned optionally substituted heterocyclic group. Moreover, the aforementioned divalent organic group may be substituted with the aforementioned substituent(s).

An alkylene group includes, for example, an alkylene group having 1 to 10 carbon atom(s). Specific examples thereof include methylene, ethylene, trimethylene, tetramethylene, pentamethylene, hexamethylene, heptamethylene, octamethylene, nonamethylene, decamethylene, and propylene.

An arylene group includes, for example, an arylene group having 6 to 20 carbon atoms. Specific examples thereof include phenylene, biphenyldiyl, binaphthalendiyl, and bis-benzodioxoldiyl.

An heteroarylene group includes, for example, a 3- to 8-membered, and preferably 5- or 6-membered monocyclic, polycyclic, or fused ring heteroarylene group having 2 to 20 carbon atoms and containing at least one, and preferably 1 to 3 heteroatom(s) such as a nitrogen atom, an oxygen atom, and/or a sulfur atom. Specific examples thereof include bipyridinediyl, bisbenzothioldiyl, and bisthioldiyl.

Examples of a divalent organic group having a heteroatom or an atomic group include —$CH_2$—O—$CH_2$— and —$C_6H_4$—O—$C_6H_4$—.

Such divalent organic groups may be substituted with the substituent(s) as described later.

Furthermore, when a spacer has an optically active site(s), specific examples of such a spacer having an optically active site(s) include 1,2-dimethylethylene, 1,2-cyclohexylene, 1,2-diphenylethylene, 1,2-di(4-methylphenyl)ethylene, 1,2-dicyclohexylethylene, 1,3-dioxolan-4,5-diyl, biphenyldiyl, and binaphthalendiyl. Examples of such a spacer having an optically active site(s) include an (R) form, an (S) form, an (R,R) form, and an (S,S) form.

An example of the case where $R^{11}$ and $R^{12}$ and/or $R^{13}$ and $R^{14}$ bond with each other to form a ring is a case of bonding through, for example, an alkylene group to form a phosphorus-containing ring. Such an alkylene group includes, for example, a linear or branched alkylene group having 1 to 6 carbon atom(s). Specific examples of such an alkylene group include ethylene, propylene, trimethylene, 2-methylpropylene, 2,2-dimethylpropylene, and 2-ethylpropylene. Specific examples of the formed ring include a phosphorane ring and a 2,5-dimethylphosphorane ring.

Specific examples of an optically active phosphorus compound include optically active substances such as 1,2-bis(anisylphenylphosphino)ethane (DIPAMP), 1,2-bis(alkylmethylphosphino)ethane (BisP*), 2,3-bis(diphenylphosphino) butane (CHIRAPHOS), 1,2-bis(diphenylphosphino)propane (PROPHOS), 2,3-bis(diphenylphosphino)-5-norbornene (NORPHOS), 2,3-O-isopropylidene-2,3-dihydroxy-1,4-bis(diphenylphosphino)butane (DIOP), 1-cyclohexyl-1,2-bis(diphenylphosphino)ethane (CYCPHOS), 1-substituted-3,4-bis(diphenylphosphino)pyrrolidine (DEGPHOS), 2,4-bis(diphenylphosphino)pentane (SKEWPHOS), 1,2-bis(substituted phosphorano)benzene (DuPHOS), 1,2-bis(substituted phosphorano)ethane (BPE), 1-((substituted phosphorano)-2-(diphenylphosphino)benzene (UCAP-Ph), 1-(bis(3,5-dimethylphenyl)phosphino)-2-(substituted phosphorano)benzene (UCAP-DM), 1-((substituted phosphorano)-2-(bis(3,5-di(t-butyl)-4-methoxyphenyl)phosphino) benzene (UCAP-DTBM), 1-((substituted phosphorano)-2-(di-naphthalene-1-yl-phosphino)benzene (UCAP-(1-Nap)), 2,2'-bis(diphenylphosphino)-1,1'-bicyclopentane (BICP), 2,2'-bis(diphenylphosphino)-1,1'-binaphthyl (BINAP), 2,2'-bis(diphenylphosphino)-1,1'-(5,5',6,6',7,7',8,8'-octahydrobinaphthyl) ($H_8$-BINAP), 2,2'-bis(di-p-tolylphosphino)-1,1'-binaphthyl (TOL-BINAP), 2,2'-bis(di(3,5-dimethylphenyl) phosphino)-1,1'-binaphthyl (DM-BINAP), 2,2'-bis(diphenylphosphino)-6,6'-dimethyl-1,1'-biphenyl (BICHEP), (4,4'-bi-1,3-benzodioxol)-5,5'-diylbis(diphenylphosphine) (SEGPHOS), (4,4'-bi-1,3-benzodioxol)-5,5'-diylbis[bis(3,5-dimethylphenyl)phosphine] (DM-SEGPHOS), and [(4S)-[4,4'-bi-1,3-benzodioxol]-5,5'-diyl]bis[bis[3,5-bis(1,1-dimethylethyl)-4-methoxyphenyl]phosphine] (DTBM-SEGPHOS).

As a chiral ligand, in addition to the aforementioned optically active bidentate phosphine ligands, a bisheterocyclic compound and the like can also be used.

Examples of ligands represented by Y are same or different, and include neutral ligands such as an aromatic compound, and an olefinic compound; amines, and the like.

Examples of such an aromatic compound include benzene, p-cymene, 1,3,5-trimethylbenzene (mesitylene), and hexamethylbenzene. Examples of such an olefinic compound include ethylene, 1,5-cyclooctadiene, cyclopentadiene, and norbornadiene. Examples of other neutral ligands include N,N-dimethylformamide (DMF), acetonitrile, benzonitrile, acetone, and chloroform.

Examples of amines include diamines including aromatic diamines and aliphatic diamines such as 1,2-diphenylethylenediamine (DPEN), 1,2-diaminocyclohexane, ethylenediamine, 1,1-bis(4-methoxyphenyl)-2-isopropylethylenediamine (DAIPEN), 1,2-bis(4-methoxyphenyl) ethylenediamine, 1,2-dicyclohexylethylenediamine, 1,2-di(4-N,N-dimethylaminophenyl)ethylenediamine, 1,2-di(4-N,N-diethylaminophenyl)ethylenediamine, 1,2-di(4-N,N-dipropylaminophenyl)ethylenediamine, 1,2-(N-benzenesulfonyl)-1,2-di(4-N,N-dimethylaminophenyl) ethylenediamine, 1,2-(N-p-toluenesulfonyl)-1,2-di(4-N,N-dimethylaminophenyl)ethylenediamine, 1,2-(N-methanesulfonyl)-1,2-di(4-N,N-dimethylaminophenyl) ethylenediamine, 1,2-(N-trifluoromethanesulfonyl)-1,2-di (4-N,N-dimethylaminophenyl)ethylenediamine, 1,2-(N-benzenesulfonyl)-1,2-di(4-N,N-diethylaminophenyl) ethylenediamine, 1,2-(N-benzenesulfonyl)-1,2-di(4-N,N-dipropylaminophenyl)ethylenediamine,1,2-di(4-sulfonylphenyl)ethylenediamine, 1,2-di(4-sodiumoxysulfonylphenyl)ethylenediamine, 1,2-cyclohexanediamine, 1,2-cycloheptanediamine, 2,3-dimethylbutanediamine, 1-methyl-2,2-diphenylethylenediamine, 1-isobutyl-2,2-diphenylethylenediamine, 1-isopropyl-2,2-diphenylethylenediamine, 1-methyl-2,2-di(p-methoxyphenyl)ethylenediamine, 1-isobutyl-2,2-di(p-methoxyphenyl)ethylenediamine, 1-isopropyl-2,2-di(p-methoxyphenyl)ethylenediamine, 1-benzyl-2,2-di(p-methoxyphenyl)ethylenediamine, 1-methyl-2,2-dinaphthylethylenediamine, 1-isobutyl-2,2-dinaphthylethylenediamine, 1-isopropyl-2,2-dinaphthylethylenediamine, bis[N-(2,4,6-trimethylphenyl) methyl-1,2-diphenylethylenediamine, N,N'-bis(phenylmethyl)-1,2-diphenyl-1,2-ethylenediamine, N,N'-bis(mesitylmethyl)-1,2-diphenyl-1,2-ethylenediamine, and N,N'-bis(naphthylmethyl)-1,2-diphenyl-1,2-ethylenediamine; aliphatic amines including trialkylamine such as triethylamine; and aromatic amines such as pyridine.

When an asymmetric transfer hydrogenation is carried out as an asymmetric hydrogenation, such amines are preferable optically active substances, and more preferably optically active diamine compounds such as optically active aromatic diamines and optically active aliphatic diamines.

Examples of a halogen atom represented by X include a chlorine atom, a bromine atom, and an iodine atom.

In formula (13), examples of anion represented by Z include $BF_4$, $ClO_4$, OTf, $NO_3$, $PF_6$, $SbF_6$, $AsF_6$, $BPh_4$, $BH_4$, $BF_4$, Cl, Br, I, $I_3$, and sulfonate. Herein, Tf represents a triflate group ($SO_2CF_3$).

Examples of cation is represented, by formula (15):

$$[(R^{15})_2NH_2]^+ \tag{15}$$

wherein two $R^{15}$ are same or different, and represent a hydrogen atom or an optionally substituted hydrocarbon group.

In the formula (15), the optionally substituted hydrocarbon group represented by $R^{15}$ is the same as the aforementioned optionally substituted hydrocarbon group. Such optionally substituted hydrocarbon group represented by $R^{15}$ is preferably an alkyl group having 1 to 5 carbon atom(s), a cycloalkyl group, an optionally substituted phenyl group, an optionally substituted benzyl group, and the like.

Specific examples of cation include $[Me_2NH_2]^+$, $[Et_2NH_2]^+$, and $[Pr_2NH_2]^+$.

A preferred embodiment of the aforementioned transition metal complex will be described below.

[1] Formula (12):

$$M_mL_nX_pY_q \quad (12)$$

1) When M is Ir or Rh, X is Cl, Br or I. When L is a monodentate ligand, m=p=2, n=4, and q=0. When L is a bidentate ligand, m=n=p=2, and q=0.
2) When M is Ru, (i) X is Cl, Br or I, and Y is trialkylamine. When L is a monodentate ligand, m=2, n=p=4, and q=1. When L is a bidentate ligand, m=n=2, p=4, and q=1.
   (ii) X is Cl, Br or I, and Y is a pyridyl group or a ring-substituted pyridyl group. When L is a monodentate ligand, m=1, n=p=2, and q=2. When L is a bidentate ligand, m=n=1, p=2, and q=2.
   (iii) X is a carboxylate group. When L is a monodentate ligand, m=1, n=p=2, and q=0. When L is a bidentate ligand, m=n=1, p=2, and q=0.
   (iv) X is Cl, Br or I. When L is a monodentate ligand, m=p=2, n=4, and q=0. When L is a bidentate ligand, m=n=p=2, and q=0.
3) When M is Pd, (i) X is Cl, Br or I. When L is a monodentate ligand, m=1, n=2, p=2, and q=0. When L is a bidentate ligand, m=n=1, p=2, and q=0.
   (ii) X is an allyl group. When L is a monodentate ligand, m=p=2, n=4, and q=0. When L is a bidentate ligand, m=n=p=2, and q=0.
4) When M is Ni, (i) X is Cl, Br or I. When L is a monodentate ligand, m=1, n=2, p=2, and q=0. When L is a bidentate ligand, m=n=1, p=2, and q=0.

[2] Formula (13)

$$[M_mL_nX_pY_q]Z_s \quad (13)$$

1) When M is Ir or Rh, X is 1,5-cyclooctadiene or norbornadiene; Z is $BF_4$, $ClO_4$, OTf, $PF_6$, $SbF_6$, or $BPh_4$; and m=n=p=s=1, and q=0, or m=s=1, n=2, and p=q=0.
2) When M is Ru, (i) X is Cl, Br or I; Y is a neutral ligand such as an aromatic compound and an olefinic compound; and Z is Cl, Br, I, $I_3$ or sulfonate. When L is a monodentate ligand, m=p=s=q=1, and n=2. When L is a bidentate ligand, m=n=p=s=q=1.
   (ii) When Z is $BF_4$, $ClO_4$, OTf, $PF_6$, $SbF_6$ or $BPh_4$, and L is a monodentate ligand, m=1, n=2, p=q=0, and s=2. When L is a bidentate ligand, m=n=1, p=q=0, and s=2.
   (iii) When Z is an ammonium ion, and L is a bidentate ligand, m=2, n=2, p=5, and q=0.
3) When M is Pd and Ni, Z is $BF_4$, $ClO_4$, OTf, $PF_6$, $SbF_6$ or $BPh_4$. (i) When L is a monodentate ligand, m=1, n=2, p=q=0, and s=2. (ii) When L is a bidentate ligand, m=n=1, p=q=0, and s=2.

The aforementioned transition metal complex used in the present invention can be produced by a known method. For example, it can be obtained by allowing a chiral ligand to react with a transition metal complex precursor.

The expression "obtained by allowing . . . to react . . . " is used herein to mean a transition metal complex obtained by performing a post-treatment or the like, as necessary, a transition metal complex isolated and/or purified after performing a post-treatment or the like, a transition metal complex obtained by direct use of a reaction mixture without performing a post-treatment, isolation, purification, or the like, etc.

An example of such a transition metal complex precursor is the transition metal complex precursor represented by formula (16):

$$[MX_pY_q]Z_s \quad (16)$$

wherein M, X, Y, Z, p, q, and s have the same meanings as described above.

Specific examples of the transition metal complex precursor represented by the above formula (7) used in the present invention, wherein, in the above formula (7), the transition metal represented by M is ruthenium, rhodium, and iridium, include, for example, $[RuCl_2(benzene)]_2$, $[RuBr_2(benzene)]_2$, $[RuI_2(benzene)]_2$, $[RuCl_2(p\text{-}cymene)]_2$, $[RuBr_2(p\text{-}cymene)]_2$, $[RuI_2(p\text{-}cymene)]_2$, $[RuCl_2(hexamethylbenzene)]_2$, $[RuBr_2(hexamethylbenzene)]_2$, $[RuI_2(hexamethylbenzene)]_2$, $[RuCl_2(mesitylene)]_2$, $[RuBr_2(mesitylene)]_2$, $[RuI_2(mesitylene)]_2$, $[RuCl_2(pentamethylcyclopentadiene)]_2$, $[RuBr_2(pentamethylcyclopentadiene)]_2$, $[RuI_2(pentamethylcyclopentadiene)]_2$, $[RuCl_2(cod)]_n$, $[RuBr_2(cod)]_n$, $[RuI_2(cod)]_n$, $[RuCl_2(nbd)]_n$, $[RuBr_2(nbd)]_n$, $[RuI_2(nbd)]_n$, $RuCl_3$ hydrate, $RuBr_3$ hydrate, $RuI_3$ hydrate, $[RhCl_2(cyclopentadiene)]_2$, $[RhBr_2(cyclopentadiene)]_2$, $[RhI_2(cyclopentadiene)]_2$, $[RhCl_2(pentamethylcyclopentadiene)]_2$, $[RhBr_2(pentamethylcyclopentadiene)]_2$, $[RhI_2(pentamethylcyclopentadiene)]_2$, $[RhCl_2(cod)]_n$, $[RhBr_2(cod)]_n$, $[RhI_2(cod)]_n$, $[RhCl_2(nbd)]_n$, $[RhBr_2(nbd)]_n$, $[RhI_2(nbd)]_n$, $[Rh(cod)_2]SbF_6$, $RhCl_3$ hydrate, $RhBr_3$ hydrate, $RhI_3$ hydrate, $[IrCl_2(cyclopentadiene)]_2$, $[IrBr_2(cyclopentadiene)]_2$, $[IrI_2(cyclopentadiene)]_2$, $[IrCl_2(pentamethylcyclopentadiene)]_2$, $[IrBr_2(pentamethylcyclopentadiene)]_2$, $[IrI_2(pentamethylcyclopentadiene)]_2$, $[IrCl_2(cod)]_n$, $[IrBr_2(cod)]_n$, $[IrI_2(cod)]_n$, $[IrCl_2(nbd)]_n$, $[IrBr_2(nbd)]_n$, $[IrI_2(nbd)]_n$, $IrCl_3$ hydrate, $IrBr_3$ hydrate, and $IrI_3$ hydrate. Provided that, in the above formulae, n represents a positive number, cod represents 1,5-cyclooctadiene, and nbd represents norbornadiene, respectively.

A method for producing a transition metal complex used in the present invention will be specifically described below. With regard to symbols used in the formulae of transition metal complexes as described below, L represents a chiral ligand, Tf represents a triflate group ($SO_2CF_3$), Ph represents a phenyl group, and Ac represents an acetyl group, respectively. In addition, in order to avoid complexity, only bidentate ligands are exemplified as specific examples of chiral ligands.

Rhodium Complexes:

A rhodium complex can be produced according to, for example, the method described in "The Forth Series of Experimental Chemistry ($4^{th}$ Edition, Jikken Kagaku Koza)" edited by The Chemical Society of Japan, vol. 18, Yuuki Kinzoku Sakutai (Organometalic Complexes), pp. 339-344, 1991, (Maruzen). Specifically, such a rhodium complex can be obtained by allowing bis(cycloocta-1,5-diene)rhodium (I) tetrafluoroborate to react with a chiral ligand.

Specific examples of such a rhodium complex include complexes as follows:
$[Rh(L)Cl]_2$, $[Rh(L)Br]_2$, $[Rh(L)I]_2$, $[Rh(cod)(L)]BF_4$, $[Rh(cod)(L)]ClO_4$, $[Rh(cod)(L)]PF_6$, $[Rh(cod)(L)]BPh_4$, $[Rh(cod)(L)]OTf$, $[Rh(nbd)(L)]BF_4$, $[Rh(nbd)(L)]ClO_4$, $[Rh(nbd)(L)]PF_6$, $[Rh(nbd)(L)]BPh_4$, $[Rh(nbd)(L)]OTf$, $[Rh(L)_2]ClO_4$, $[Rh(L)_2]PF_6$, $[Rh(L)_2]OTf$, $[Rh(L)_2]BF_4$.

Ruthenium Complexes:

A ruthenium complex can be obtained according to, for example, the method described in T. Ikariya et al., J. Chem. Soc., Chem. Commun., 922 (1985), etc. Specifically, such a ruthenium complex can be obtained by heating under reflux and allowing [Ru(cod)Cl$_2$]$_n$ to react with a chiral ligand in the presence of triethylamine in a toluene solvent. In addition, it can also be obtained by the method described in K. Mashima et al., J. Chem. Soc., Chem. Commun., 1989, 1208, etc. Specifically, a ruthenium complex can be obtained by heating with stirring [Ru(p-cymene)I$_2$]$_2$ and a chiral ligand in dichloromethane and ethanol.

Specific examples of such a ruthenium complex include complexes as follows:
Ru(OAc)$_2$(L), Ru$_2$Cl$_4$(L)$_2$NEt$_3$, [RuCl(benzene)(L)]Cl, [RuBr(benzene)(L)]Br, [RuI(benzene)(L)]I, [RuCl(p-cymene)(L)]Cl, [RuBr(p-cymene)(L)]Br, [RuI(p-cymene)(L)]I, [Ru(L)](BF$_4$)$_2$, [Ru(L)](ClO$_4$)$_2$, [Ru(L)](PF$_6$)$_2$, [Ru(L)](BPh$_4$)$_2$, [Ru(L)](OTf)$_2$, Ru(OCOCF$_3$)$_2$(L), [{RuCl(L)$_2$}(μ-Cl)$_3$][Me$_2$NH$_2$], [{RuCl(L)}$_2$(μ-Cl)$_3$][Et$_2$NH$_2$], [{RuBr(L)$_2$}(μ-Cl)$_3$][Me$_2$NH$_2$], [{RuBr(L)$_2$}(μ-Cl)$_3$][Et$_2$NH$_2$], RuCl$_2$(L), RuBr$_2$(L), RuBr$_2$(L), RuCl$_2$(L)(diamine), RuBr$_2$(L)(diamine), RuI$_2$(L)(diamine), [{RuI(L)}$_2$(μ-I)$_3$][Me$_2$NH$_2$], [{RuI(L)}$_2$(μ-I)$_3$][Et$_2$NH$_2$], RuCl$_2$(L)(pyridine), RuBr$_2$(L)(pyridine), RuI$_2$(L)(pyridine).

Iridium Complexes:

An iridium complex can be obtained according to, for example, the method described in K. Mashima et al., J. Organomet. Chem., 428, 213 (1992), etc. Specifically, such an iridium complex can be obtained by allowing a chiral ligand to react with [Ir(cod)(CH$_3$CN)$_2$]BF$_4$ by stirring in tetrahydrofuran.

Specific examples of such an iridium complex include complexes as follows:
[Ir(L)Cl]$_2$, [Ir(L)Br]$_2$, [Ir(L)I]$_2$, [Ir(cod)(L)]BF$_4$, [Ir(cod)(L)]ClO$_4$, [Ir(cod)(L)]PF$_6$, [Ir(cod)(L)]BPh$_4$, [Ir(cod)(L)]OTf, [Ir(nbd)(L)]BF$_4$, [Ir(nbd)(L)]ClO$_4$, [Ir(nbd)(L)]PF$_6$, [Ir(nbd)(L)]BPh$_4$, [Ir(nbd)(L)]OTf.

Palladium Complexes:

A palladium complex can be obtained according to, for example, the method described in Y. Uozumi et al., J. Am. Chem. Soc., 9887 (1991), etc. Specifically, such a palladium complex can be obtained by allowing a chiral ligand to react with π-allyl palladium chloride.

Specific examples of such a palladium complex include complexes as follows:
PdCl$_2$(L), (π-allyl)Pd(L), [(Pd(L)]BF$_4$, [(Pd(L)]ClO$_4$, [(Pd(L)]PF$_6$, [(Pd(L)]BPh$_4$, [(Pd(L)]OTf.

Nickel Complexes:

A nickel complex can be obtained according to, for example, the method described in "The Forth Series of Experimental Chemistry (4$^{th}$ Edition, Jikken Kagaku Koza)" edited by The Chemical Society of Japan, vol. 18, Yuuki Kinzoku Sakutai (Organometalic Complexes), p. 376, 1991, (Maruzen). In addition, it can also be obtained by dissolving a chiral ligand and nickel chloride in a mixed solvent of 2-propanol and methanol and then heating them with stirring according to the method described in Y. Uozumi et al., J. Am. Chem. Soc., 113, 9887 (1991), etc.

Specific examples of such a nickel complex include complexes as follows:
NiCl$_2$(L), NiBr$_2$(L), NiI$_2$(L).

The aforementioned transition metal complexes to be used may be either commercially available products or appropriately produced complexes.

Moreover, as such a transition metal complex used in the present invention, a chiral ligand may be mixed with a transition metal complex precursor, and the obtained mixture may be directly used in an asymmetric hydrogenation without performing isolation or purification. This is what is called an asymmetric hydrogenation carrying out in situ.

The amount of a chiral catalyst used differs depending on the used α-ionone as a mixture of optical isomers, the used reactor, a reaction type, economical efficiency, etc. The amount of such a chiral catalyst is appropriately selected from the range generally from 1/10 to 1/100,000 by molar ratio, and preferably from 1/50 to 1/10,000 by molar ratio, based on the α-ionone as a mixture of optical isomers.

When an asymmetric hydrogenation is carried out as an asymmetric reduction in the presence of hydrogen gas, any pressure of the hydrogen gas may be employed so long as the reaction is carried out under a hydrogen atmosphere, or a hydrogen pressure of 0.1 MPa may also be sufficient. In consideration of economic efficiency, however, the pressure of the hydrogen gas is appropriately selected from the range generally from 0.1 to 20 MPa, and preferably from 0.2 to 10 MPa. Further, it is possible to maintain a high activity even at 1 MPa or less in consideration of economic efficiency.

When an asymmetric hydrogenation is carried out as an asymmetric reduction in the presence of a hydrogen donor, examples of such a hydrogen donor include an organic compound and/or an inorganic compound. Any type of hydrogen donor compound can be used, as long as it is a compound capable of donating hydrogen as a result of a thermal action or a catalytic action in a reaction system.

Examples of such a hydrogen donor include formic acid or salts thereof, the combined use of formic acid with a base, hydroquinone, cyclohexadiene, phosphorous acid, and alcohols. Of these, formic acid or salts thereof, the combined use of formic acid with a base, and alcohols are particularly preferable.

Examples of the salts of formic acid in the aforementioned formic acid or salts thereof include metal salts of formic acid such as an alkali metal salts of formic acid and an alkaline-earth metal salts of formic acid, ammonium salts, and substituted amine salts.

Examples of the aforementioned combined use of formic acid with a base include a combined use wherein formic acid can be converted to the salts of formic acid in a reaction system; and a combined use wherein formic acid can be substantially converted to the salts of formic acid.

Examples of a base that forms the metal salts of formic acid such as the alkali metal salts of formic acid and the alkaline-earth metal salts of formic acid, ammonium salts, substituted amine salts, etc., and a base used in combination of formic acid, include ammonia, an inorganic base, and an organic base.

Examples of an alkali metal that forms salts together with formic acid include lithium, sodium, potassium, rubidium, and caesium. Examples of an alkaline earth metal include magnesium, calcium, strontium, and barium.

Examples of an inorganic base include alkali or alkaline-earth metal salts such as potassium carbonate, potassium hydroxide, lithium hydroxide, sodium hydrogencarbonate, sodium carbonate, potassium hydrogencarbonate, sodium hydroxide, magnesium carbonate, and calcium carbonate; and metal hydrides such as sodium hydride.

Examples of an organic base include alkali metal alkoxides such as potassium methoxide, sodium methoxide, lithium methoxide, sodium ethoxide, potassium isopropoxide, lithium tert-butoxide, sodium tert-butoxide, and potassium tert-butoxide; the acetates of alkali or alkaline-earth metals, such as sodium acetate, potassium acetate, magnesium acetate, and calcium acetate; organic amines such as triethylamine, diisopropylethylamine, N,N-dimethylaniline, piperidine, pyridine, 4-dimethylaminopyridine, 1,5-diazabicyclo[4.3.0]non-5-ene, 1,8-diazabicyclo[5.4.0]undec-7-ene, tri-n-butylamine, and N-methylmorpholine; organic metal compounds such as methylmagnesium bromide, ethylmagnesium bromide, propylmagnesium bromide, tert-butylmagnesium chloride, tert-butylmagnesium bromide, methyllithium, ethyllithium, propyllithium, n-butyllithium, and tert-butyllithium; and quaternary ammonium salts.

Examples of alcohols used as hydrogen donors are preferably lower alcohols having a hydrogen atom at α-position. Specific examples include methanol, ethanol, n-propanol, isopropanol, n-butanol, and sec-butanol. Of these, isopropanol is preferable.

The amount of a hydrogen donor used is appropriately selected from the range generally from 0.1 to 100 equivalents, and preferably from 0.5 to 20 equivalents, based on the α-ionone as a mixture of optical isomers.

An asymmetric reduction can be carried out in a solvent, as necessary. Examples of such a solvent include aromatic hydrocarbons such as benzene, toluene, and xylene; aliphatic hydrocarbons such as pentane, hexane, heptane, and octane; halogenated hydrocarbons such as dichloromethane, chloroform, carbon tetrachloride, and dichloroethane; ethers such as diethyl ether, diisopropyl ether, tert-butyl methyl ether, cyclopentyl methyl ether, dimethoxyethane, tetrahydrofuran, dioxane, and dioxolane; alcohols such as methanol, ethanol, 2-propanol, n-butanol, tert-butanol, and benzyl alcohol; polyalcohols such as ethylene glycol, 1,2-propanediol, 1,3-propanediol, and glycerin; amides such as N,N-dimethylformamide, and N,N-dimethylacetamide; ketones such as acetone, and methyl isobutyl ketone; esters such as methyl acetate, ethyl acetate, and butyl acetate; acetonitrile; N-methylpyrrolidone; dimethyl sulfoxide; and water. Such solvents may be used appropriately singly or in combination of two or more thereof.

The amount of such a solvent used is different depending on the type of α-ionone as a mixture of optical isomers or economical efficiency. When an alcohol is used as such a solvent, for example, depending on the type of α-ionone as a mixture of optical isomers used, the solvent can be used in a low concentration of 1% or less, or without using such solvents, or in a state where almost no solvents are used. The amount of such a solvent used may be appropriately selected, such that the concentration of the α-ionone as a mixture of optical isomers can be in the range generally from 5% to 50% by mass, and preferably 10% to 40% by mass.

An asymmetric reduction can be carried out in the presence of an additive, as necessary. Examples of such an additive include an acid, a fluorine-containing alcohol, a base, a quaternary ammonium salt, a quaternary phosphonium salt, a halogen, and a reducing agent.

Examples of an acid include inorganic acid, organic acid, and Lewis acid.

Examples of inorganic acid include hydrochloric acid, hydrobromic acid, sulfuric acid, phosphoric acid, tetrafluoroboric acid, perchloric acid, and periodic acid.

Examples of organic acid include carboxylic acids such as formic acid, acetic acid, valeric acid, hexanoic acid, citric acid, chloroacetic acid, dichloroacetic acid, trichloroacetic acid, trifluoroacetic acid, benzoic acid, salicylic acid, oxalic acid, succinic acid, malonic acid, phthalic acid, tartaric acid, malic acid, and glycolic acid; and sulfonic acids such as methanesulfonic acid, benzenesulfonic acid, p-toluenesulfonic acid, and trifluoromethanesulfonic acid.

Examples of Lewis acid include aluminum halides such as aluminum chloride, and aluminum bromide; dialkyl aluminum halides such as diethyl aluminum chloride, diethyl aluminum bromide, and diisopropyl aluminum chloride; trialkoxy aluminums such as triethoxy aluminum, triisopropoxy aluminum, and tri-tert-butoxy aluminum; titanium halides such as titanium tetrachloride; tetraalkoxy titaniums such as tetraisopropoxy titanium; boron halides such as boron trifluoride, boron trichloride, boron tribromide, and a boron trifluoride-diethyl etherate; and zinc halides such as zinc chloride and zinc bromide.

Such acids may be used appropriately singly or in combination of two or more thereof.

The amount of such acid used is appropriately selected from the range generally from 0.0001 to 100 equivalents, and preferably from 0.001 to 10 equivalents, based on the α-ionone as a mixture of optical isomers.

Examples of a fluorine-containing alcohol is preferably a fluorine-containing aliphatic alcohol. Specific examples of such fluorine-containing aliphatic alcohol include a saturated or unsaturated fluorine-containing aliphatic alcohol having 2 to 10 carbon atoms. Specific examples of such fluorine-containing aliphatic alcohol include 2,2,2-trifluoroethanol, 2,2-difluoroethanol, 3,3,3-trifluoropropanol, 2,2,3,3,3-pentafluoropropanol, 2,2,3,3-tetrafluoropropanol, 3,3,4,4,4-pentafluorobutanol, 4,4,5,5,5-pentafluoropentanol, 5,5,6,6,6-pentafluorohexanol, 3,3,4,4,5,5,6,6,6-nonafluorohexanol, and 1,1,1,3,3,3-hexafluoro-2-propanol. Such fluorine-containing alcohols may be used appropriately singly or in combination of two or more thereof.

The amount of such fluorine-containing alcohol used is appropriately selected from the range generally from 0.01 to 100 equivalents, and preferably from 0.1 to 10 equivalents, based on the α-ionone as a mixture of optical isomers.

Examples of a base include an inorganic base and an organic base. Examples of an inorganic base include alkali metal hydroxides such as lithium hydroxide, sodium hydroxide, and potassium hydroxide; metal carbonates such as sodium carbonate, potassium carbonate, magnesium carbonate, and calcium carbonate; metal hydrogencarbonates such as sodium hydrogencarbonate, and potassium hydrogencarbonate; metal hydrides such as lithium hydride, sodium hydride, and potassium hydride; and ammonia. Examples of an organic base include alkali or alkaline-earth metal salts such as lithium methoxide, lithium ethoxide, lithium-tert-butoxide, sodium methoxide, sodium ethoxide, sodium-tert-butoxide, potassium methoxide, potassium ethoxide, potassium-tert-butoxide, potassium naphthalenide, sodium acetate, potassium acetate, magnesium acetate, calcium acetate, lithium diethylamide, lithium diisopropylamide, lithium bis(trimethylsilyl)amide, sodium bis(trimethylsilyl)amide, potassium bis(trimethylsilyl)amide, lithium diphenylphosphide, sodium diphenylphosphide, and potassium diphenylphosphide; organic amines such as triethylamine, diisopropylethylamine, N,N-dimethylaniline, piperidine, pyridine, 4-dimethylaminopyridine, 1,5-diazabicyclo[4.3.0]non-5-ene, 1,8-diazabicyclo[5.4.0]undec-7-ene, tri-n-butylamine, and N-methylmorpholine; organic metal compounds such as methyllithium, ethyllithium, n-propyllithium, isopropyllithium, n-butyllithium, sec-butyllithium, tert-butyllithium, phenyllithium, methylmagnesium chloride, ethylmagnesium chloride, n-propylmagnesium chloride, isopropylmagnesium chloride, n-butylmagnesium chloride, sec-butylmagnesium chloride, tert-butylmagnesium chloride, phenylmagnesium chloride, methylmagnesium bromide, ethylmagnesium bromide, n-propylmagnesium bromide, isopropylmagnesium bromide, n-butylmagnesium bromide, sec-butylmagnesium bromide, tert-butylmagnesium bromide, and phenylmagnesium bromide; and the optically active substances (optically active diamine compounds) and racemic forms of the aforementioned diamine compounds exemplified as the aforementioned chiral ligands.

The amount of such a base used is appropriately selected from the range generally from 0 to 100 equivalents, and preferably from 0 to 10 equivalents, based on the α-ionone as a mixture of optical isomers.

Examples of a quaternary ammonium salt include a quaternary ammonium salt having 4 to 24 carbon atoms. Specific examples of such a quaternary ammonium salt include tetrabutylammonium fluoride, tetrabutylammonium chloride, tetrabutylammonium bromide, tetrabutylammonium iodide, triethylbenzylammonium chloride, and tetrabutylammonium triphenyl difluorosilicate.

The amount of such a quaternary ammonium salt used is appropriately selected from the range generally from 0 to 100 equivalents, and preferably from 0 to 10 equivalents, based on a chiral catalyst.

Examples of a quaternary phosphonium salt include a quaternary phosphonium salt having 4 to 36 carbon atoms. Specific examples of such a quaternary phosphonium salt include tetraphenylphosphonium chloride, tetraphenylphosphonium bromide, tetraphenylphosphonium iodide, methyltriphenylphosphonium chloride, methyltriphenylphosphonium bromide, and methyltriphenylphosphonium iodide.

The amount of such a quaternary phosphonium salt used is appropriately selected from the range generally from 0 to 100 equivalents, and preferably from 0 to 10 equivalents, based on a chiral catalyst.

Examples of halogen include bromine and iodine.

The amount of such halogen used is appropriately selected from the range generally from 0 to 100 equivalents, and preferably from 0 to 10 equivalents, based on the α-ionone as a mixture of optical isomers.

Examples of a reducing agent include sodium borohydride, lithium aluminum hydride, and lithium diisobutyl aluminum hydride.

The aforementioned additives may be used appropriately singly or in combination of two or more thereof.

The amount of a reducing agent used is appropriately selected from the range generally from 0 to 100 equivalents, and preferably from 0 to 10 equivalents, based on the α-ionone as a mixture of optical isomers.

An asymmetric reduction can be carried out in a reaction system such as a batch system and a continuous system. In addition, the reduction can be carried out in a reactor used in this field, such as a flask, a reaction kettle, and an autoclave.

The reaction temperature is different depending on the type of a chiral catalyst used, the used amount, etc. The reaction temperature, in consideration of economical efficiency or the like, is appropriately selected from the range generally from 15° C. to 100° C., and preferably from 20° C. to 80° C. Moreover, the reaction can be carried out even at a low temperature from −30° C. to 0° C., or at a high temperature from 100° C. to 250° C.

The reaction time is different depending on reaction conditions such as the type of a chiral catalyst used, the used amount thereof, the type of α-ionone as a mixture of optical isomers used, the concentration thereof, a reaction temperature, or the pressure of hydrogen. The reaction is terminated after a reaction time from several minutes to several hours. The reaction time is appropriately selected from the range generally from 1 minute to 48 hours, and preferably from 10 minutes to 24 hours.

The obtained optically active α-ionol may be directly used, or may be subjected to the aforementioned post-treatment, as necessary.

The aforementioned asymmetric reduction is preferably an asymmetric hydrogenation performed in the presence of a chiral catalyst and in the presence of hydrogen gas. Such a chiral catalyst to be used is preferably the chiral metal complexes such as, for example, RuCl$_2$[(R)-BINAP][(R,R)-DPEN], RuCl$_2$[(R)-BINAP][(R)-DAIPEN], RuCl$_2$[(R)-TOL-BINAP][(R,R)-DPEN], RuCl$_2$[(R)-TOL-BINAP][(R)-DAIPEN], RuCl$_2$[(R)-DM-BINAP][(R,R)-DPEN], and RuCl$_2$[(R)-DM-BINAP][(R)-DAIPEN]. Herein, BINAP indicates 2,2'-bis-(diphenylphosphino)-1,1'-binaphthyl, TOL-BINAP indicates 2,2'-bis-(di-p-tolylphosphino)-1,1'-binaphthyl, DM-BINAP indicates 2,2'-bis[bis(3,5-dimethylphenyl)phosphino]-1,1'-binaphthyl, DPEN indicates 1,2-diphenyl-ethylenediamine, and DAIPEN indicates 1,1-di(4-anisyl)-2-isopropyl-1,2-ethylenediamine, respectively.

Optically active α-ionol obtained by an asymmetric reduction is allowed to react with an esterification agent to give an optically active α-ionol ester.

Such an optically active α-ionol ester obtained by esterification is represented, for example, by formula (7):

[Formula 17]

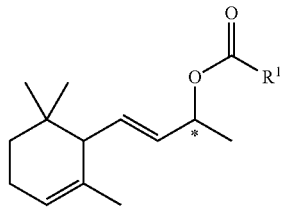

(7)

wherein R$^1$ and * have the same meanings as described above.

Specific examples of such an optically active α-ionol ester include an (S)-α-ionol ester represented by formula (7A):

[Formula 18]

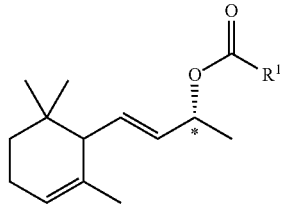

(7A)

wherein R$^1$ and * have the same meanings as described above,
or an (R)-α-ionol ester represented by formula (7B):

[Formula 19]

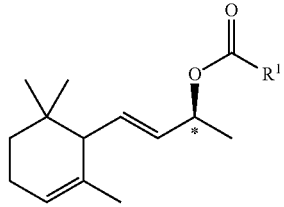

(7B)

wherein R$^1$ and * have the same meanings as described above.

In addition, when the α-ionone as a mixture of optical isomers used as a raw material is an optically active substance, there is obtained an optically active α-ionol ester, wherein the carbon atom at 1-position of the cyclohexene ring of the aforementioned optically active α-ionol ester is an asymmetric carbon atom, which is represented by formula (7C):

[Formula 20]

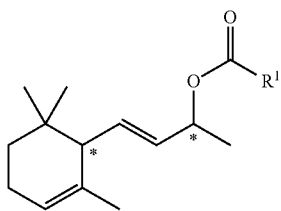

(7C)

wherein R¹ and * have the same meanings as described above.

Specific examples of such an optically active α-ionol ester include the compounds as shown below:

[Formula 21]

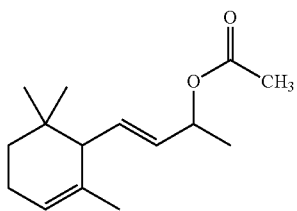

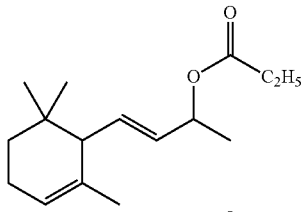

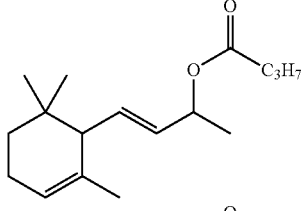

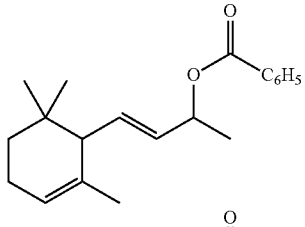

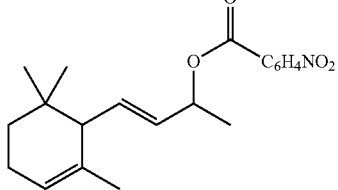

-continued

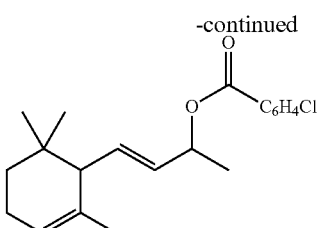

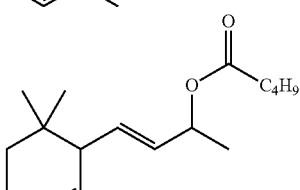

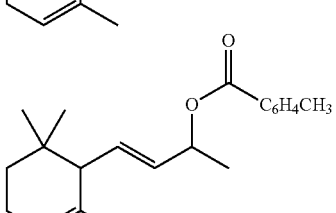

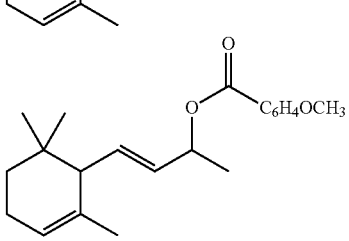

Examples of the obtained optically active α-ionol ester include an (S)-α-ionol ester, wherein the carbon atom at position 2 is represented by the above formula (7A); and an (R)-α-ionol ester, wherein the carbon atom at position 2 is represented by the above formula (7B).

The optical purity of the carbon atom at 2-position of such an optically active α-ionol ester is appropriately selected from the range, for example, from 1% to 99% e.e., preferably from 5% to 99% e.e., and more preferably from 10% to 99% e.e. The aforementioned optical purity is used to mean the optical purity of the asymmetric carbon atom at 2-position of the optically active α-ionol ester. However, there may also be cases where the asymmetric carbon atom at 1-position of the cyclohexene ring is included.

An example of an esterification agent is the esterification agent as described in the above section regarding the reaction of α-ionone as a mixture of optical isomers with an esterification agent. Such an esterification agent used in the reaction with optically active α-ionol is preferably an acid halide represented by the above formula (11-2), wherein the leaving group represented by A¹ in the above formula (11) is a halogen atom.

The amount of such optically active α-ionol used and the amount of such an esterification agent used are not particularly limited because they are different depending on the type of the esterification agent used or the like. The amount of the esterification agent used is appropriately selected from the range generally from 1.0 to 10 equivalents, and preferably from 1.0 to 5.0 equivalents, based on the optically active α-ionol.

Esterification of allowing the optically active α-ionol to react with an esterification agent is preferably carried out in the presence of a basic substance. Such a basic substance is the same basic substance as described in the above section regarding the aforementioned esterification of the α-ionone as a mixture of optical isomers.

The amount of such a basic substance used is appropriately selected from the range generally from 1.0 to 10 equivalents, and preferably from 1.0 to 5.0 equivalents, based on the optically active α-ionol used as a raw material.

Esterification may be carried out in the presence of a solvent, as necessary. Such a solvent is the same solvent as described in the above section regarding the aforementioned esterification of the α-ionone as a mixture of optical isomers.

The amount of such a solvent used is different depending on the type of esterification agent used, the type of the solvent, etc. The amount of such a solvent used is appropriately selected from the range generally from 0.5 to 100 times the volume, and preferably from 1 to 30 times the volume of the optically active α-ionol used as a raw material, based on the optically active α-ionol used as a raw material.

The reaction temperature is different depending on the type of an esterification agent used, the type of a solvent used, etc. Such reaction temperature is appropriately selected from the range generally from 10° C. to 100° C., and preferably from 15° C. to 50° C.

The reaction time is appropriately selected from the range generally from 0.5 to 10 hours, and preferably from 1 to 5 hours.

Thus obtained optically active α-ionol ester is purified as necessary, so as to give an optically active α-ionol ester having a higher optical purity than that of the optically active α-ionol ester obtained by esterification. That is, the obtained optically active α-ionol ester has such an optical purity that a larger amount of the α-ionol ester of an (S) form or an (R) form is contained than that of the optically active α-ionol ester obtained by esterification. Moreover, it is also possible to obtain each optically active α-ionol ester, wherein the asymmetric carbon atom at 1-position of the cyclohexene ring thereof is optically active.

With regard to the optical purity of the optically active α-ionol ester obtained by purification, the optical purity of the carbon atom at 2-position is substantially 100% e.e. It is to be noted that the term "substantially 100% e.e." has the same meaning as described above, and such an optical purity is appropriately selected from the range of 80% e.e. or more, preferably 85% e.e. or more, and more preferably 90% e.e. or more.

Furthermore, the optically active α-ionol ester obtained by purification has a higher chemical purity than that of the optically active α-ionol ester obtained by esterification. The term "higher chemical purity" is used herein to mean a chemical purity higher than that of the optically active α-ionol ester obtained by esterification, and it is substantially 100%. The term "substantially 100%" is used herein to mean a chemical purity in which impurities such as a raw material and an esterification agent, may be contained as components other than the optically active α-ionone obtained by the production method of the present invention, may be contained, so long as such impurities does not impair the properties of the aforementioned optically active α-ionone. A specific example of a chemical purity that is substantially 100% is a chemical purity of 80% more, preferably 85% or more, and more preferably 90% or more.

Examples of a method of purifying an optically active α-ionol ester include recrystallization, crystallization, and optical resolution using an optical resolution agent or microorganisms. Of these, recrystallization is preferable.

Recrystallization may be carried out by an ordinary method applied in this field.

A solvent used in recrystallization is preferably a solvent for dissolving an optically active α-ionol ester. Examples of such a solvent include aromatic hydrocarbons such as benzene, toluene, and xylene; aliphatic hydrocarbons such as pentane, hexane, heptane, and octane; halogenated hydrocarbons such as dichloromethane, chloroform, carbon tetrachloride, and dichloroethane; ethers such as diethyl ether, diisopropyl ether, tert-butyl methyl ether, dimethoxyethane, tetrahydrofuran, dioxane, and dioxolane; alcohols such as methanol, ethanol, 2-propanol, n-butanol, tert-butanol, and benzyl alcohol; polyalcohols such as ethylene glycol, 1,2-propanediol, 1,3-propanediol, and glycerin; amides such as N,N-dimethylformamide, and N,N-dimethylacetamide; acetonitrile; N-methylpyrrolidone; dimethyl sulfoxide; and water. Such solvents may be used appropriately singly or in combination of two or more thereof. Such solvents are preferably aromatic hydrocarbons, aliphatic hydrocarbons, alcohols, and water.

The amount of such a solvent used is different depending on the type of an optically active α-ionol ester, the type of the solvent, etc. Such amount is appropriately selected from the range generally from 0.5 to 30 times the volume, and preferably from 1 to 10 times the volume, based on the optically active α-ionol ester used as a raw material.

Recrystallization may be added a seed crystal to a recrystallization solution, as necessary.

By such purification, an optically active α-ionol ester having a higher optical purity than that of the optically active α-ionol ester obtained by esterification can be obtained.

The one optically active substance at 2-position is preferentially obtained by the asymmetric reduction of α-ionol as a mixture of optical isomers. Therefore, when an optically active α-ionol ester obtained by esterification of the obtained optically active α-ionol is purified, optically active substances at 1-position of a cyclohexene ring in the optically active α-ionol ester can be easily separated. That is, as described above, since the carbon atom at 1-position of a cyclohexene ring in the α-ionone as a mixture of optical isomers is an asymmetric carbon atom, there are two isomers. If they are simply subjected to a reduction, four isomers are generated, and thus it becomes difficult to obtain desired optically active α-ionone. In contrast, by performing the aforementioned asymmetric reduction, the obtained optically active α-ionol substantially has two isomers. Hence, the obtained optically active α-ionol is esterified to give an optically active α-ionol ester, and thus it becomes easier to separate optical isomers.

Thus obtained optically active α-ionol ester or the purified optically active α-ionol ester is hydrolyzed to give optically active α-ionol having a higher optical purity than that of the optically active α-ionol obtained by asymmetric reduction.

With regard to the optical purity of the obtained optically active α-ionol, the optical purity of the carbon atom at 2-position is substantially 100% e.e. It is to be noted that the term "substantially 100% e.e." is used to mean that the optical purity is appropriately selected from the range of 80% e.e. or more, preferably 85% e.e. or more, more preferably 90% e.e. or more, and further more preferably 95% e.e. or more.

The optically active α-ionol ester may be hydrolyzed by the same method as that for the aforementioned α-ionone enol ester.

After completion of the hydrolysis, the aforementioned post-treatment or the like may be carried out, as necessary.

The obtained optically active α-ionol is oxidized to give desired optically active α-ionone. The obtained optically active α-ionone has a higher optical purity than that of the α-ionone as a mixture of optical isomers used as a raw material. The term "higher optical purity" is used herein to mean that the obtained product has such an optical purity that a larger amount of (S) form or (R) form α-ionone is contained than that of the α-ionone as a mixture of optical isomers used as a raw material.

The optical purity of the optically active α-ionone obtained by oxidation is appropriately selected from the range, for example, from 1% to 99% e.e., preferably from 5% to 99% e.e., and more preferably from 10% to 99% e.e. Otherwise, such an optical purity may also be substantially 100% e.e.

Oxidation may be carried out according to a conventional method. Such oxidation, for example, a method using a compound usable as an oxidant, used as a catalyst in the oxidation reaction.

Examples of an oxidant include oxygen, a metal oxide, a peroxide, a perhalogeneacid salt, and an organic oxidant.

Examples of a metal oxide include the oxides of metals such as manganese, cobalt, iron, zirconium, cerium, chromium, ruthenium, and copper. Specific examples thereof include manganese oxide and potassium permanganate.

Examples of a peroxide include organic peroxides such as performic acid, peracetic acid, perpropionic acid, tert-butyl hydroperoxide, cumene hydroperoxide, benzoyl peroxide, perbenzoic acid, metachlorobenzoic acid, perphthalic acid, benzoyl peroxide, di-tert-butyl peroxide, dicumyl peroxide, and tert-butyl perbenzoate; hydrogen peroxide; and ozone.

Examples of a perhalogeneacid salt include, for example, periodic acid and sodium metaperiodate.

Examples of an organic oxidant include, pyridine oxide, dimethylaminopyridine oxide, 2,2,6,6,-tetramethyl-1-piperidinyl oxide, p-chloranil(tetrachloro-p-benzoquinone), o-chloranil, tetrabromo-1,4-benzoquinone, 2,3-dichloro-5,6-dicyano-1,4-benzoquinone, chlorobenzoquinone, and dichlorobenzoquinone.

Such oxidants may be used appropriately singly or in combination of two or more thereof.

The amount of such an oxidant used is different depending on the type of the oxidant, the type of a solvent, etc. Such amount is appropriately selected from the range generally from 1.0 to 100 equivalents, and preferably from 5.0 to 20 equivalents, based on optically active α-ionol.

Oxidation is preferably carried out in the presence of a solvent. Examples of such a solvent include, aliphatic hydrocarbons such as pentane, hexane, heptane, octane, decane, and cyclohexane; aromatic hydrocarbons such as benzene, toluene, and xylene; halogenated hydrocarbons such as dichloromethane, 1,2-dichloroethane, chloroform, carbon tetrachloride, and o-dichlorobenzene; ethers such as diethyl ether, diisopropyl ether, tert-butyl methyl ether, dimethoxyethane, ethylene glycol diethyl ether, tetrahydrofuran, 1,4-dioxane, 1,3-dioxolane, 2-methyltetrahydrofuran, and cyclopentyl methyl ether; ketones such as acetone, methyl ethyl ketone, methyl isobutyl ketone, or cyclohexanone; esters such as methyl acetate, ethyl acetate, n-butyl acetate, and methyl propionate; amides such as formamide, N,N-dimethylformamide, and N,N-dimethylacetamide; sulfoxides such as dimethyl sulfoxide; cyano-containing organic compounds such as acetonitrile; N-methylpyrrolidone; and water. Such solvents may be used appropriately singly or in combination of two or more thereof.

The amount of such a solvent used is different depending on the type of an oxidant, the type of the solvent, etc. Such amount is appropriately selected from the range generally from 0.5 to 100 times the volume, and preferably from 1 to 30 times the volume, based on the optically active α-ionol.

The reaction temperature is different depending on the type of an oxidant used, the type of a solvent used, etc. The reaction temperature is appropriately selected from the range generally from 10° C. to 100° C., and preferably from 15° C. to 50° C.

The reaction time is appropriately selected from the range generally from 0.5 to 48 hours, and preferably from 1 to 24 hours.

After completion of the reaction, the aforementioned post-treatment or the like may be appropriately carried out, as necessary.

In the present invention, the obtained optically active α-ionone represented by the above formula (2) may not required to have an optical purity of substantially 100% e.e. for some uses. In such a case, the obtained optically active α-ionone represented by the above formula (2), which has an optical purity from 10% e.e. to 90% e.e., may be directly used. In addition, the optical purity of the obtained optically active α-ionone may also be adjusted, as appropriate, by altering reaction conditions and the like. Moreover, in order to give an optically active α-ionone having a desired optical purity, the production method of the present invention may be carried out repeatedly. Otherwise, the optically active substances of the optically active α-ionone obtained by the aforementioned production method, namely, an (S) form and an (R) form, may be appropriately mixed with each other, so that the optical purity can be adjusted to a desired optical purity.

Each reaction in the production method of the present invention may be carried out in an inactive gas atmosphere, as necessary. Examples of such inert gas include nitrogen gas and argon gas.

As stated above, the optically active α-ionone obtained by the production method of the present invention is highly optically active α-ionone, which has a higher optical purity than that of the α-ionone as a mixture of optical isomers used as a raw material. The term "highly optically active" is used herein to distinguish the optically active α-ionone as a raw material from the optically active α-ionone as a product. The meanings of the term "highly optically active" are the same as those described regarding the term "higher optical purity." In addition, when optically active α-ionone having a relatively low optical purity, that is, a lower optical purity is used, optically active α-ionone having a high optical purity, that is, highly optically active α-ionone having a high optical purity, can be obtained. The term "lower optical purity" is used herein to distinguish the optically active α-ionone as a raw material from the optically active α-ionone as a product. It means that the optical purity of the optically active α-ionone as a raw material is lower than the optical purity of the obtained optically active α-ionone. It is an optical purity of 1% to 50% e.e., for example. Furthermore, when highly optically active α-ionone having a high optical purity, such as one having an optical purity, for example, from 80% to 99% e.e., and preferably from 80% to 95% e.e., is used as α-ionone as a mixture of optical isomers used as a raw material, optically active α-ionone having a much higher optical purity can be obtained. Still further, when optically active α-ionone is used for the intended use described below, for example, if the optically active α-ionone contains impurities, the aforementioned production method can also be used as a method of purifying it.

The optically active α-ionone and α-ionone enol ester obtained by the production method of the present invention, and in particular, such an α-ionone enol ester is useful as a perfume, various types of intermediates for pharmaceuticals and the like, etc.

Moreover, thus obtained optically active α-ionone has a unique flavor (aroma) and the like, and it also has flavor (aroma) persistency and stability. For example, (R)-α-ionone has a unique and strong floral flavor (aroma), such as a violet-like, fruit-like, and raspberry-like flavor (aroma). On the other hand, (S)-α-ionone has a unique and strong flavor (aroma), such as a fresh juicy greenish flavor (aroma). Such (S)-α-ionone has a wood-like, cedarwood-like, raspberry-like, or β-ionone-like flavor (aroma). Using such optically active α-ionone as a perfume, a perfume composition having higher preference can be provided.

If the optically active α-ionone obtained by the production method of the present invention is used as a perfume in a perfume composition, a perfume composition having the aforementioned properties can be obtained. If it is used in various types of foods and beverages, fragrance products, daily goods and groceries, etc., their commercial values can be enhanced.

The perfume compositions of the present invention include a flavor composition and a fragrance composition.

The amount of the optically active α-ionone obtained by the production method of the present invention that is added into a perfume composition is not particularly limited because it is different depending on the intended use as a perfume composition, the form as a commercial product, etc. When such a perfume composition is used as a flavor composition, for example, the amount of the aforementioned optically active α-ionone used is appropriately selected from the range of generally from 0.0000001% to 1% by mass, preferably from 0.000001% to 0.1% by mass, and more preferably from 0.00001% to 0.01% by mass, based on the total amount of the perfume composition. When such a perfume composition is used as a fragrance composition, for example, the amount of the aforementioned optically active α-ionone used is appropriately selected from the range of generally from 0.001% to 5% by mass, and preferably from 0.01% to 2% by mass, based on the total amount of the perfume composition.

The perfume composition of the present invention, as described above, can be used in foods and beverages, fragrance products, products for daily use and general merchandise, etc.

Examples of such foods and beverages, in which the perfume composition of the present invention can be used, include, beverages such as juice drink, fruit wine, milk beverage, carbonated drink, soft drink, and drinkable preparation; frozen desserts such as ice cream, sherbet, and ice pole; Japanese and Western confections; jam; candy; jelly; gum; bread; favorite beverages such as coffee, cocoa, and tea products including red tea, oolong tea or green tea; soup products such as Japanese soup, Western soup, and Chinese soup; seasonings; various types of instant beverages and foods, and snack foods.

Examples of an oral care product include, dentifrice, oral cleanser, mouthwash, troche, and chewing gum.

Examples of a pharmaceutical include external preparations for skin, such as poultice and ointment; and internal agent.

Examples of a fragrance products include cosmetic products including cleansing cosmetic products such as soap, shower gel and facial cleanser, basic skin care products such as face lotion, face cream, emulsion, facial mask, tanning cream and sunscreen, and finishing cosmetic products such as face powder, foundation, lip stick, rouge for cheek, eye shadow and manicure; hair products such as shampoo, conditioner, hair treatment, hair growth stimulant, hairdressing and hair dye; fragrance products such as perfume or cologne; bath products; bleaching agents, softening agents, dishwashing liquids and laundry liquids; and cleansing agents for health care materials such as disinfectants and insecticides.

Examples of products for daily use and general merchandise include deodorant, environmental fragrance, and car fragrance.

A compound used in a perfume composition, such as the compound described in, for example, "Collection of Well-known Prior Arts Perfume (Syuuchi Kanyo Gijyutsu-syu Koryo)," (edited by Japanese Patent Office), or "Gosei Koryo Kagaku to Syohhin Chishiki (Synthetic Perfumes, Chemistry and Knowledge of Products)," Motoichi Indoh (published by The chemical daily), can be used in the perfume composition of the present invention. Such a compound can be used in a perfume composition together with the optically active α-ionone obtained by the production method of the present invention. In addition, such a compound can be added as another component to the perfume composition of the present invention. In addition to the aforementioned compound, any types of other components can be added to the perfume composition of the present invention, as long as they can be used as perfume compositions. Specific examples of the other components include liquid oil and fat, solid oil and fat, wax, hydrocarbon, plant extracts, Chinese herbal ingredients, alcohols, esters, long-chain fatty acid, surfactants such as a nonionic surfactant, an anionic surfactant, a cationic surfactant or an ampholytic surfactant, sterols, polyalcohols, a moisturizer, a water-soluble polymer, a thickener, a coating agent, a microbicide, an antiseptic, an ultraviolet absorber, a retaining agent, an agent for providing cooling sensation, a calefacient, a masking agent, a whitening agent, a sequestering agent, sugar, amino acids, organic amino acids, a synthetic resin emulsion, a pH adjuster, a skin nutrient, vitamins, an antioxidant, an auxiliary agent used to support inhibition of oxidation, ceramides, NMF (natural moisturizing factor), collagen, urea, oil, powders, functional beads, capsules, a metal chelator, salts, and gums.

The form of the perfume composition of the present invention is not particularly limited, and any form of perfume composition can be used. The form may be appropriately selected and used, and includes, for example, liquid, solid, powder, gel, mist and aerosol.

EXAMPLES

The present invention will be described in detail in the following examples, comparative Examples, and test examples. However, such examples are not intended to limit the scope of the present invention.

The following instruments were used in the measurement of physical properties or the like in the following examples:
Gas chromatography (GC): Hewlett Packard 5890-II
Conversion rate: column; HP-5 (manufactured by GL Sciences Inc.)
Optical purity: chiral column: CP-Chiralsil-Dex CB (manufactured by Chrompack)

Example 1

Synthesis of α-ionone enol acetate

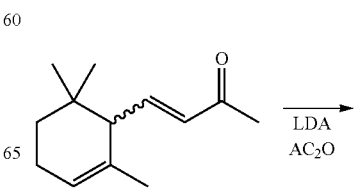

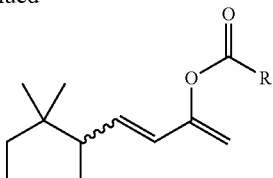

[Formula 22]

To a solution prepared by dissolving 164 g of diisopropylamine in 3,500 mL of tetrahydrofuran (THF) was added dropwise 1,000 mL of a hexane solution of n-butyllithium with stirring at −10° C., followed by stirring for 1 hour. Thereafter, a solution prepared by dissolving 260 g of α-ionone (1) in 3,000 mL of THF was added dropwise to the obtained solution at −10° C., followed by stirring for 1 hour, and then 138 g of acetic anhydride was added dropwise at −10° C. After completion of such dropwise addition, the obtained mixture was subjected to react with stirring for 30 minutes. After completion of the reaction, the reaction mixture was analyzed by GC. As a result, it was confirmed that the conversion rate of the α-ionone was 90.9%. A post-treatment was carried out by a conventional method, to give 295 g of a crude product. The obtained crude product was distilled, to give 221 g of desired α-ionone enol acetate (DM top 80° C.; 0.2 mmHg; 70% yield).

Example 2

Enantioselective Hydrolysis Using Enzyme

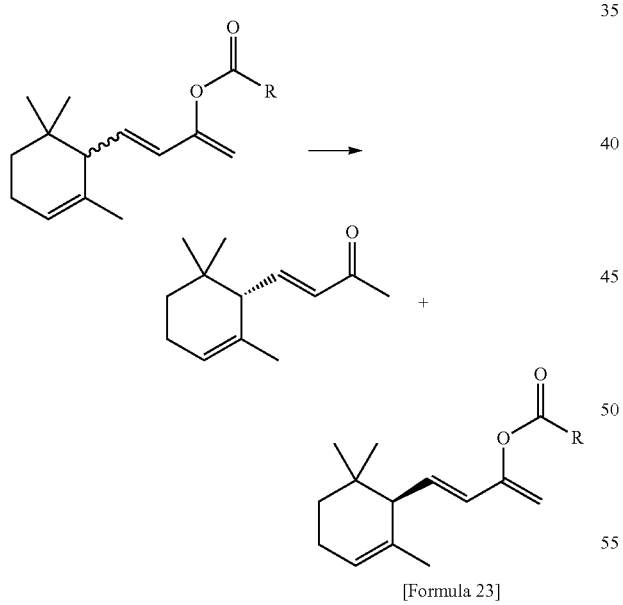

[Formula 23]

To a solution prepared by dissolving 51.42 g of the α-ionone enol acetate obtained in Example 1 in 1,000 mL of diisopropyl ether (IPE) were added 1,000 mL of an acetate buffer (pH=4.6) and 2.57 g of lipase (manufactured by Novozymes) derived from *Candida antarctica*. The obtained mixture was subjected to react with stirring at 35° C. for 8 hours. As a result of analysis using GC, it was confirmed that the conversion rate was 41.7%. Subsequently, a post-treatment was carried out by a conventional method, to give 49.3 g of a mixture of (R)-α-ionone enol acetate and optically active α-ionone. The obtained mixture was distilled, to give 16.85 g of desired (S)-α-ionone (bp 56° C.; 0.1 mmHg; 40% yield; optical purity: 66% e.e.) and (R)-enol acetate (3-R) (bp 67° C.; 0.1 mmHg; 45% yield).

Example 3

Synthesis of (S)-α-ionone enol acetate

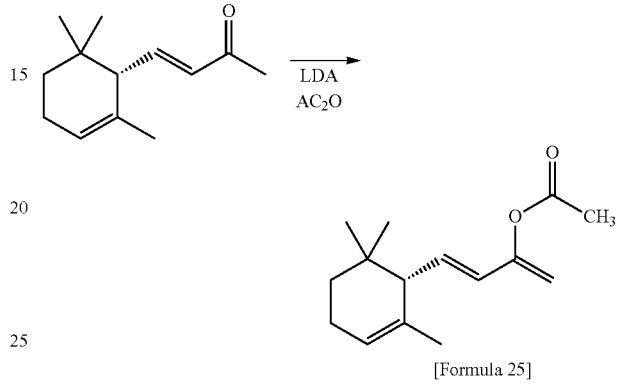

[Formula 25]

In example 1, the same reaction as described in Example 1 was carried out, using 13.72 g of the (S)-α-ionone having an optical purity of 66% e.e. obtained in Example 2 instead of 260 g of α-ionone (1), to give 17.28 g of (S)-α-ionone enol acetate as a crude product. The obtained crude product was distilled, to give 11.70 g of desired (S)-α-ionone enol acetate (bp 80° C.; 0.2 mmHg; 70% yield).

Example 4

Enantioselective Hydrolysis Using Enzyme

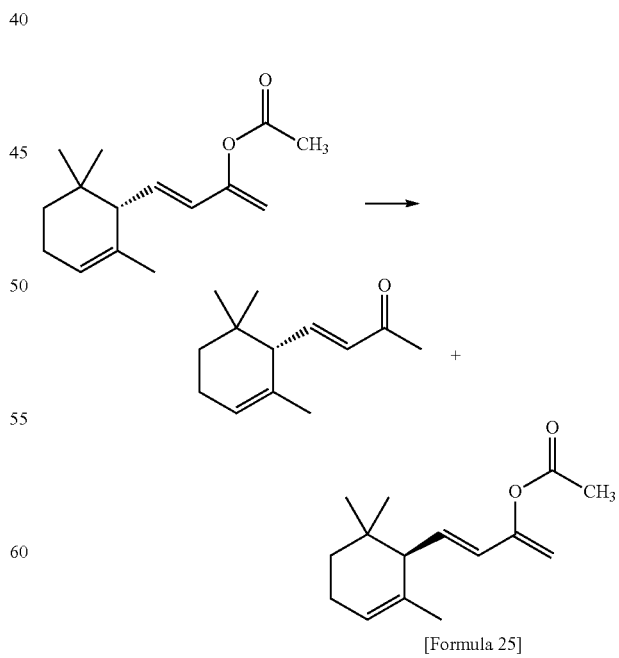

[Formula 25]

The same reaction as described in Example 2 was carried out using 3.48 g of the (S)-α-ionone enol acetate obtained in Example 3, to give 3.27 g of a mixture of (S)-α-ionone and (R)-α-ionone enol acetate as a crude product. The obtained mixture was purified by column chromatography, to give 1.14 g of desired (S)-α-ionone (40% yield; 95% e.e.).

Example 5

Hydrolysis of (R)-α-ionone enol acetate

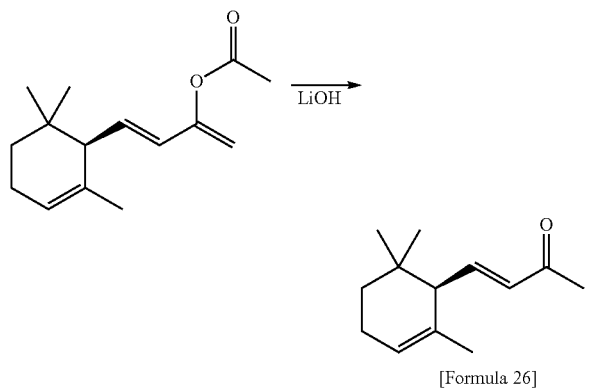

[Formula 26]

A solution prepared by dissolving 0.75 g of lithium hydroxide (LiOH) in 12 mL of water was added to a solution prepared by dissolving 6.10 g of the (R)-α-ionone enol acetate obtained in Example 2 in 24 mL of methanol at a room temperature. The obtained mixture was subjected to react with stirring at a room temperature for 1 hour. Thereafter, termination of the reaction was confirmed by GC, and a post-treatment was then carried out by a conventional method, to give 5.30 g of a crude product. The obtained crude product was purified by column chromatography, to give 4.62 g of desired (R)-α-ionone (92% yield; optical purity: 44% e.e.).

Example 6

Synthesis of (R)-α-ionone 79.0 g of the α-ionone enol acetate obtained in Example 1 was subjected to enantioselective hydrolysis by the same method as that applied in Example 2. Thereafter, it was confirmed that the conversion rate of the α-ionone enol acetate was 83%. The reaction mixture was purified by column chromatography on silica gel to give 6.1 g of (R)-α-ionone enol acetate (8% yield). Subsequently, the obtained (R)-α-ionone enol acetate was hydrolyzed by the same method as that applied in Example 5, followed by distillation and purification, to give 4.6 g of desired (R)-α-ionone (92% yield; 99.9% e.e.).

Example 7

Asymmetric hydrogenation of α-ionone

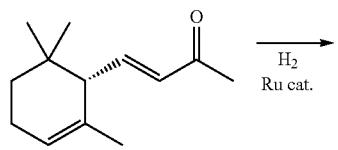

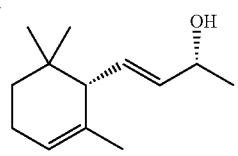

[Formula 27]

Under a nitrogen atmosphere, 18 mg of RuCl$_2$ [(S)-DM-BINAP][(S)-DAIPEN], 200 mg of potassium carbonate (K$_2$CO$_3$), 14 mL of 2-propanol (IPA), and 2.8 g of the (S)-α-ionone obtained in Example 4 were mixed. After deaeration, hydrogen was introduced to a predetermined pressure (3 MPa), and the obtained mixture was subjected to an asymmetric hydrogenation with stirring at 30° C. for 18 hours, and the reaction pressure was then returned to the constant pressure. It was confirmed by GC that the raw material disappeared, and a post-treatment was then carried out by a conventional method, to give 2.72 g of desired optically active α-ionol (95% yield; C9-OH: 90% e.e.).

Example 8

Esterification and Purification by Recrystallization

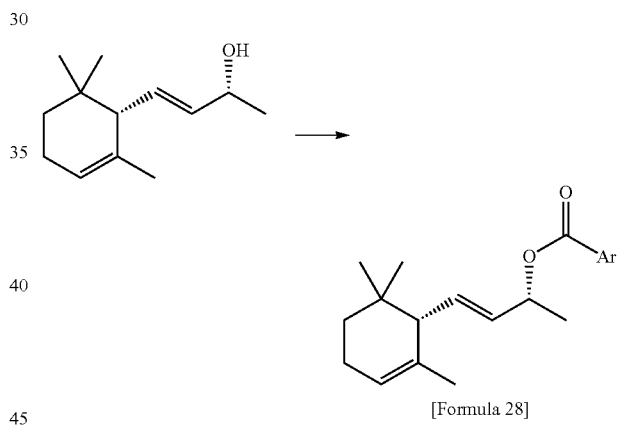

[Formula 28]

(1) Esterification

In 27 mL of toluene was suspended 2.72 g of the optically active α-ionol obtained in Example 6, and 2.2 mL of triethylamine was then added to the suspension. The obtained mixture was stirred at a room temperature. Subsequently, 2.61 g of p-nitrobenzoyl chloride (Ar=p-nitrophenyl group) was added to the mixture, and the obtained mixture was then subjected to react with stirring at a room temperature for 3 hours. Thereafter, it was confirmed by TLC that the raw material disappeared, and a post-treatment was then carried out by a conventional method. Thereafter, the resultant was purified by column chromatography, to give 3.50 g (73% yield) of optically active α-ionol ester in the form of a crystal.

(2) Purification by Recrystallization

The crystalline optically active α-ionol ester obtained in (1) above was dissolved in a heptane-toluene mixed solvent at −25° C., and the solution was then crystallized on standing for 2 days, to give 1.12 g of desired optically active α-ionol ester in a 31% yield (94% d.e. or more).

Example 9

(1) Hydrolysis of Optically Active α-ionol Ester

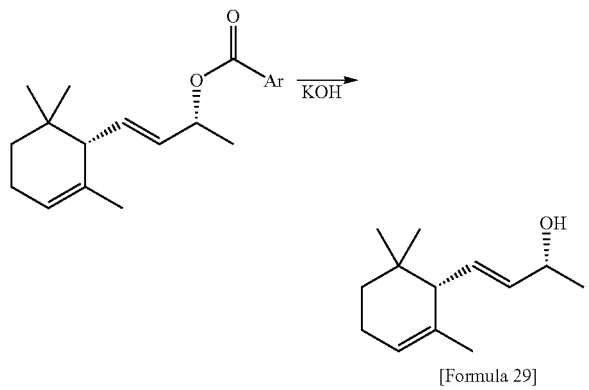

[Formula 29]

In 10 mL of methanol was dissolved 1.12 g of the optically active α-ionol ester obtained in Example 8, and 215 mg of potassium hydroxide was then added thereto. The obtained mixture was subjected to react with stirring at a room temperature for 2 hours. Thereafter, it was confirmed by TLC that the reaction had been terminated, and a post-treatment was then carried out by a conventional method, to give 0.61 g of desired optically active α-ionol (98% yield).

(2) Oxidation Reaction

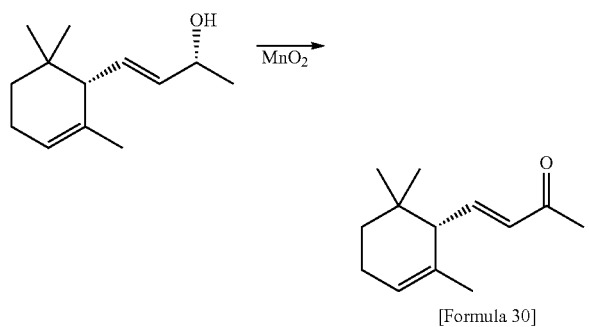

[Formula 30]

In 6 mL of toluene was suspended 0.61 g of the optically active α-ionol obtained in (1) above, and 4.06 g of manganese dioxide was then added thereto. The obtained mixture was subjected to react with stirring at a room temperature for 38 hours. As a result of GC, it was confirmed that the conversion rate was 93%. Thereafter, manganese dioxide was removed by filtration, and the solvent was then distilled away under a reduced pressure. Thereafter, the residue was purified by column chromatography, to give 0.49 g of desired optically active α-ionone (82% yield). As a result of analysis using chiral GC, it was confirmed that the optical purity of the obtained optically active α-ionone was 99% or more.

Example 10

(1) Asymmetric Hydrogenation of α-ionone (Racemic Form)

Under a nitrogen atmosphere, 64 mg of RuCl$_2$ [(S)-DM-BINAP][(S)-DAIPEN], 720 mg of K$_2$CO$_3$, 100 mL of IPA, and g of α-ionone as a racemic form were mixed. After deaeration, the obtained mixture was subjected to an asymmetric hydrogenation at 30° C. and a hydrogen pressure of 3 MPa for 21 hours. The reaction pressure was returned to the constant pressure. It was confirmed by GC that the raw material disappeared, and a post-treatment was then carried out by a conventional method, to give 20.2 g of desired optically active α-ionol (100% yield; 90% e.e.; 0% d.e.).

(2)

To a mixed solution of 20 g of the optically active α-ionol obtained in (1) above with 200 mL of toluene was added 16 mL of triethylamine. Thereafter, 20 g of p-nitrobenzoyl chloride was added to the obtained mixture with stirring under cooling on ice. Thus obtained mixture was subjected to react with stirring at a room temperature for 3 hours. It was confirmed by TLC that the raw material disappeared, and a post-treatment was then carried out by a conventional method. The resultant was purified by column chromatography, to give 35 g of optically active α-ionol ester in the form of a crystal (98% yield).

The obtained optically active α-ionol ester was crystallized twice by dissolving in a toluene-heptane mixed solvent, to give an optically active α-ionol ester (90% d.e.).

Examples 11 and 12 and Comparative Example 1

Rose-Like Fragrance Compositions

Rose-like fragrance compositions as shown in Table 1 below were prepared by using (R)-α-ionone (Example 11) and (S)-α-ionone (Example 12) each having an optical purity of 70% e.e., and α-ionone as a racemic form [manufactured by SIGMA-ALDRICH] (Comparative Example 1). It is to be noted that the unit of each numerical value in formulation examples as shown in the table is "part by mass" (the same is applied below).

TABLE 1

Formulation examples of rose-like fragrance compositions

| Ingredient | Example 11 | Example 12 | Comparative Example 1 |
|---|---|---|---|
| Geraniol | 400.0 | 400.0 | 400.0 |
| Geranium oil | 60.0 | 60.0 | 60.0 |
| Nerol | 200.0 | 200.0 | 200.0 |
| Phenyl ethyl alcohol | 90.0 | 90.0 | 90.0 |
| Eugenol | 10.0 | 10.0 | 10.0 |
| Linalol | 15.0 | 15.0 | 15.0 |
| Geranyl acetate | 35.0 | 35.0 | 35.0 |
| Orris oil | 10.0 | 10.0 | 10.0 |
| Rhodinyl formate | 20.0 | 20.0 | 20.0 |
| Nonanal | 1.0 | 1.0 | 1.0 |
| Undecanal | 2.0 | 2.0 | 2.0 |
| Dodecanal | 2.0 | 2.0 | 2.0 |
| Vanillin | 7.0 | 7.0 | 7.0 |
| Musk T | 8.0 | 8.0 | 8.0 |
| Rose oil | 100.0 | 100.0 | 100.0 |
| (R)-α-ionone | 40.0 | — | — |
| (S)-α-ionone | — | 40.0 | — |
| Racemic-α-ionone | — | — | 40.0 |
| Total | 1000.0 | 1000.0 | 1000.0 |

Test Example 1

Evaluation Test

The rose-like fragrance compositions prepared in Examples 11 and 12 and Comparative Example 1 were subjected to a sensory evaluation, in which 5 perfumers having 5 or more years of experience evaluated the compositions.

As a result of the sensory evaluation, all the panelists evaluated that the rose-like fragrance composition obtained in Example 1, to which (R)-α-ionone had been added, had an aroma of an intense fresh gorgeous floral note, and that the rose-like fragrance composition obtained in Example 2, to which (S)-α-ionone had been added, had an aroma of an intense fresh juicy greenish note. In contrast, they evaluated that the rose-like fragrance composition obtained in Comparative Example 1, to which a racemic form had been added, had a natural aroma, but that such an aroma lacked strength and had somewhat miscellaneous impressions.

Examples 13 and 14 and Comparative Example 2

Gardenia-Like Fragrance Compositions (R)-α-ionone (Example 13) and (S)-α-ionone (Example 14) each having an optical purity of 70% e.e., and α-ionone as a racemic form [manufactured by SIGMA-ALDRICH] (Comparative Example 2) were used to prepare gardenia-like fragrance compositions as shown in Table 2 below, such that such α-ionones were contained in a concentration of 10% by mass based on the total amount of the composition.

TABLE 2

Formulation examples of gardenia-like fragrance compositions

| Ingredient | Example 13 | Example 14 | Comparative Example 2 |
|---|---|---|---|
| Dimethyl benzyl carbinol | 40.0 | 40.0 | 40.0 |
| Methyl phenyl carbinyl acetate | 95.0 | 95.0 | 95.0 |
| Neroli oil | 25.0 | 25.0 | 25.0 |
| Isoeugenol | 40.0 | 40.0 | 40.0 |
| Rose de Mai Absolute | 10.0 | 10.0 | 10.0 |
| Ylang ylang oil | 70.0 | 70.0 | 70.0 |
| Benzyl acetate | 40.0 | 40.0 | 40.0 |
| Jasmine Absolute | 10.0 | 10.0 | 10.0 |
| Lyral | 60.0 | 60.0 | 60.0 |
| Hydroxycitronellal | 200.0 | 200.0 | 200.0 |
| Phenyl ethyl alcohol | 80.0 | 80.0 | 80.0 |
| Phenylacetaldehyde | 7.5 | 7.5 | 7.5 |
| Citronellol | 45.0 | 45.0 | 45.0 |
| Cinnamyl alcohol | 70.0 | 70.0 | 70.0 |
| Coumalin | 25.0 | 25.0 | 25.0 |
| Heliotropin | 75.0 | 75.0 | 75.0 |
| (R)-α-ionone | 100.0 | — | — |
| (S)-α-ionone | — | 100.0 | — |
| Racemic-α-ionone | — | — | 100.0 |
| Dipropylene glycol | Balance | Balance | Balance |
| Total | 1000.0 | 1000.0 | 1000.0 |

Test Example 2

Evaluation Test

The gardenia-like fragrance compositions prepared in Examples 13 and 14 and Comparative Example 2 were subjected to a sensory evaluation, in which 5 perfumers having 5 or more years of experience evaluated the compositions.

As a result of the sensory evaluation, all the panelists evaluated that the gardenia-like fragrance composition obtained in Example 13, to which (R)-α-ionone had been added, had an aroma of an intense fresh gorgeous floral note, and that the gardenia-like fragrance composition obtained in Example 14, to which (S)-α-ionone had been added, had an aroma of an intense fresh juicy greenish note. In contrast, they evaluated that the gardenia-like fragrance composition obtained in Comparative Example 2, to which a racemic form had been added, had a natural aroma, but that such an aroma lacked strength and had somewhat miscellaneous impressions.

Examples 15 and 16 and Comparative Example 3

Carnation-Like Fragrance Compositions (R)-α-ionone (Example 15) and (S)-α-ionone (Example 16) each having an optical purity of 60% e.e., and α-ionone as a racemic form [manufactured by SIGMA-ALDRICH] (Comparative Example 3) were used to prepare carnation-like fragrance compositions as shown in Table 3 below, such that such α-ionones were contained in a concentration of 2% by mass based on the total amount of the composition.

TABLE 3

Formulation examples of carnation-like fragrance compositions

| Ingredient | Example 15 | Example 16 | Comparative Example 3 |
|---|---|---|---|
| Eugenol | 250.0 | 250.0 | 250.0 |
| Isoeugenol | 250.0 | 250.0 | 250.0 |
| Vanillin | 10.0 | 10.0 | 10.0 |
| Amyl salicylate | 50.0 | 50.0 | 50.0 |
| Benzyl salicylate | 50.0 | 50.0 | 50.0 |
| Phenyl ethyl alcohol | 60.0 | 60.0 | 60.0 |
| Rose oil | 10.0 | 10.0 | 10.0 |
| Rhosinol | 100.0 | 100.0 | 100.0 |
| Phenylacetaldehyde | 10.0 | 10.0 | 10.0 |
| Carnation Absolute | 10.0 | 10.0 | 10.0 |
| Methyl eugenol | 30.0 | 30.0 | 30.0 |
| Ylang ylang oil | 10.0 | 10.0 | 10.0 |
| Hydroxycitronellal | 20.0 | 20.0 | 20.0 |
| α-terpineol | 50.0 | 50.0 | 50.0 |
| Black pepper oil | 10.0 | 10.0 | 10.0 |
| Tolu balsam resinoid | 30.0 | 30.0 | 30.0 |
| Benzoin resinoid | 20.0 | 20.0 | 20.0 |
| Pimiento oil | 10.0 | 10.0 | 10.0 |
| (R)-α-ionone | 20.0 | — | — |
| (S)-α-ionone | — | 20.0 | — |
| Racemic-α-ionone | — | — | 20.0 |
| Total | 1000.0 | 1000.0 | 1000.0 |

Test Example 3

Evaluation Test

The carnation-like fragrance compositions prepared in Examples 15 and 16 and Comparative Example 3 were subjected to a sensory evaluation, in which 5 perfumers having 5 or more years of experience evaluated the compositions.

As a result of the sensory evaluation, all the panelists evaluated that the carnation-like fragrance composition obtained in Example 15, to which (R)-α-ionone had been added, had an aroma of an intense fresh gorgeous floral note, and that the carnation-like fragrance composition obtained in Example 16, to which (S)-α-ionone had been added, had an aroma of an intense fresh juicy greenish note. In contrast, they evaluated that the carnation-like fragrance composition obtained in Comparative Example 2, to which a racemic form had been added, had a natural aroma, but that such an aroma lacked strength and had somewhat miscellaneous impressions.

Examples 17 and 18 and Comparative Example 4

Osmanthus-Like Fragrance Compositions (R)-α-ionone (Example 17) and (S)-α-ionone (Example 18) each having an optical purity of 85% e.e., and α-ionone as a racemic form [manufactured by SIGMA-ALDRICH] (Comparative Example 4) were used to prepare Osmanthus-like fragrance compositions as shown in Table 4 below, such that such α-ionones were contained in a concentration of 5% by mass based on the total amount of the composition.

TABLE 4

Formulation examples of Osmanthus-like fragrance compositions

| Ingredient | Example 17 | Example 18 | Comparative Example 4 |
|---|---|---|---|
| Linalol | 100.0 | 100.0 | 100.0 |
| α-terpineol | 100.0 | 100.0 | 100.0 |
| Phenyl ethyl alcohol | 480.0 | 480.0 | 480.0 |
| Citronellol | 120.0 | 120.0 | 120.0 |
| γ-undecalactone | 50.0 | 50.0 | 50.0 |
| γ-decalactone | 20.0 | 20.0 | 20.0 |
| Cis-3-hexenol | 10.0 | 10.0 | 10.0 |
| Ethyl hexanoate | 20.0 | 20.0 | 20.0 |
| Linalyl acetate | 50.0 | 50.0 | 50.0 |
| (R)-α-ionone | 50.0 | — | — |
| (S)-α-ionone | — | 50.0 | — |
| Racemic-α-ionone | — | — | 50.0 |
| Total | 1000.0 | 1000.0 | 1000.0 |

Test Example 4

Evaluation Test

The Osmanthus-like fragrance compositions prepared in Examples 17 and 18 and Comparative Example 4 were subjected to a sensory evaluation, in which 5 perfumers having 5 or more years of experience evaluated the compositions.

As a result of the sensory evaluation, all the panelists evaluated that the Osmanthus-like fragrance composition obtained in Example 17, to which (R)-α-ionone had been added, had an aroma of an intense fresh gorgeous floral note, and that the Osmanthus-like fragrance composition obtained in Example 18, to which (S)-α-ionone had been added, had an aroma of an intense fresh juicy greenish note. In contrast, they evaluated that the Osmanthus-like fragrance composition obtained in Comparative Example 4, to which a racemic form had been added, had a natural aroma, but that such an aroma lacked strength and had somewhat miscellaneous impressions.

Examples 19 and 20 and Comparative Example 5

Violet-Like Fragrance Compositions (R)-α-ionone (Example 19) and (S)-α-ionone (Example 20) each having an optical purity of 50% e.e., and α-ionone as a racemic form [manufactured by SIGMA-ALDRICH] (Comparative Example 5) were used to prepare violet-like fragrance compositions as shown in Table 5 below, such that such α-ionones were contained in a concentration of 15% by mass based on the total amount of the composition.

TABLE 5

Formulation examples of violet-like fragrance compositions

| Ingredient | Example 19 | Example 20 | Comparative Example 5 |
|---|---|---|---|
| Benzyl acetate | 100.0 | 100.0 | 100.0 |
| Bergamot oil | 100.0 | 100.0 | 100.0 |
| Methylionone | 500.0 | 500.0 | 500.0 |
| Benzyl isoeugenol | 40.0 | 40.0 | 40.0 |
| Ylang ylang oil | 20.0 | 20.0 | 20.0 |
| Jasmine Absolute | 20.0 | 20.0 | 20.0 |
| Cassie Absolute | 20.0 | 20.0 | 20.0 |
| 2,6-nonadienal | 2.0 | 2.0 | 2.0 |
| Cis-3-hexenol | 1.0 | 1.0 | 1.0 |
| Ethyl nonenoate | 10.0 | 10.0 | 10.0 |
| Mimosa Absolute | 5.0 | 5.0 | 5.0 |
| Orris Concrete | 25.0 | 25.0 | 25.0 |
| Hydroxycitronellol | 7.0 | 7.0 | 7.0 |
| (R)-α-ionone | 150.0 | — | — |
| (S)-α-ionone | — | 150.0 | — |
| Racemic-α-ionone | — | — | 150.0 |
| Total | 1000.0 | 1000.0 | 1000.0 |

Test Example 5

Evaluation Test

The violet-like fragrance compositions prepared in Examples 19 and 20 and Comparative Example 5 were subjected to a sensory evaluation, in which 5 perfumers having 5 or more years of experience evaluated the compositions.

As a result of the sensory evaluation, all the panelists evaluated that the violet-like fragrance composition obtained in Example 19, to which (R)-α-ionone had been added, had an aroma of an intense fresh gorgeous floral note, and that the violet-like fragrance composition obtained in Example 20, to which (S)-α-ionone had been added, had an aroma of an intense fresh juicy greenish note. In contrast, they evaluated that the violet-like fragrance composition obtained in Comparative Example 5, to which a racemic form had been added, had a natural aroma, but that such an aroma lacked strength and had somewhat miscellaneous impressions.

Examples 21 and 22 and Comparative Example 6

Heliotrope-Like Fragrance Compositions (R)-α-ionone (Example 21) and (S)-α-ionone (Example 22) each having an optical purity of 65% e.e., and α-ionone as a racemic form [manufactured by SIGMA-ALDRICH] (Comparative Example 6) were used to prepare heliotrope-like fragrance compositions as shown in Table 6 below, such that such α-ionones were contained in a concentration of 8% by mass based on the total amount of the composition.

TABLE 6

Formulation examples of heliotrope-like fragrance compositions

| Ingredient | Example 21 | Example 22 | Comparative Example 6 |
|---|---|---|---|
| Heliotropin | 150.0 | 150.0 | 150.0 |
| Coumalin | 30.0 | 30.0 | 30.0 |
| Ethyl vanillin | 30.0 | 30.0 | 30.0 |
| Cinnamyl alcohol | 60.0 | 60.0 | 60.0 |
| Methyl anisate | 30.0 | 30.0 | 30.0 |

TABLE 6-continued

Formulation examples of heliotrope-like fragrance compositions

| Ingredient | Example 21 | Example 22 | Comparative Example 6 |
|---|---|---|---|
| Anisaldehyde | 30.0 | 30.0 | 30.0 |
| Geraniol | 80.0 | 80.0 | 80.0 |
| Phenyl ethyl alcohol | 110.0 | 110.0 | 110.0 |
| Benzyl acetate | 90.0 | 90.0 | 90.0 |
| Jasmine Absolute | 100.0 | 100.0 | 100.0 |
| Mimosa base | 70.0 | 70.0 | 70.0 |
| Ylang ylang oil | 70.0 | 70.0 | 70.0 |
| Caraway oil | 70.0 | 70.0 | 70.0 |
| (R)-α-ionone | 80.0 | — | — |
| (S)-α-ionone | — | 80.0 | — |
| Racemic-α-ionone | — | — | 80.0 |
| Total | 1000.0 | 1000.0 | 1000.0 |

Test Example 6

Evaluation Test

The heliotrope-like fragrance compositions prepared in Examples 21 and 22 and Comparative Example 6 were subjected to a sensory evaluation, in which 5 perfumers having 5 or more years of experience evaluated the compositions.

As a result of the sensory evaluation, all the panelists evaluated that the heliotrope-like fragrance composition obtained in Example 21, to which (R)-α-ionone had been added, had an aroma of an intense fresh gorgeous floral note, and that the heliotrope-like fragrance composition obtained in Example 22, to which (S)-α-ionone had been added, had an aroma of an intense fresh juicy greenish note. In contrast, they evaluated that the heliotrope-like fragrance composition obtained in Comparative Example 6, to which a racemic form had been added, had a natural aroma, but that such an aroma lacked strength and had somewhat miscellaneous impressions.

Examples 23 and 24 and Comparative Example 7

Lilac-Like Fragrance Compositions (R)-α-ionone (Example 23) and (S)-α-ionone (Example 24) each having an optical purity of 99.9% e.e. obtained in the examples, and α-ionone as a racemic form [manufactured by SIGMA-ALDRICH] (Comparative Example 7) were used to prepare lilac-like fragrance compositions as shown in Table 7 below, such that such α-ionones were contained in a concentration of 2% by mass based on the total amount of the composition.

TABLE 7

Formulation examples of lilac-like fragrance compositions

| Ingredient | Example 23 | Example 24 | Comparative Example 7 |
|---|---|---|---|
| α-terpineol | 215.0 | 215.0 | 215.0 |
| Hydroxycitronellol | 200.0 | 200.0 | 200.0 |
| Heliotropin | 100.0 | 100.0 | 100.0 |
| Linalol | 80.0 | 80.0 | 80.0 |
| Phenyl ethyl alcohol | 90.0 | 90.0 | 90.0 |
| Phenylacetaldehyde | 15.0 | 15.0 | 15.0 |
| Jasmine Absolute | 30.0 | 30.0 | 30.0 |
| Benzyl acetate | 70.0 | 70.0 | 70.0 |
| Indole | 5.0 | 5.0 | 5.0 |
| Ylang ylang oil | 10.0 | 10.0 | 10.0 |
| Anisic alcohol | 80.0 | 80.0 | 80.0 |
| Coumalin | 10.0 | 10.0 | 10.0 |
| Phenylpropyl alcohol | 10.0 | 10.0 | 10.0 |
| α-hexylcinnamaldehyde | 30.0 | 30.0 | 30.0 |
| Acetophenone | 10.0 | 10.0 | 10.0 |
| Styrax resinoid | 20.0 | 20.0 | 20.0 |
| γ-undecalactone | 0.5 | 0.5 | 0.5 |
| p-cresyl methyl ether | 1.0 | 1.0 | 1.0 |
| (R)-α-ionone | 20.0 | — | — |
| (S)-α-ionone | — | 20.0 | — |
| Racemic-α-ionone | — | — | 20.0 |
| Dipropylene glycol | Balance | Balance | Balance |
| Total | 1000.0 | 1000.0 | 1000.0 |

Test Example 7

Evaluation Test

The lilac-like fragrance compositions prepared in Examples 23 and 24 and Comparative Example 7 were subjected to a sensory evaluation, in which 5 perfumers having 5 or more years of experience evaluated the compositions.

As a result of the sensory evaluation, all the panelists evaluated that the lilac-like fragrance composition obtained in Example 23, to which (R)-α-ionone had been added, had an aroma of an intense fresh gorgeous floral note, and that the lilac-like fragrance composition obtained in Example 24, to which (S)-α-ionone had been added, had an aroma of an intense fresh juicy greenish note. In contrast, they evaluated that the lilac-like fragrance composition obtained in Comparative Example 7, to which a racemic form had been added, had a natural aroma, but that such an aroma lacked strength and had somewhat miscellaneous impressions.

Examples 25 and 26

Lilac-Like Fragrance Compositions (R)-α-ionone (Example 15) and (S)-α-ionone (Example 16) each having an optical purity of 70% e.e., and α-ionone as a racemic form [manufactured by SIGMA-ALDRICH] (Comparative Example 8) were used to prepare lilac-like fragrance compositions as shown in Table 8 below, such that such α-ionones were contained in a concentration of 7.5% by mass based on the total amount of the composition.

TABLE 8

Lilac-like fragrance compositions

| Ingredient | Example 25 | Example 26 | Comparative Example 8 |
|---|---|---|---|
| Phenyl ethyl alcohol | 250.0 | 250.0 | 250.0 |
| Phenylacetic acid | 25.0 | 25.0 | 25.0 |
| Methyl phenylacetate | 10.0 | 10.0 | 10.0 |
| Dimethylbenzyl carbinol | 25.0 | 25.0 | 25.0 |
| Jasmine Absolute | 10.0 | 10.0 | 10.0 |
| Benzyl acetate | 50.0 | 50.0 | 50.0 |

TABLE 8-continued

Lilac-like fragrance compositions

| Ingredient | Example 25 | Example 26 | Comparative Example 8 |
|---|---|---|---|
| α-hexylcinnamaldehyde | 60.0 | 60.0 | 60.0 |
| Citral | 20.0 | 20.0 | 20.0 |
| Methylacetophenone | 35.0 | 35.0 | 35.0 |
| Oranthiol | 95.0 | 95.0 | 95.0 |
| Heliotropin | 45.0 | 45.0 | 45.0 |
| Cinnamyl alcohol | 150.0 | 150.0 | 150.0 |
| α-terpineol | 150.0 | 150.0 | 150.0 |
| (R)-α-ionone | 75.0 | — | — |
| (S)-α-ionone | — | 75.0 | — |
| Racemic-α-ionone | — | — | 75.0 |
| Total | 1000.0 | 1000.0 | 1000.0 |

Test Example 8

Evaluation Test

The lilac-like fragrance compositions prepared in Examples 25 and 26 and Comparative Example 8 were subjected to a sensory evaluation, in which 5 perfumers having 5 or more years of experience evaluated the compositions.

As a result of the sensory evaluation, all the panelists evaluated that the lilac-like fragrance composition obtained in Example 25, to which (R)-α-ionone had been added, had an aroma of an intense fresh gorgeous floral note, and that the lilac-like fragrance obtained composition in Example 26, to which (S)-α-ionone had been added, had an aroma of an intense fresh juicy greenish note. In contrast, they evaluated that the lilac-like fragrance composition obtained in Comparative Example 8, to which a racemic form had been added, had a natural aroma, but that such an aroma lacked strength and had somewhat miscellaneous impressions.

Examples 27 and 28 and Comparative Example 9

Production of Shampoo Products

The rose-like fragrance composition prepared in Example 11 (Example 27), the rose-like fragrance composition prepared in Example 12 (Example 28), and the rose-like fragrance composition prepared in Comparative Example 1 (Comparative Example 9) were used to produce shampoo products. The following ingredients were stirred, while heating at 80° C., until they became homogenized. Thereafter, the obtained mixture was cooled to 35° C., to give each desired shampoo product.

| [Compositions of shampoo products] | (% by mass) |
|---|---|
| Sodium lauryl sulfate | 40.00 |
| N-coconut oil fatty acid acyl-N-carboxymethoxyethyl-N-carboxymethylethylenediamine disodium | 10.00 |
| Coconut oil fatty acid diethanolamide (2) | 2.00 |
| Butylene glycol | 2.00 |
| Citric acid | 0.35 |
| Sodium chloride | 0.10 |
| Methylparaben | 0.20 |
| Propylparaben | 0.10 |
| Tetrasodium edetate | 0.10 |
| Rose-like fragrance composition | 0.50 |
| Purified water | Balance |
| Total | 100.00 |

Test Example 9

Evaluation Test

The shampoo products produced in Examples 27 and 28 and Comparative Example 8 were subjected to a sensory evaluation, in which 5 skilled panelists evaluated the aroma of each shampoo product.

As a result of the sensory evaluation, all the panelists evaluated that the shampoo product of Example 27, to which a rose-like fragrance composition containing (R)-α-ionone had been added, had an aroma of an intense fresh gorgeous floral note, and that the shampoo product of Example 28, to which a rose-like fragrance composition containing (S)-α-ionone had been added, had an aroma of an intense fresh juicy greenish note. Moreover, they further evaluated that such shampoo products produced in Examples 27 and 28 were excellent in terms of diffusibility and had a fresh, natural sensation. In contrast, all the panelists evaluated that the shampoo product of Comparative Example 9, to which a rose-like fragrance composition containing α-ionone as a racemic form had been added, had a natural aroma, but that such an aroma lacked strength and had somewhat miscellaneous impressions.

Examples 29 and 30

Production of Shower Gel Products

The gardenia-like fragrance composition prepared in Example 13 (Example 29) and the gardenia-like fragrance composition prepared in Example 14 (Example 30) were used to produce shower gel products having the following ingredients.

| [Compositions of shower gel products] | (% by mass) |
|---|---|
| Dibutylhydroxytoluene | 0.05 |
| Methylparaben | 0.10 |
| Propylparaben | 0.10 |
| Tetrasodium edetate | 0.10 |
| Potassium chloride | 0.20 |
| Glycerin | 5.00 |
| Coconut oil fatty acid diethanolamide (2) | 3.00 |
| Sodium polyoxyethylene lauryl ether acetate (3E.O.) (30%) | 10.00 |
| Coconut oil fatty acid amide propyl betaine solution (34%) | 25.00 |
| Potassium myristate (40%) | 25.00 |
| Gardenia-like fragrance composition | 0.50 |
| Purified water | Balance |
| Total | 100.00 |

Comparative Example 10

Production of Shower Gel Products

Shower gel products were produced in the same manner as those in Examples 29 and 30 with the exception that the gardenia-like fragrance composition prepared in Comparative Example 2 was used instead of the gardenia-like fragrance compositions prepared in Examples 13 and 14.

Test Example 10

Evaluation Test

The shower gel products produced in Examples 29 and 30 and Comparative Example 10 were subjected to a sensory evaluation, in which 5 skilled panelists evaluated the aroma of each shower gel product.

As a result of the sensory evaluation, all the panelists evaluated that the shower gel product of Example 29, to which a gardenia-like fragrance composition containing (R)-α-ionone had been added, had an aroma of an intense fresh gorgeous floral note, and that the shower gel product of Example 30, to which a gardenia-like fragrance composition containing (S)-α-ionone had been added, had an aroma of an intense fresh juicy greenish note. Moreover, they further evaluated that such shower gel products produced in Examples 29 and were excellent in terms of diffusibility and had a fresh, natural sensation. In contrast, all the panelists evaluated that the shower gel product of Comparative Example 10, to which a gardenia-like fragrance composition containing α-ionone as a racemic form had been added, had a natural aroma, but that such an aroma lacked strength and had somewhat miscellaneous impressions.

Examples 31 and 32 and Comparative Example 11

Production of Cosmetic Cream Products

The lilac-like fragrance composition prepared in Example 23 (Example 31), the lilac-like fragrance composition prepared in Example 24 (Example 32), and the lilac-like fragrance composition prepared in Comparative Example 7 (Comparative Example 11) were used to produce cosmetic cream products having the following ingredients.

| [Cosmetic cream products] | (% by mass) |
| --- | --- |
| Stearyl alcohol | 6.0 |
| Stearic acid | 2.0 |
| Hydrogenated lanolin | 4.0 |
| Squalane | 9.0 |
| Octyl decanol | 10.0 |
| Glycerin | 6.0 |
| Polyethylene glycol 1500 | 4.0 |
| Polyoxyethylene (25) cetyl ether | 3.0 |
| Glycerin monostearate | 2.0 |
| Methylparaben | Adequate amount |
| Ethylparaben | Adequate amount |
| Lilac-like fragrance composition | 0.1 |
| Purified water | Balance |
| Total | 100.00 |

Test Example 11

Evaluation Test

The cosmetic cream products produced in Examples 31 and 32 and Comparative Example 11 were subjected to a sensory evaluation, in which 5 skilled panelists evaluated the aroma of each cosmetic cream product.

As a result of the sensory evaluation, all the panelists evaluated that the cosmetic cream product of Example 31, to which a lilac-like fragrance composition containing (R)-α-ionone had been added, had an aroma of an intense fresh gorgeous floral note, and that the cosmetic cream product of Example 32, to which a lilac-like fragrance composition containing (S)-α-ionone had been added, had an aroma of an intense fresh juicy greenish note. Moreover, they further evaluated that such cosmetic cream products produced in Examples 31 and were excellent in terms of diffusibility and the feeling of fine texture, and that such products seemed fresh, high-quality products. In contrast, all the panelists evaluated that the cosmetic cream product of Comparative Example 11, to which a lilac-like fragrance composition containing α-ionone as a racemic form had been added, had a natural aroma, but that such an aroma lacked strength and had somewhat miscellaneous impressions.

Examples 33 and 34 and Comparative Example 12

Production of Powder Detergents

The lilac-like fragrance composition prepared in Example 25 (Example 33), the lilac-like fragrance composition prepared in Example 26 (Example 34), and the lilac-like fragrance composition prepared in Comparative Example 8 (Comparative Example 12) were used to produce powder detergents having the following ingredients.

| [Powder detergents] | (% by mass) |
| --- | --- |
| C14-15 alkyl ethoxy sulfonate | 5.5 |
| C12-13 linear alkyl sulfonate | 12.7 |
| C12-13 alkyl ethoxylate | 0.5 |
| Aluminosilicate (76%) | 25.4 |
| Soap | 3.0 |
| Zeolite | 23.0 |
| Sodium silicate | 1.0 |
| Sodium carbonate | Balance |
| Sodium sulfate | 4.0 |
| Sodium sulfite | 1.0 |
| Enzyme | 1.0 |
| Acrylic acid-maleic acid copolymer | 2.5 |
| Fluorescent dye | 0.3 |
| Silicon | 0.3 |
| Lilac-like fragrance composition | 0.3 |
| Purified water | 3.0 |
| Total | 100.00 |

Test Example 12

Evaluation Test

The powder detergents produced in Examples 33 and 34 and Comparative Example 12 were subjected to a sensory evaluation, in which 5 skilled panelists evaluated the aroma of each powder detergent.

As a result of the sensory evaluation, evaluated that the powder detergent of Example 33, to which a lilac-like fragrance composition containing (R)-α-ionone had been added, had an aroma of an intense fresh gorgeous floral note, and that the powder detergent of Example 34, to which a lilac-like fragrance composition containing (S)-α-ionone had been added, had an aroma of an intense fresh juicy greenish note. Moreover, they further evaluated that such powder detergents produced in Examples 33 and 34 was excellent in terms of diffusibility and had a fresh, natural sensation. In contrast, all the panelists evaluated that the powder detergent of Comparative Example 12, to which a lilac-like fragrance composition containing α-ionone as a racemic form had been added, had a natural aroma, but that such an aroma lacked strength and had somewhat miscellaneous impressions.

Examples 35 and 36 and Comparative Example 13

Production of Fabric Softeners

The heliotrope-like fragrance composition prepared in Example 21 (Example 35), the heliotrope-like fragrance composition prepared in Example 22 (Example 36), and the heliotrope-like fragrance composition prepared in Comparative Example 6 (Comparative Example 13) were used to produce fabric softeners having the following ingredients.

| [Fabric softeners] | (% by mass) |
| --- | --- |
| Dialkyl dimethyl ammonium chloride | 15.0 |
| POE (30) lauryl ether | 3.0 |
| Fatty acid | 1.0 |
| Dimethylpolysiloxane | 0.5 |
| Ethylene glycol | 5.0 |
| Antiseptic | Adequate amount |
| Sequestering agent | Adequate amount |
| Heliotrope-like fragrance composition | 0.3 |
| Purified water | Balance |
| Total | 100.00 |

Test Example 12

Evaluation Test

The fabric softeners produced in Examples 35 and 36 and Comparative Example 13 were subjected to a sensory evaluation, in which 5 skilled panelists evaluated the aroma of each fabric softener.

As a result of the sensory evaluation, all the panelists evaluated that the fabric softener of Example 35, to which a heliotrope-like fragrance composition containing (R)-α-ionone had been added, had an aroma of an intense fresh gorgeous floral note, and that the fabric softener of Example 36, to which a heliotrope-like fragrance composition containing (S)-α-ionone had been added, had an aroma of an intense fresh juicy greenish note. Moreover, they further evaluated that such fabric softeners produced in Examples 35 and 36 were excellent in terms of diffusibility and had a fresh, cooling sensation. In contrast, all the panelists evaluated that the fabric softener of Comparative Example 13, to which a heliotrope-like fragrance composition containing α-ionone as a racemic form had been added, had a natural aroma, but that such an aroma was not strong and had somewhat miscellaneous impressions.

Examples 37 and 38 and Comparative Example 14

Peach Flavor Compositions (R)-α-ionone (Example 37) and (S)-α-ionone (Example 38) each having an optical purity of 70% e.e., and α-ionone as a racemic form [manufactured by SIGMA-ALDRICH] (Comparative Example 14) were used to prepare peach flavor compositions as shown in Table 9 below, in such a way that such α-ionones were contained in a concentration of 0.05% by mass based on the total amount of the composition.

TABLE 9

| | Peach flavor compositions | | |
| --- | --- | --- | --- |
| Ingredient | Example 37 | Example 38 | Comparative Example 14 |
| Isoamyl acetate | 10.0 | 10.0 | 10.0 |
| Isoamyl 2-methylbutyrate | 10.0 | 10.0 | 10.0 |
| Isoamyl valerate | 20.0 | 20.0 | 20.0 |
| Anethole | 2.0 | 2.0 | 2.0 |
| Ethyl acetate | 100.0 | 100.0 | 100.0 |
| Ethyl decanoate | 2.0 | 2.0 | 2.0 |
| Ethyl butyrate | 100.0 | 100.0 | 100.0 |
| Ethyl propionate | 50.0 | 50.0 | 50.0 |
| Linalyl butyrate | 2.0 | 2.0 | 2.0 |
| Linalol | 40.0 | 40.0 | 40.0 |
| α-terpineol | 10.0 | 10.0 | 10.0 |
| Benzyl formate | 10.0 | 10.0 | 10.0 |
| Hexanal | 5.0 | 5.0 | 5.0 |
| Cis-3-hexenol | 20.0 | 20.0 | 20.0 |
| Benzaldehyde | 150.0 | 150.0 | 150.0 |
| Lemon oil | 10.0 | 10.0 | 10.0 |
| γ-decalactone | 50.0 | 50.0 | 50.0 |
| γ-heptalactone | 10.0 | 10.0 | 10.0 |
| γ-octalactone | 20.0 | 20.0 | 20.0 |
| γ-nonalactone | 100.0 | 100.0 | 100.0 |
| γ-undecalactone | 150.0 | 150.0 | 150.0 |
| Damascone | 0.1 | 0.1 | 0.1 |
| Vanillin | 10.0 | 10.0 | 10.0 |
| (R)-α-ionone | 0.5 | — | — |
| (S)-α-ionone | — | 0.5 | — |
| Racemic-α-ionone | — | — | 0.5 |
| Ethanol | Balance | Balance | Balance |
| Total | 1000.0 | 1000.0 | 1000.0 |

Test Example 14

Evaluation Test

The peach flavor compositions prepared in Examples 37 and 38 and Comparative Example 14 were subjected to a sensory evaluation, in which 5 flavorists having 5 or more years of experience evaluated the compositions.

As a result of the sensory evaluation, all the panelists evaluated that the peach flavor compositions of Examples 37 and 38, to which (R)-α-ionone and (S)-α-ionone had been added respectively, had a natural, deep, and fresh flavor. In contrast, they evaluated that the peach flavor composition of Comparative Example 14, to which α-ionone as a racemic form had been added, did not have such a natural, deep, and fresh flavor.

Examples 39 and 40 and Comparative Example 15

Apricot Flavor Compositions (R)-α-ionone (Example 39) and (S)-α-ionone (Example 40) each having an optical purity of 85% e.e., and α-ionone as a racemic form [manufactured by SIGMA-ALDRICH] (Comparative Example 15) were used to prepare apricot flavor compositions as shown in Table 10 below, in such a way that such α-ionones were contained in a concentration of 0.95% by mass based on the total amount of the composition.

TABLE 10

Apricot flavor compositions

| Ingredient | Example 39 | Example 40 | Comparative Example 15 |
|---|---|---|---|
| Allyl cyclohexyl decanoate | 0.2 | 0.2 | 0.2 |
| Bitter almond oil | 11.5 | 11.5 | 11.5 |
| Isoamyl acetate | 7.5 | 7.5 | 7.5 |
| Isoamyl butyrate | 7.5 | 7.5 | 7.5 |
| Isoamyl formate | 10.0 | 10.0 | 10.0 |
| Isoamyl isovalerate | 15.0 | 15.0 | 15.0 |
| Ceylon cinnamon oil | 0.5 | 0.5 | 0.5 |
| Ethyl acetate | 14.5 | 14.5 | 14.5 |
| Ethyl butyrate | 4.5 | 4.5 | 4.5 |
| Ethyl hexanoate | 10.0 | 10.0 | 10.0 |
| Ethyl isovalerate | 50.0 | 50.0 | 50.0 |
| Geranium oil | 0.5 | 0.5 | 0.5 |
| Isoamyl phenylacetate | 0.1 | 0.1 | 0.1 |
| Jasmine Absolute | 9.5 | 9.5 | 9.5 |
| Lemon oil | 5.0 | 5.0 | 5.0 |
| Neroli oil | 18.5 | 18.5 | 18.5 |
| Orange oil | 10.5 | 10.5 | 10.5 |
| Propyl cinnamate | 0.2 | 0.2 | 0.2 |
| Rose Absolute | 3.0 | 3.0 | 3.0 |
| γ-undecalactone | 200.0 | 200.0 | 200.0 |
| Vanillin | 85.0 | 85.0 | 85.0 |
| (R)-α-ionone | 9.5 | — | — |
| (S)-α-ionone | — | 9.5 | — |
| Racemic-α-ionone | — | — | 9.5 |
| Ethanol | Balance | Balance | Balance |
| Total | 1000.0 | 100.0 | 1000.0 |

Test Example 15

Evaluation Test

The apricot flavor compositions prepared in Examples 39 and 40 and Comparative Example 15 were subjected to a sensory evaluation, in which 5 flavorists having 5 or more years of experience evaluated the compositions.

As a result of the sensory evaluation, all the panelists evaluated that the apricot flavor compositions of Examples 39 and 40, to which (R)-α-ionone and (S)-α-ionone had been added respectively, had a natural, deep, and fresh flavor. In contrast, they evaluated that the apricot flavor composition of Comparative Example 15, to which α-ionone as a racemic form had been added, did not have such a natural, deep, and fresh flavor.

Examples 41 and 42 and Comparative Example 16

Strawberry Flavor Compositions (R)-α-ionone (Example 41) and (S)-α-ionone (Example 42) each having an optical purity of 55% e.e., and α-ionone as a racemic form [manufactured by SIGMA-ALDRICH] (Comparative Example 16) were used to prepare strawberry flavor compositions as shown in Table 11 below, in such a way that such α-ionones were contained in a concentration of 0.33% by mass based on the total amount of the composition.

TABLE 11

Strawberry flavor compositions

| Ingredient | Example 41 | Example 42 | Comparative Example 16 |
|---|---|---|---|
| Amyl acetate | 17.0 | 17.0 | 17.0 |
| Amyl butyrate | 7.5 | 7.5 | 7.5 |
| Amyl valerate | 7.5 | 7.5 | 7.5 |
| Anethole | 0.8 | 0.8 | 0.8 |
| Benzyl acetate | 42.5 | 42.5 | 42.5 |
| Butyric acid | 7.5 | 7.5 | 7.5 |
| Cinnamyl isobutyrate | 3.5 | 3.5 | 3.5 |
| Cinnamyl valerate | 4.8 | 4.8 | 4.8 |
| Cognac oil | 0.8 | 0.8 | 0.8 |
| Diacetyl | 5.0 | 5.0 | 5.0 |
| Ethyl acetate | 25.0 | 25.0 | 25.0 |
| 3-octanone | 7.5 | 7.5 | 7.5 |
| Ethyl cinnamate | 26.0 | 26.0 | 26.0 |
| Ethyl heptanoate | 1.3 | 1.3 | 1.3 |
| Ethyl 3-methyl-3-phenylglycidate | 130.0 | 130.0 | 130.0 |
| Ethyl propionate | 7.5 | 7.5 | 7.5 |
| Ethyl valerate | 30.0 | 30.0 | 30.0 |
| Raspberry ketone | 2.5 | 2.5 | 2.5 |
| Lemon oil | 0.5 | 0.5 | 0.5 |
| Maltol | 35.0 | 35.0 | 35.0 |
| Methyl anthranilate | 3.3 | 3.3 | 3.3 |
| Methyl cinnamate | 17.8 | 17.8 | 17.8 |
| Methyl heptinecarboxylate | 0.3 | 0.3 | 0.3 |
| Methyl salicylate | 3.3 | 3.3 | 3.3 |
| Neroli oil | 0.3 | 0.3 | 0.3 |
| Orris resinoid | 0.8 | 0.8 | 0.8 |
| γ-undecalactone | 29.3 | 29.3 | 29.3 |
| Vanillin | 35.0 | 35.0 | 35.0 |
| (R)-α-ionone | 3.3 | — | — |
| (S)-α-ionone | — | 3.3 | — |
| Racemic-α-ionone | — | — | 3.3 |
| Ethanol | Balance | Balance | Balance |
| Total | 1000.0 | 1000.0 | 1000.0 |

Test Example 16

Evaluation Test

The strawberry flavor compositions prepared in Examples 41 and 42 and Comparative Example 16 were subjected to a sensory evaluation, in which 5 flavorists having 5 or more years of experience evaluated the compositions.

As a result of the sensory evaluation, all the panelists evaluated that the strawberry flavor compositions of Examples 41 and 42, to which (R)-α-ionone and (S)-α-ionone had been added respectively, had a natural, deep, and fresh flavor. In contrast, they evaluated that the strawberry flavor composition of Comparative Example 16, to which α-ionone as a racemic form had been added, did not have such a natural, deep, and fresh flavor.

Examples 43 and 44 and Comparative Example 17

Passion Fruit Flavor Compositions (R)-α-ionone (Example 43) and (S)-α-ionone (Example 44) each having an optical purity of 75% e.e., and α-ionone as a racemic form [manufactured by SIGMA-ALDRICH] (Comparative Example 17) were used to prepare passion fruit flavor compositions as shown in Table 12 below, in such a way that such α-ionones were contained in a concentration of 0.6% by mass based on the total amount of the composition.

TABLE 12

Passion fruit flavor compositions

| Ingredient | Example 43 | Example 44 | Comparative Example 17 |
|---|---|---|---|
| Ethyl butylate | 11.0 | 11.0 | 11.0 |
| Cis-3-hexenol | 3.0 | 3.0 | 3.0 |
| Hexanol | 5.0 | 5.0 | 5.0 |
| Benzaldehyde | 2.0 | 2.0 | 2.0 |
| Ethyl hexanoate | 19.0 | 19.0 | 19.0 |
| Cis-3-hexenyl acetate | 2.0 | 2.0 | 2.0 |
| Linalol | 70.0 | 70.0 | 70.0 |
| Linalol oxide | 4.0 | 4.0 | 4.0 |
| Hexyl butyrate | 25.0 | 25.0 | 25.0 |
| Hexyl hexanoate | 15.0 | 15.0 | 15.0 |
| α-terpineol | 5.0 | 5.0 | 5.0 |
| Citoral | 15.0 | 15.0 | 15.0 |
| Cis-3-hexenyl butyrate | 4.0 | 4.0 | 4.0 |
| Cis-3-hexenyl hexanoate | 5.0 | 5.0 | 5.0 |
| (R)-α-ionone | 6.0 | — | — |
| (S)-α-ionone | — | 6.0 | — |
| Racemic-α-ionone | — | — | 6.0 |
| Ethanol | Balance | Balance | Balance |
| Total | 1000.0 | 1000.0 | 1000.0 |

Test Example 17

Evaluation Test

The passion fruit flavor compositions prepared in Examples 43 and 44 and Comparative Example 17 were subjected to a sensory evaluation, in which 5 flavorists having 5 or more years of experience evaluated the compositions.

As a result of the sensory evaluation, all the panelists evaluated that the passion fruit flavor compositions of Examples 43 and 44, to which (R)-α-ionone and (S)-α-ionone had been added respectively, had a natural, deep, and fresh flavor. In contrast, they evaluated that the passion fruit flavor composition of Comparative Example 17, to which α-ionone as a racemic form had been added, did not have such a natural, deep, and fresh flavor.

Examples 45 and 46 and Comparative Example 18

Pear Flavor Compositions (R)-α-ionone (Example 45) and (S)-α-ionone (Example 46) obtained in the examples and α-ionone as a racemic form [manufactured by SIGMA-ALDRICH] (Comparative Example 18) were used to prepare pear flavor compositions as shown in Table 13 below, in such a way that such α-ionones were contained in a concentration of 0.0005% by mass based on the total amount of the composition.

TABLE 13

Pear flavor compositions

| Ingredient | Example 45 | Example 46 | Comparative Example 18 |
|---|---|---|---|
| Amyl acetate | 670.0 | 670.0 | 670.0 |
| Amyl valerate | 65.0 | 65.0 | 65.0 |
| Benzyl acetate 10% | 12.5 | 12.5 | 12.5 |
| Ethyl acetate | 40.0 | 40.0 | 40.0 |
| Ethyl butyrate | 6.5 | 6.5 | 6.5 |

TABLE 13-continued

Pear flavor compositions

| Ingredient | Example 45 | Example 46 | Comparative Example 18 |
|---|---|---|---|
| Ethyl decanoate | 1.0 | 1.0 | 1.0 |
| Ethyl heptanoate | 1.0 | 1.0 | 1.0 |
| Ethyl hexanoate | 0.5 | 0.5 | 0.5 |
| Ethyl octanoate | 1.0 | 1.0 | 1.0 |
| Geranyl propionate | 50.0 | 50.0 | 50.0 |
| Hexyl acetate | 1.0 | 1.0 | 1.0 |
| Lemon oil | 1.5 | 1.5 | 1.5 |
| Orris resinoid 1% | 2.5 | 2.5 | 2.5 |
| Rose Absolute 1% | 0.5 | 0.5 | 0.5 |
| Vanillin | 2.5 | 2.5 | 2.5 |
| (R)-α-ionone 1% | 0.5 | — | — |
| (S)-α-ionone 1% | — | 0.5 | — |
| Racemic-α-ionone 1% | — | — | 0.5 |
| Ethanol | Balance | Balance | Balance |
| Total | 1000.0 | 1000.0 | 1000.0 |

Test Example 18

Evaluation Test

The pear flavor compositions prepared in Examples 45 and 46 and Comparative Example 18 were subjected to a sensory evaluation, in which 5 flavorists having 5 or more years of experience evaluated the compositions.

As a result of the sensory evaluation, all the panelists evaluated that the pear flavor compositions of Examples 45 and 46, to which (R)-α-ionone and (S)-α-ionone had been added respectively, had a natural, deep, and fresh flavor. In contrast, they evaluated that the pear flavor composition of Comparative Example 18, to which α-ionone as a racemic form had been added, did not have such a natural, deep, and fresh flavor.

Examples 47 and 48 and Comparative Example 19

Mango Flavor Compositions (R)-α-ionone (Example 47) and (S)-α-ionone (Example 48) each having an optical purity of 80% e.e., and α-ionone as a racemic form [manufactured by SIGMA-ALDRICH] (Comparative Example 19) were used to prepare mango flavor compositions as shown in Table 14 below, in such a way that such α-ionones were contained in a concentration of 0.1% by mass based on the total amount of the composition.

TABLE 14

Mango flavor compositions

| Ingredient | Example 47 | Example 48 | Comparative Example 19 |
|---|---|---|---|
| Acetic acid | 7.0 | 7.0 | 7.0 |
| Benzyl alcohol | 50.0 | 50.0 | 50.0 |
| Butyric acid | 16.0 | 16.0 | 16.0 |
| 3-carene | 10.0 | 10.0 | 10.0 |
| Citral | 2.0 | 2.0 | 2.0 |
| p-cymene | 10.0 | 10.0 | 10.0 |
| Ethyl dodecanoate | 9.0 | 9.0 | 9.0 |
| Hexanoic acid | 13.0 | 13.0 | 13.0 |
| Hexanol | 6.0 | 6.0 | 6.0 |
| γ-hexalactone | 2.0 | 2.0 | 2.0 |
| Furfural | 1.0 | 1.0 | 1.0 |
| Cis-3-hexenol | 3.0 | 3.0 | 3.0 |

TABLE 14-continued

Mango flavor compositions

| Ingredient | Example 47 | Example 48 | Comparative Example 19 |
|---|---|---|---|
| Limonene | 7.0 | 7.0 | 7.0 |
| 5-methyl furural | 1.0 | 1.0 | 1.0 |
| γ-nonalactone | 8.0 | 8.0 | 8.0 |
| γ-octalactone | 1.0 | 1.0 | 1.0 |
| Terpinolene | 3.0 | 3.0 | 3.0 |
| (R)-α-ionone | 1.0 | — | — |
| (S)-α-ionone | — | 1.0 | — |
| Racemic-α-ionone | — | — | 1.0 |
| Ethanol | Balance | Balance | Balance |
| Total | 1000.0 | 1000.0 | 1000.0 |

Test Example 19

Evaluation Test

The mango flavor compositions prepared in Examples 47 and 48 and Comparative Example 19 were subjected to a sensory evaluation, in which 5 flavorists having 5 or more years of experience evaluated the compositions.

As a result of the sensory evaluation, all the panelists evaluated that the mango flavor compositions of Examples 47 and 48, to which (R)-α-ionone and (S)-α-ionone had been added respectively, had a natural, deep, and fresh flavor. In contrast, they evaluated that the mango flavor composition of Comparative Example 19, to which α-ionone as a racemic form had been added, did not have such a natural, deep, and fresh flavor.

Examples 49 and 50 and Comparative Example 20

Raspberry Flavor Compositions (R)-α-ionone (Example 49) and (S)-α-ionone (Example 50) each having an optical purity of 60% e.e., and α-ionone as a racemic form [manufactured by SIGMA-ALDRICH] (Comparative Example 20) were used to prepare raspberry flavor compositions as shown in Table 15 below, in such a way that such α-ionones were contained in a concentration of 10.5% by mass based on the total amount of the composition.

TABLE 15

Raspberry flavor compositions

| Ingredient | Example 49 | Example 50 | Comparative Example 20 |
|---|---|---|---|
| Amyl acetate | 250.0 | 250.0 | 250.0 |
| Amyl butyrate | 7.5 | 7.5 | 7.5 |
| Anethole | 0.3 | 0.3 | 0.3 |
| Methyl N-methylanthranilate | 0.5 | 0.5 | 0.5 |
| Ethyl acetate | 30.0 | 30.0 | 30.0 |
| Ethyl butyrate | 37.0 | 37.0 | 37.0 |
| Ethyl 3-methyl-3-phenylglycidate | 10.0 | 10.0 | 10.0 |
| Geraniol | 6.5 | 6.5 | 6.5 |
| Raspberry ketone | 8.0 | 8.0 | 8.0 |
| Jasmine Absolute 10% | 3.5 | 3.5 | 3.5 |
| Lemon oil | 6.5 | 6.5 | 6.5 |
| Maltol | 1.5 | 1.5 | 1.5 |
| Dimethyl disulfide | 0.5 | 0.5 | 0.5 |
| α-irone | 30.2 | 30.2 | 30.2 |
| Rhosinol | 5.0 | 5.0 | 5.0 |
| γ-undecalactone | 5.0 | 5.0 | 5.0 |
| Vanillin | 43.0 | 43.0 | 43.0 |
| (R)-α-ionone | 105.0 | — | — |
| (S)-α-ionone | — | 105.0 | — |
| Racemic-α-ionone | — | — | 105.0 |
| Ethanol | Balance | Balance | Balance |
| Total | 1000.0 | 1000.0 | 1000.0 |

Test Example 20

Evaluation Test

The raspberry flavor compositions prepared in Examples 49 and 50 and Comparative Example 20 were subjected to a sensory evaluation, in which 5 flavorists having 5 or more years of experience evaluated the compositions.

As a result of the sensory evaluation, all the panelists evaluated that the raspberry flavor compositions of Examples 49 and 50, to which (R)-α-ionone and (S)-α-ionone had been added respectively, had a natural, deep, and fresh flavor. In contrast, they evaluated that the raspberry flavor composition of Comparative Example 20, to which α-ionone as a racemic form had been added, did not have such a natural, deep, and fresh flavor.

Examples 51 and 52 and Comparative Example 21

Raspberry Flavor Compositions (R)-α-ionone (Example 51) and (S)-α-ionone (Example 52) each having an optical purity of 80% e.e., and α-ionone as a racemic form [manufactured by SIGMA-ALDRICH] (Comparative Example 21) were used to prepare raspberry flavor compositions as shown in Table 16 below, in such a way that such α-ionones were contained in a concentration of 3% by mass based on the total amount of the composition.

TABLE 16

Raspberry flavor compositions

| Ingredient | Example 51 | Example 52 | Comparative Example 51 |
|---|---|---|---|
| Ethyl 3-methyl-3-phenylglycidate | 400.0 | 400.0 | 400.0 |
| Acetoin | 3.0 | 3.0 | 3.0 |
| Benzylideneacetone | 100.0 | 100.0 | 100.0 |
| Methoxy acetoxy acetophenone | 60.0 | 60.0 | 60.0 |
| Benzyl acetate | 50.0 | 50.0 | 50.0 |
| Phenyl ethyl alcohol | 50.0 | 50.0 | 50.0 |
| Essence of Portugal | 50.0 | 50.0 | 50.0 |
| Vanillin | 40.0 | 40.0 | 40.0 |
| Methylionone | 30.0 | 30.0 | 30.0 |
| Hexyl acetate | 10.0 | 10.0 | 10.0 |
| Cis-3-hexenyl acetate | 10.0 | 10.0 | 10.0 |
| Methyl salicylate | 10.0 | 10.0 | 10.0 |
| Benzaldehyde | 5.0 | 5.0 | 5.0 |
| Ethyl benzoate | 10.0 | 10.0 | 10.0 |
| Methyl butanol | 10.0 | 10.0 | 10.0 |
| Bornyl salicylate | 10.0 | 10.0 | 10.0 |
| Clove oil | 10.0 | 10.0 | 10.0 |
| Geranium oil | 10.0 | 10.0 | 10.0 |

TABLE 16-continued

Raspberry flavor compositions

| Ingredient | Example 51 | Example 52 | Comparative Example 51 |
|---|---|---|---|
| Hexyl alcohol | 5.0 | 5.0 | 5.0 |
| Cis-3-hexenol | 5.0 | 5.0 | 5.0 |
| Coumalin | 10.0 | 10.0 | 10.0 |
| Orris Concrete | 15.0 | 15.0 | 15.0 |
| Ethyl acetate | 10.0 | 10.0 | 10.0 |
| Ethyl caproate | 10.0 | 10.0 | 10.0 |
| Isoamyl caproate | 10.0 | 10.0 | 10.0 |
| Anisic aldehyde | 5.0 | 5.0 | 5.0 |
| Diacetyl | 2.0 | 2.0 | 2.0 |
| (R)-α-ionone | 30.0 | — | — |
| (S)-α-ionone | — | 30.0 | — |
| Racemic-α-ionone | — | — | 30.0 |
| Ethanol | Balance | Balance | Balance |
| Total | 1000.0 | 1000.0 | 1000.0 |

Test Example 21

Evaluation Test

The raspberry flavor compositions prepared in Examples 51 and 52 and Comparative Example 21 were subjected to a sensory evaluation, in which 5 flavorists having 5 or more years of experience evaluated the compositions.

As a result of the sensory evaluation, all the panelists evaluated that the raspberry flavor compositions of Examples 51 and 52, to which (R)-α-ionone and (S)-α-ionone had been added respectively, had a natural, deep, and fresh flavor. In contrast, they evaluated that the raspberry flavor composition of Comparative Example 21, to which α-ionone as a racemic form had been added, did not have such a natural, deep, and fresh flavor.

Examples 53 and 54 and Comparative Example 22

Production of Peach-Like Carbonated Drinks

The peach flavor composition prepared in Example 37 (Example 53), the peach flavor composition prepared in Example 38 (Example 54), and the peach flavor composition prepared in Comparative Example 14 (Example 22) were used. In accordance with the formulation example as shown below, the ingredients as shown below were mixed, and 60 parts by mass of purified water was then added to the mixture, to prepare peach syrup. Thereafter, 4 parts by mass of carbonated water was added to 6 parts by mass of thus prepared syrup, to give a carbonated drink.

| [Formulation example] | (% by mass) |
|---|---|
| Maltitol syrup | 8.0 |
| Aspartame | 0.01 |
| Polydextrose syrup | 6.3 |
| Peach 5-times concentrated fruit juice | 0.7 |
| Citric acid (crystal) | 0.1 |
| Peach flavor composition | 0.2 |
| Menthol | 0.0002 |
| Menthoxypropanediol | 0.00002 |

Test Example 22

Evaluation Test

The carbonated drinks produced in Examples 53 and 54 and Comparative Example 22 were subjected to a sensory evaluation, in which 5 skilled panelists evaluated the flavor of each carbonated drink.

As a result of the sensory evaluation, all the panelists evaluated that the carbonated drink of Example 53, to which a peach flavor composition containing (R)-α-ionone had been added, had a flavor of an intense fresh and breezy note, and that the carbonated drink of Example 54, to which a peach flavor composition containing (S)-α-ionone had been added, had a flavor of an intense fresh, juicy note. Moreover, they further evaluated that such carbonated drinks produced in Examples 53 and 54 were excellent in terms of diffusibility and had a fresh variation of notes with time. In contrast, all the panelists evaluated that the carbonated drink of Comparative Example 22, to which a peach flavor composition containing α-ionone as a racemic form had been added, had a natural flavor, but that such a flavor lacked strong and had somewhat miscellaneous impressions.

Examples 55 and 56 and Comparative Example 23

Production of Pear-Like Distilled Spirit (Syohchuh)-Based Highball Beverages

The peach flavor compositions prepared in Examples and 46 and Comparative Example 18 were used. In accordance with the formulation example as shown below, the ingredients as shown below were mixed, and purified water was then added to the mixture, to prepare 300 parts by mass of liqueur. Thereafter, 4 parts by mass of carbonated water was added to 6 parts by mass of thus prepared liqueur, to give a distilled spirit-based highball beverage.

| [Formulation example] | (% by mass) |
|---|---|
| Xylitol | 28.0 |
| Pear 5-times concentrated fruit juice | 6.0 |
| 60% ethanol | 85.0 |
| Citric acid | 1.7 |
| Peach flavor composition | 1.0 |
| Menthol | 0.0005 |
| Menthyl lactate | 0.0001 |
| Purified water | Balance |
| Total | 300.0 |

Test Example 23

Evaluation Test

The pear-like distilled spirit-based highball beverages produced in Examples 55 and 56 and Comparative Example 23 were subjected to a sensory evaluation, in which 5 skilled panelists evaluated the flavor of each distilled spirit-based highball beverage.

As a result of the sensory evaluation, all the panelists evaluated that the pear-like distilled spirit-based highball beverage of Example 55, to which a peach flavor composition containing (R)-α-ionone had been added, had a flavor of an intense fresh and breezy note, and that the pear-like distilled spirit-based highball beverage of Example 56, to which a peach flavor composition containing (S)-α-ionone had been added, had a fresh, juicy flavor of an intense fresh and juicy note. Moreover, they further evaluated that such pear-like distilled spirit-based highball beverages produced in Examples 55 and 56 were excellent in terms of diffusibility and had a fresh variation of notes with time. In contrast, all the panelists evaluated that the pear-like distilled spirit-based highball beverage of Comparative Example 23, to which a peach flavor composition containing α-ionone as a racemic form had been added, had a natural flavor, but that such a flavor lacked strength and had somewhat miscellaneous impressions.

Examples 57 and 58 and Comparative Example 24

Production of Raspberry Jams

In accordance with the formulation example as shown below, raspberry was cooked over low heat. After it was boiled, granulated sugar, lemon juice, and brandy were added to the boiled raspberry, and the obtained mixture was further cooled over medium heat for approximately 10 minutes, while skimming the scum at times and paying attention not to scorch. Thereafter, the resultant was cooled to a room temperature, and each of the raspberry flavor compositions prepared in Examples 51 and 52 and Comparative Example 21 was then added respectively thereto, to give a raspberry jam.

Formulation Example

| Raspberry | 250 g |
| Granulated sugar | 175 g |
| Lemon juice | ¼ of a whole lemon |
| Brandy | 5 g |
| Raspberry flavor composition | 0.1 g |

Test Example 24

Evaluation Test

The raspberry jams produced in Examples 57 and 58 and Comparative Example 24 were subjected to a sensory evaluation, in which 5 skilled panelists evaluated the flavor of each raspberry jam.

As a result of the sensory evaluation, all the panelists evaluated that the raspberry jam of Example 57, to which a raspberry flavor composition containing (R)-α-ionone had been added, had a flavor of an intense fresh and breezy note, and that the raspberry jam of Example 58, to which a raspberry flavor composition containing (S)-α-ionone had been added, had a flavor of an intense fresh and juicy note. Moreover, they further evaluated that such raspberry jams of Examples 57 and 58 were excellent in terms of diffusibility and had a fresh variation of notes with time. In contrast, all the panelists evaluated that the raspberry jam of Comparative Example 24, to which a raspberry flavor composition containing α-ionone as a racemic form had been added, had a natural flavor, but that such a flavor lacked strength and had somewhat miscellaneous impressions.

Examples 59 and 60 and Comparative Example 25

Production of Strawberry Sauces

In accordance with the formulation example as shown below, strawberry and granulated sugar were cooked over medium heat, while skimming the scum at time. After they were boiled, lemon juice was added thereto, and they were then blended. Thereafter, the obtained mixture was cooled to a room temperature. Subsequently, each of the strawberry flavor compositions prepared in Examples 41 and 42 and Comparative Example 16 was then added thereto, to give a strawberry sauce.

Formulation Example

| Strawberry | 250 g |
| Granulated sugar | 175 g |
| Lemon juice | ¼ of a whole lemon |
| Strawberry flavor composition | 0.1 g |

Test Example 25

Evaluation Test

The strawberry sauces produced in Examples 59 and 60 and Comparative Example 25 were subjected to a sensory evaluation, in which 5 skilled panelists evaluated the flavor of each strawberry sauce.

As a result of the sensory evaluation, all the panelists evaluated that the strawberry sauce of Example 59, to which a strawberry flavor composition containing (R)-α-ionone had been added, had a fresh, pleasant flavor of an intense fresh and breezy note, and that the strawberry sauce of Example 60, to which a strawberry flavor composition containing (S)-α-ionone had been added, had a flavor of an intense fresh and juicy note. Moreover, they further evaluated that such strawberry sauces of Examples 59 and 60 were excellent in terms of diffusibility and had a fresh variation of notes with time. In contrast, all the panelists evaluated that the strawberry sauce of Comparative Example 25, to which a raspberry flavor composition containing α-ionone as a racemic form had been added, had a natural flavor, but that such a flavor lacked strength and had somewhat miscellaneous impressions.

Examples 61 and 62

Preparation of Rose-Like Fragrance Compositions (R)-α-ionones having an optical purity ranging from 5% e.e. to 95% e.e. (in increments of 5% e.e.) and (R)-α-ionone having an optical purity of 99% e.e. or more were prepared. Subsequently, such (R)-α-ionones were used instead of (R)-α-ionone having an optical purity of 70% e.e. in Example 11, to prepare rose-like fragrance compositions (Example 61). In addition, (S)-α-ionones were used instead of such (R)-α-ionones in Example 61, to prepare rose-like fragrance compositions (Example 62).

Examples 63 and 64

Preparation of Rose-Like Fragrance Compositions

With regard to (R)-α-ionone having an optical purity of 70% e.e. that included at 4% by mass in the rose-like fragrance compositions prepared in Example 11, its mixed amount was appropriately changed from 10 ppm to 50% by mass, to prepare rose-like fragrance compositions (Example 63). In addition, (S)-α-ionones were used instead of such (R)-α-ionones in Example 63, to prepare rose-like fragrance compositions (Example 64).

Test Examples 26 to 29

Evaluation Test

The rose-like fragrance compositions prepared in Examples 61 and 62 and the rose-like fragrance compositions prepared in Examples 63 and 64 were subjected to an evaluation test, in which 5 perfumers having 5 or more years of experience evaluated the aforementioned compositions by the following method.
Evaluation Test:
The rose-like fragrance compositions prepared in Examples 61 to 64 were subjected to an evaluation test, and they were evaluated according to a 2:2 points discrimination method (which is a method used to discriminate between two types of samples A and B, which comprises showing samples A and B as identified samples to panelists so that they can memorize the characteristics thereof, then showing the two samples as unidentified samples so that the panelists are allowed to point out a sample different from sample A, and then determining whether a difference exists between the two types of samples based on the number of correct answers obtained by performing the aforementioned operation several times; Shin Sato, "Kannoh Kensa Nyuhmon (Introduction to Sensory Test)", p. 54 (Oct. 16, 1978, published by Union of Japanese Scientists and Engineers (JUSE) Press. Ltd.).

As a result of the evaluation test, it was found that the rose-like fragrance compositions prepared in Examples 61 and 62 (Test example 26 and 27), which achieved an optical purity of 10% e.e. or more, even using either (R)-α-ionone or (S)-α-ionone, significantly exhibited the effect of the optical purity. In addition, such rose-like fragrance compositions, which had an optical purity of 30% e.e. to 95% e.e., more significantly exhibited the effect of the optical purity. Moreover, such rose-like fragrance compositions, which had an optical purity of almost 50% e.e. to 85% e.e., further more significantly exhibited the effect of the optical purity.

Furthermore, it was also found that even using either (R)-α-ionone or (S)-α-ionone, it may be better that the rose-like fragrance compositions prepared in Examples 63 and 64 (Test example 28 and 29) are used within the range from 20 ppm to 20% by mass. A rose-like fragrance composition used in a mixed amount of 20 ppm or more exhibited a clearer mixing effect than that of a rose-like fragrance composition used in a mixed amount of less than 20 ppm. Moreover, it was found that a rose-like fragrance composition used in a mixed amount of 20% by mass or less had a better balance of the flavor of the fragrance composition than that of a rose-like fragrance composition used in a mixed amount of more than 20% by mass.

Examples 65 and 66

Peach Flavor Compositions (R)-α-ionones having an optical purity ranging from 5% e.e. to 95% e.e. (in increments of 5% e.e.) and (R)-α-ionone having an optical purity of 99% e.e. or more were prepared. Subsequently, such (R)-α-ionones were used instead of (R)-α-ionone having an optical purity of 70% e.e. in Example 37, to prepare peach flavor compositions (Example 65). In addition, (S)-α-ionones were used instead of such (R)-α-ionones in Example 61, to prepare peach flavor compositions (Example 66).

Examples 67 and 68

Peach Flavor Compositions

With regard to (R)-α-ionone having an optical purity of 70% e.e. that included at 0.05% by mass in the peach flavor compositions prepared in Example 37, its mixed amount was appropriately changed from 0.01 ppm to 50% by mass, to prepare peach flavor compositions (Example 67). In addition, (S)-α-ionones were used instead of such (R)-α-ionones in Example 67, to prepare peach flavor compositions (Example 68).

Test Examples 30 to 33

Evaluation Test

The peach flavor compositions prepared in Examples 65 and 66 and the peach flavor compositions prepared in Examples 67 and 68 were subjected to an evaluation test, in which 5 perfumers having 5 or more years of experience evaluated the aforementioned compositions by the same method as that described in the aforementioned test examples 26 to 29.

As a result of the evaluation test, it was found that the peach flavor compositions prepared in Examples 65 and 66 (Test example 30 and 31), which had an optical purity of 10% e.e. or more, even using either (R)-α-ionone or (S)-α-ionone, significantly exhibited the effect of the optical purity. In addition, such peach flavor compositions, which had an optical purity of 30% e.e. to 95% e.e., more significantly exhibited the effect of the optical purity. Moreover, such peach flavor compositions, which had an optical purity of almost 50% e.e. to 85% e.e., further more significantly exhibited the effect of the optical purity.

Furthermore, it was also found that even using either (R)-α-ionone or (S)-α-ionone, it may be better that the peach flavor compositions prepared in Examples 67 and 68 (Test example 30 and 31) are used within the range from 0.2 ppm to 20% by mass. A peach flavor composition used in a mixed amount of 0.2 ppm or more exhibited a clearer mixing effect than that of a peach flavor composition used in a mixed amount of less than 0.2 ppm. Moreover, it was found that a peach flavor composition used in a mixed amount of 20% by mass or less had a better balance of the flavor or taste of the fragrance composition than that of a peach flavor composition used in a mixed amount of more than 20% by mass.

INDUSTRIAL APPLICABILITY

The present invention provides a method for producing optically active α-ionone that is useful as a perfume, various types of intermediates, etc. This production method is able not only to give desired optically active α-ionone with a high yield and a high asymmetric yield, but also it is industrially extremely useful.

The invention claimed is:
1. An α-ionone enol ester, characterized in that said α-ionone enol ester has the following structure:

(3)

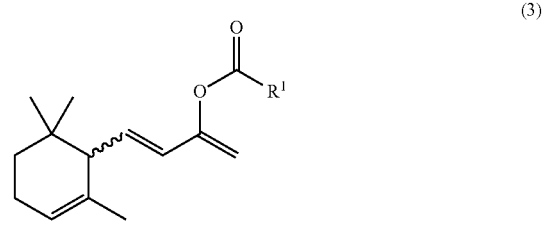

wherein R¹ represents a hydrogen atom or an optionally substituted hydrocarbon group.

2. The α-ionone enol ester according to claim 1, characterized in that said α-ionone enol ester is an optically active substance.

3. The α-ionone enol ester according to claim 2, characterized in that said α-ionone enol ester has the following structure:

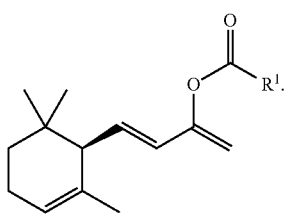

4. The α-ionone enol ester according to claim 2, characterized in that said α-ionone enol ester has the following structure:

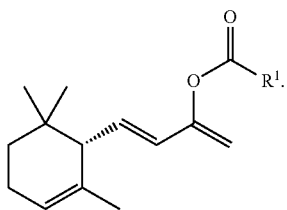

5. The α-ionone enol ester according to claim 1, wherein said hydrocarbon group is selected from a group consisting of an alkyl group having 1 to 20 carbon atoms, an alkenyl group having 2 to 20 carbon atoms, an alkynyl group having 2 to 20 carbon atoms, an alkadienyl group having 4 to 20 carbon atoms, an aryl group having 6 to 20 carbon atoms, and an aralkyl group having 7 to 20 carbon atoms.

6. The α-ionone enol ester according to claim 5, characterized in that said α-ionone enol ester is an optically active substance.

7. The α-ionone enol ester according to claim 1, wherein said hydrocarbon group is selected from the group consisting of methyl, ethyl, n-propyl, 2-propyl, n-butyl, 1-methylpropyl, isobutyl, tert-butyl, n-pentyl, 1-methylbutyl, tert-pentyl, 2-methylbutyl, 3-methylbutyl, 2,2-dimethylpropyl, n-hexyl, 1-methylpentyl, 1-ethylbutyl, tert-hexyl, 2-methylpentyl, 3-methylpentyl, 4-methylpentyl, 2-methylpentan-3-yl, heptyl, octyl, nonyl, decyl, lauryl, stearyl, cyclopropyl, cyclobutyl, cyclopentyl, cyclohexyl, vinyl, propenyl, butenyl, pentenyl, hexenyl, heptenyl, octenyl, nonenyl, decenyl, ethynyl, propynyl, butynyl, pentynyl, hexynyl, 1,3-butadienyl, 2,3-dimethyl-1,3-butadienyl, phenyl, naphthyl, anthryl, biphenyl, benzyl, 1-phenylethyl, 2-phenylethyl, 1-phenylpropyl, and 3-naphthylpropyl.

8. The α-ionone enol ester according to claim 7, characterized in that said α-ionone enol ester is an optically active substance.

9. The α-ionone enol ester according to claim 1, selected from the group consisting of

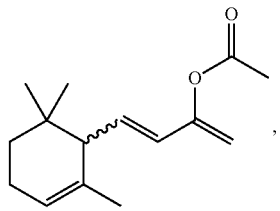

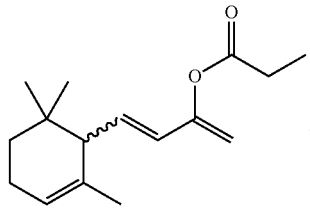

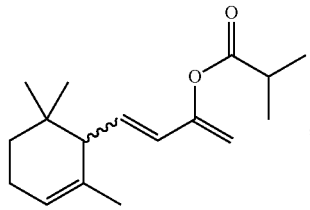

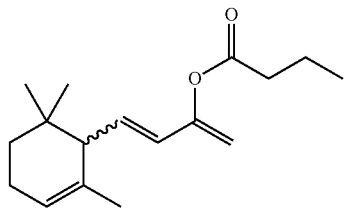

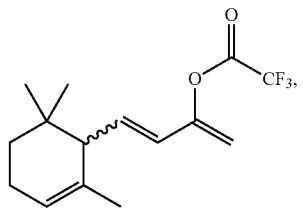

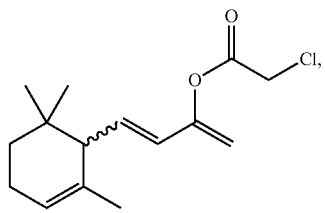

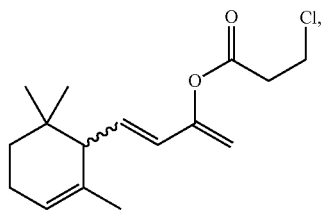

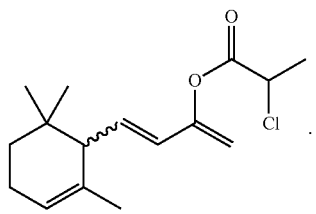

-continued

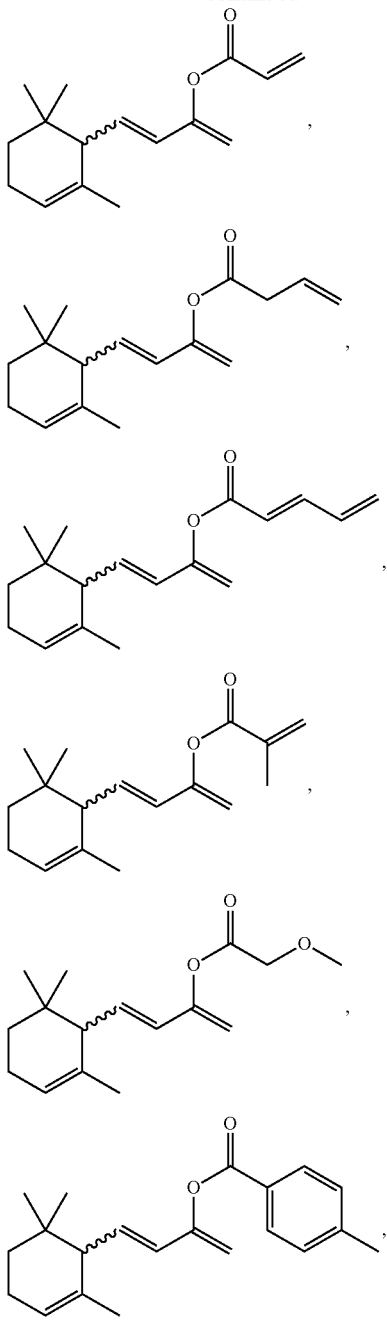

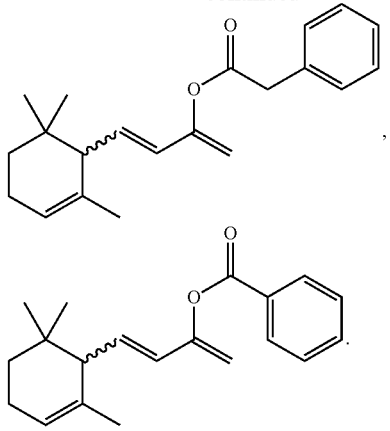

10. The α-ionone enol ester according to claim 1, wherein $R^1$ is methyl.

11. The α-ionone enol ester according to claim 2, wherein $R^1$ is methyl.

12. The α-ionone enol ester according to claim 4, characterized in that said α-ionone enol ester has the following structure:

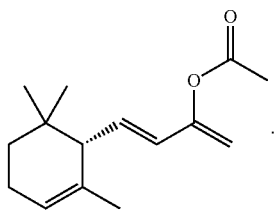

13. The α-ionone enol ester according to claim 3, characterized in that said α-ionone enol ester has the following structure:

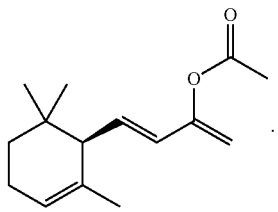

* * * * *